(12) United States Patent
van Es et al.

(10) Patent No.: US 7,332,337 B2
(45) Date of Patent: Feb. 19, 2008

(54) VIRAL VECTORS HAVING TISSUE TROPISM FOR T-LYMPHOCYTES, B- AND MAST CELLS

(75) Inventors: Helmuth Hendrikus Gerardus van Es, Hoofddorp (NL); Marlijn van Zutphen, Leiderdorp (NL); Libin Ma, Oegstgeest (NL); Menzo Jans Emko Havenga, Alphen a/d Rijn (NL)

(73) Assignee: Galapagos NV, Mechelen (BE)

( * ) Notice: Subject to any disclaimer, the term of this patent is extended or adjusted under 35 U.S.C. 154(b) by 0 days.

(21) Appl. No.: 09/962,543

(22) Filed: Sep. 25, 2001

(65) Prior Publication Data

US 2003/0180258 A1 Sep. 25, 2003

Related U.S. Application Data

(63) Continuation-in-part of application No. PCT/NL00/00325, filed on May 16, 2000.

(60) Provisional application No. 60/290,403, filed on May 11, 2001.

(51) Int. Cl.
*C12N 15/09* (2006.01)

(52) U.S. Cl. .................... 435/455; 424/93.1; 424/93.2; 424/93.21; 435/69.1; 435/320.1; 435/325; 514/44

(58) Field of Classification Search ............... 514/44; 435/320.1, 69.1, 455
See application file for complete search history.

(56) References Cited

U.S. PATENT DOCUMENTS 6,057,155 A * 5/2000 Wickham et al. ........... 435/325
6,210,946 B1 * 4/2001 Curiel et al. ............. 435/235.1
6,455,314 B1 * 9/2002 Wickham et al. ........... 435/456

FOREIGN PATENT DOCUMENTS

WO WO 00/42208 7/2000

OTHER PUBLICATIONS

Shayakhmelov et al, J Virol 2000;74:2567-83.*
von Seggern et al, J Virol 2000;74:354-62.*
Ngo, in The Protein Folding Problem and Tertiary Structure Prediction, Merz et al. (eds.), Birkhauser Boston: Boston MA, pp. 433 and 492-495, 1994.*
Ophorst et al, Vaccin 2004;22:3035-44.*
Rudinger, Peptide Hormones, Parsons (ed.), University Park Press: Baltimore, MD, pp. 1-7, 1976.*
Bowie et al, Science Mar. 1990; 247:1306-10.*
Einfeld et al, J Virol 1999;73:9130-6.*
de Jong et al, J Clin Microbiol 1999;37:3940-5.*
Sakurai et al, Mol Ther 2003;8:813-21.*
Gaggar et al, Nat Med 2003;9:1408-12.*
Vigne et al et al, Gene Ther 2003;10:153-62.*
Frey et al, Blood 1998;91:2781-92.*
Donahue et al, Blood 1996;88:4166-72.*
Leon et al, PNAS 1998;95:13159-64.*
Orkin et al. NIH Report on Gene Therapy, Dec. 1995.*
Peterson, Statement of Amy Patterson M.D., Feb. 2000.*
Anderson, Hum Gene Ther 2002;13:1261-2.*
Segerman. A. et al.: "Adenovirus Types 11p and 35p Show High Binding Efficiencies for Committed Hematopoietic Cell Lines and Are Infective to Thse Cell Lines," Journal of Virology, pp. 1457-1467 (Feb. 2000).
M. Conley: "*Genes required for B cell development*", Journal of Clinical Investigation, vol. 112 No. 11, pp. 1636-1638 (Dec. 2003).
M. Rosenzweig, et al.: "*In Vitro T Lymphopoiesis of Human and Rhesus CD34+ Progenitor Cells*", Blood vol. 87, No. 10, pp. 4040-4048 (May 15, 1996).
E. Drew, et al: "*CD34 expression by mast cells: of mice and men*", Blood vol. 106, No. 5, pp. 1885-1887 (Sep. 1, 2005).
R. Berenson, et al.: "*Engraftment After Infusion of CD34+ Marrow Cells in Patients with Breast Cancer or Neuroblastoma*", Blood vol. 77, No. 8, pp. 1717-1722 (Apr. 15, 1991).

* cited by examiner

*Primary Examiner*—Q. Janice Li
(74) *Attorney, Agent, or Firm*—Synnestvedt & Lechner LLP

(57) ABSTRACT

The present invention relates to methods of introducing an expressible non-viral nucleic acid sequence into a T lymphocyte cell, a B-cell, or a mast cell, comprising contacting the cell with a viral particle containing a modified viral coat proteins containing adenoviral amino acid sequence from an adenoviral serotype Ad35 or Ad51 fiber protein, arrays of subpopulations of cells made by such methods, and a method for a ex vivo transduction of a population of cells.

16 Claims, 21 Drawing Sheets

Figure 4A: Amino acid sequence serotype 35 fiber protein:

MSVSSCSCPSAPTIFMLLQMKRARPSEDTFNPVYPYEDESTSQHPFINPGFISP
NGFTQSPDGVLTLKCLTPLTTTGGSLQLKVGGGLTVDDTDGTLQENIRATAPIT
KNNHSVELSIGNGLETQNNKLCAKLGNGLKFNNGDICIKDSINTLWTGINPPPN
CQIVENTNTNDGKLTLVLVKNGGLVNGYVSLVGVSDTVNQMFTQKTANIQLR
LYFDSSGNLLTEESDLKIPLKNKSSTATSETVASSKAFMPSTTAYPFNTTTRDSE
NYIHGICYYMTSYDRSLFPLNISIMLNSRMISSNVAYAIQFEWNLNASESPESNI
MTLTTSPFFFSYITEDDN.

Figure 4B: Amino acid sequence serotype 51 fiber protein:

MSVSSCSCPSAPTIFMLLQMKRARPSEDTFNPVYPYEDESTSQHPFINPGFISP
NGFTQSPDGVLTLNCLTPLTTTGGPLQLKVGGGLIVDDTDGTLQENIRVTAPITK
NNHSVELSIGNGLETQNNKLCAKLGNGLKFNNGDICIKDSINTLWTGIKPPPNC
QIVENTDTNDGKLTLVLVKNGGLVNGYVSLVGVSDTVNQMFTQKSATIQLRL
YFDSSGNLLTDESNLKIPLKNKSSTATSEAATSSKAFMPSTTAYPFNTTTRDSEN
YIHGICYYMTSYDRSLVPLNISIMLNSRTISSNVAYAIQFEWNLNAKESPESNIAT
LTTSPFFFSYIIEDTTKCISLCYVSTCLFFN

Figure 8
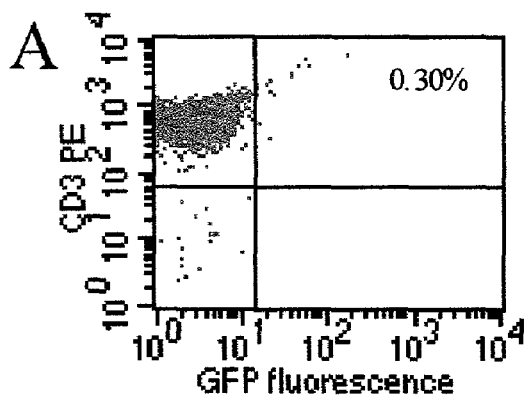 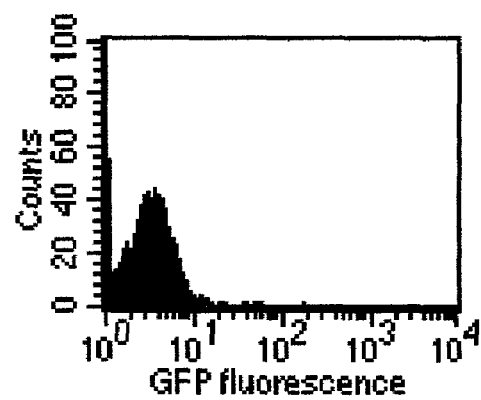
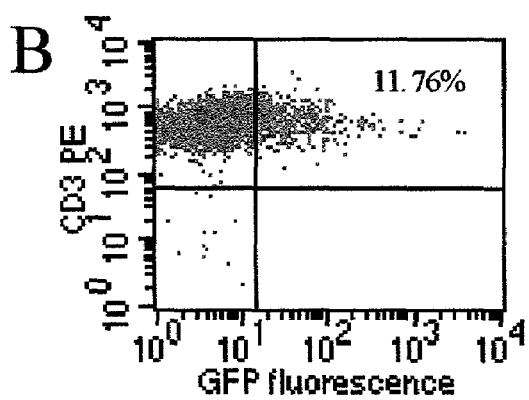 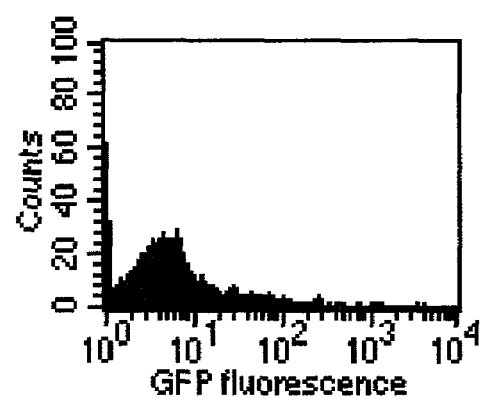
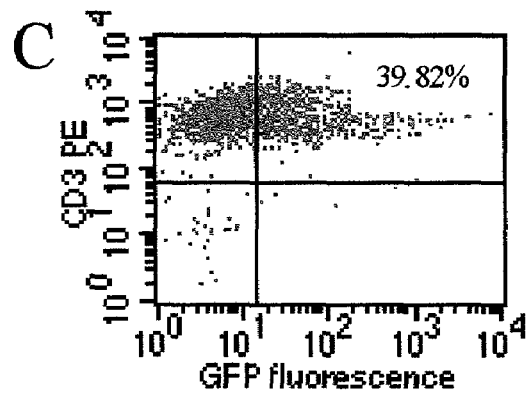 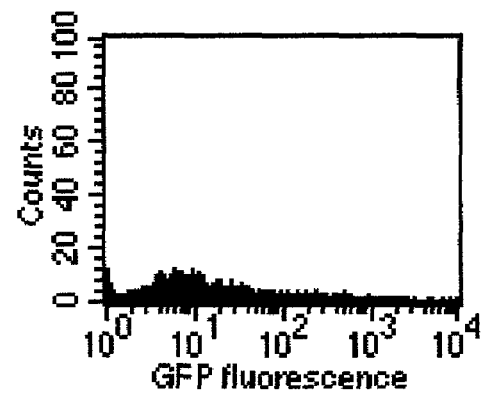

Figure 9B
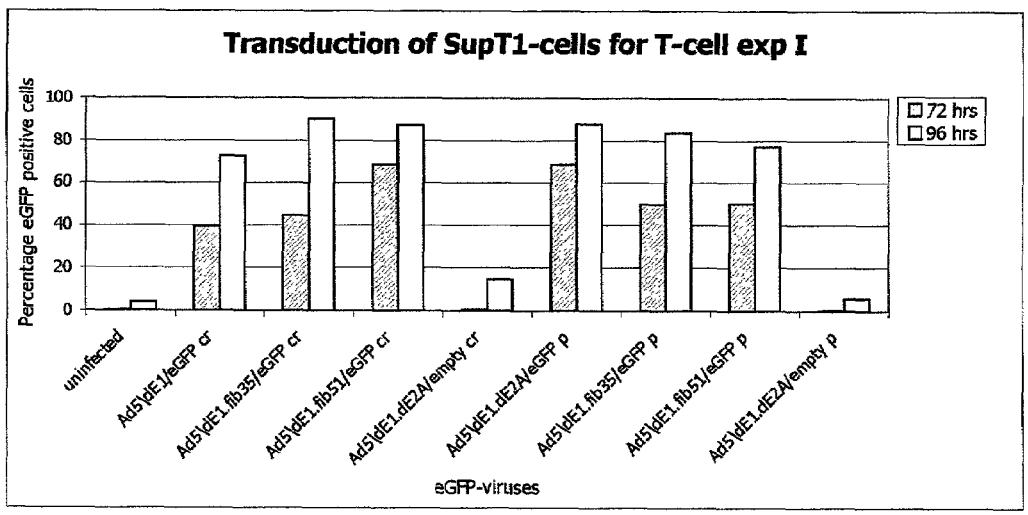
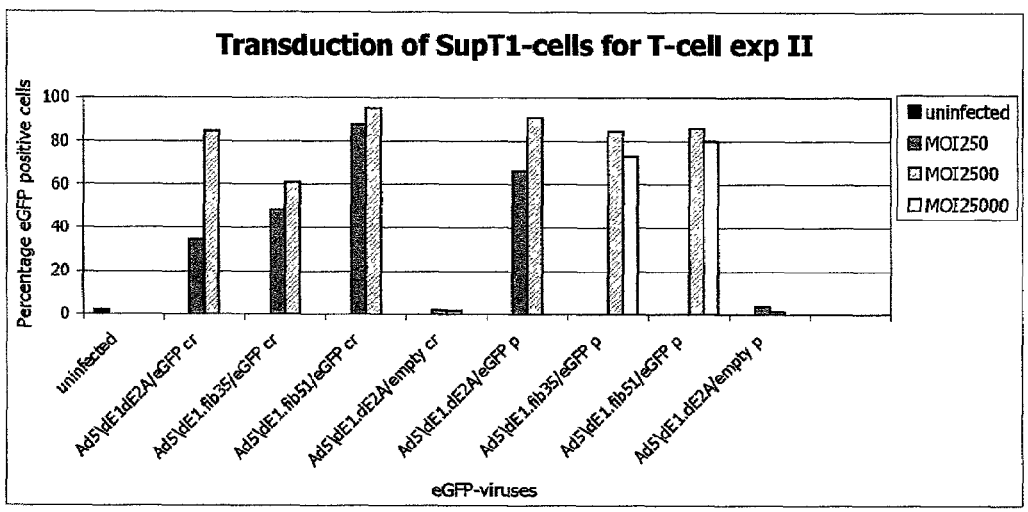
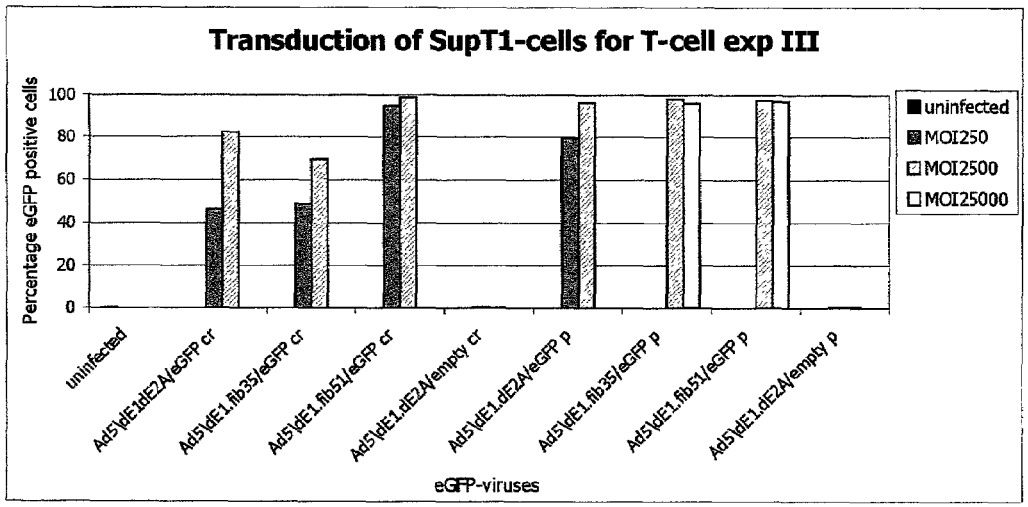

Figure 9C
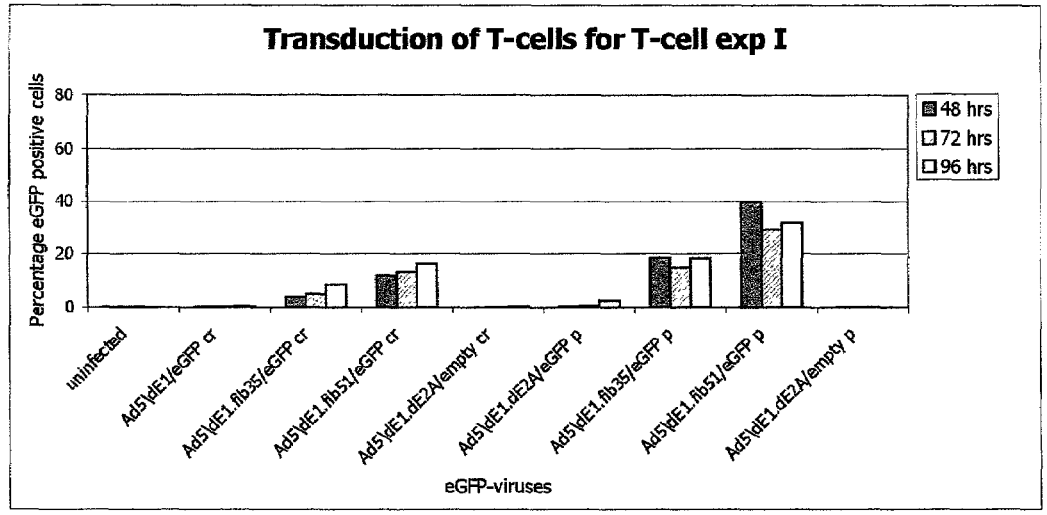
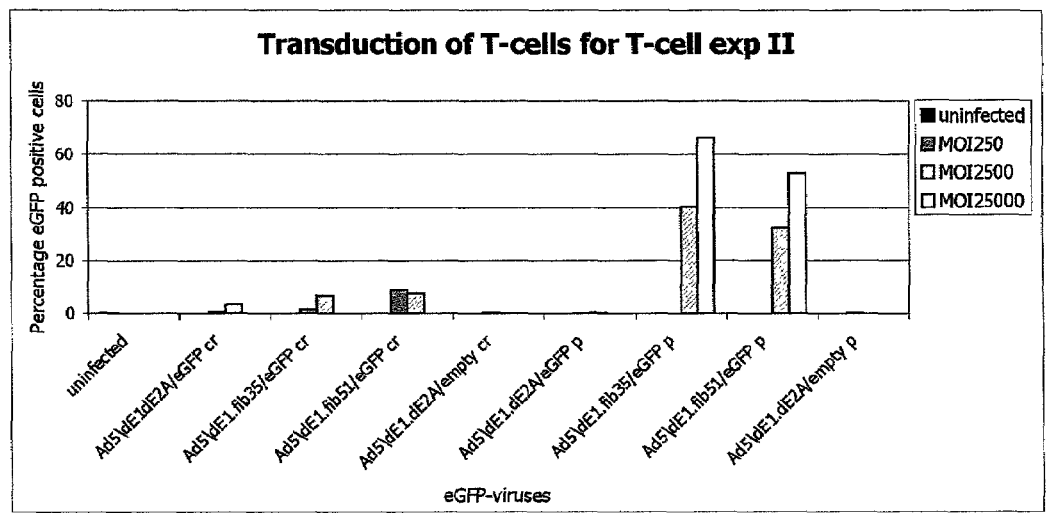
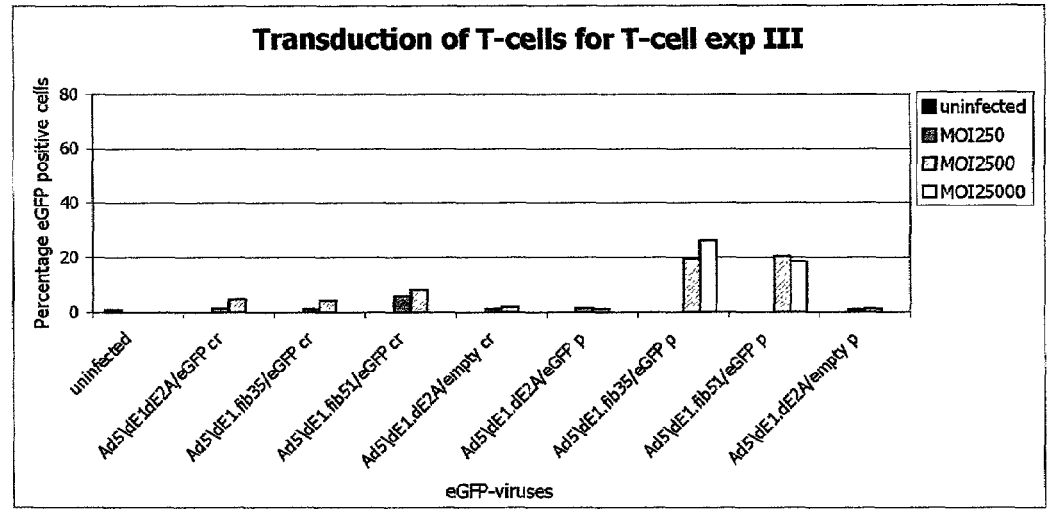

Figure 10
A
MOI 250
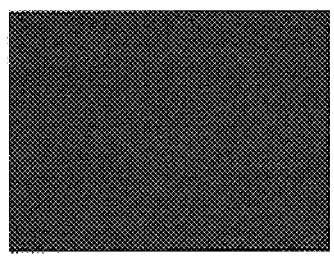 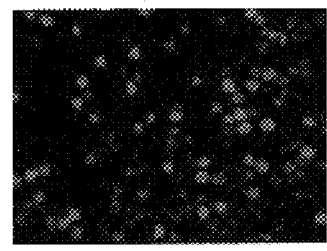
MOI 1000
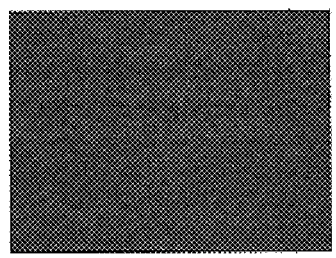 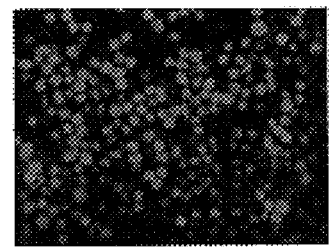
MOI 2500
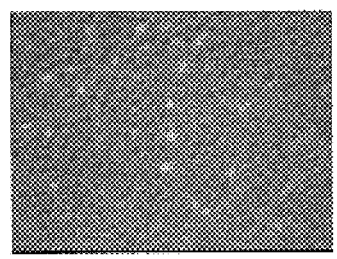 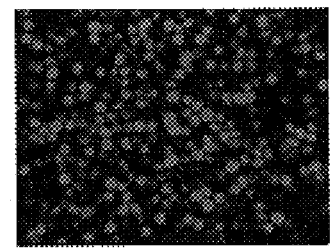

Figure 10
B
MOI 250
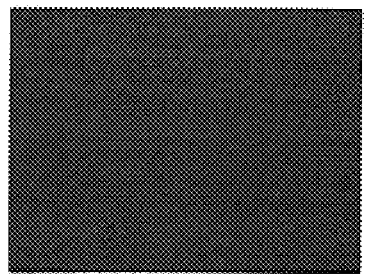 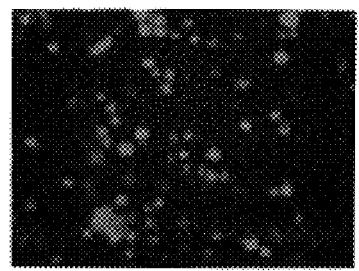
MOI 1000
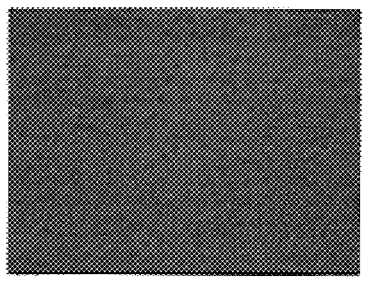 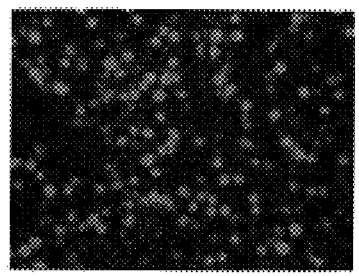
MOI 2500
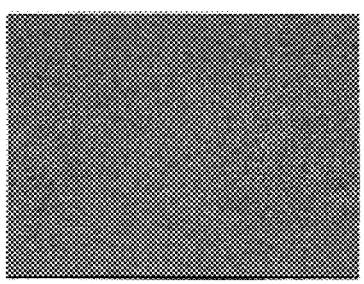 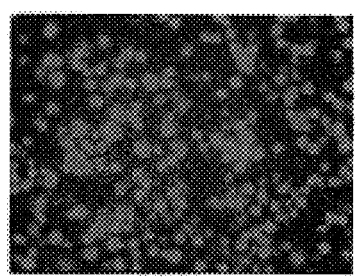

Figure 12
A
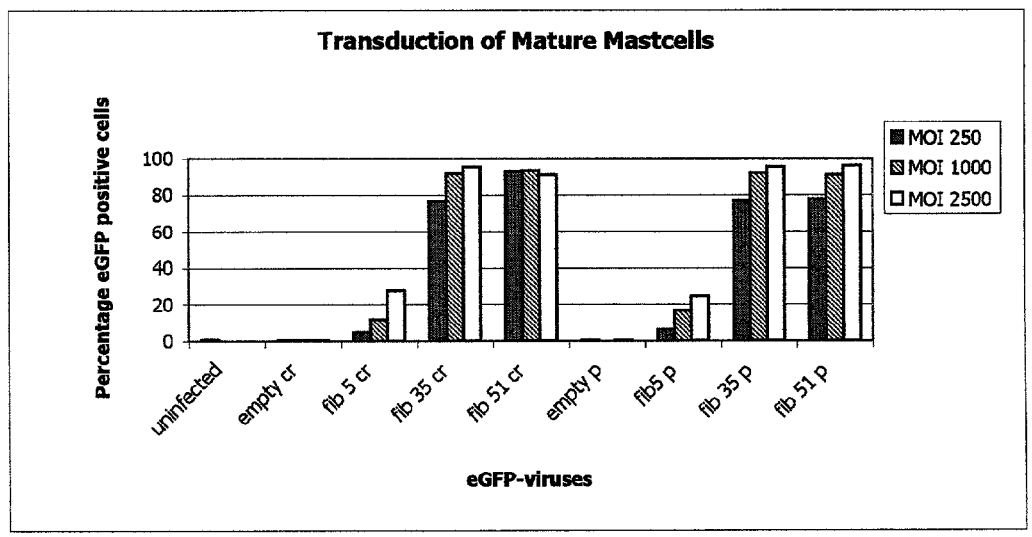
B
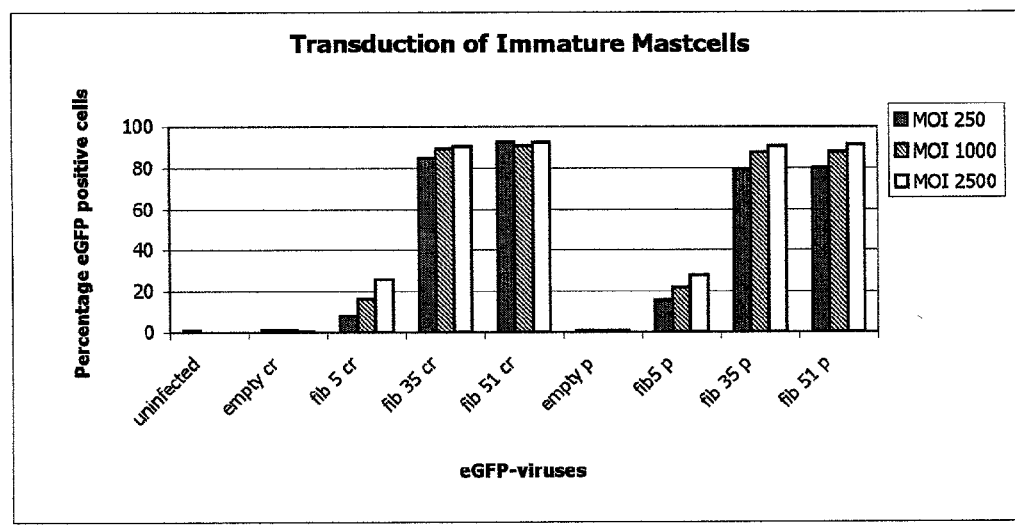

Figure 13
A
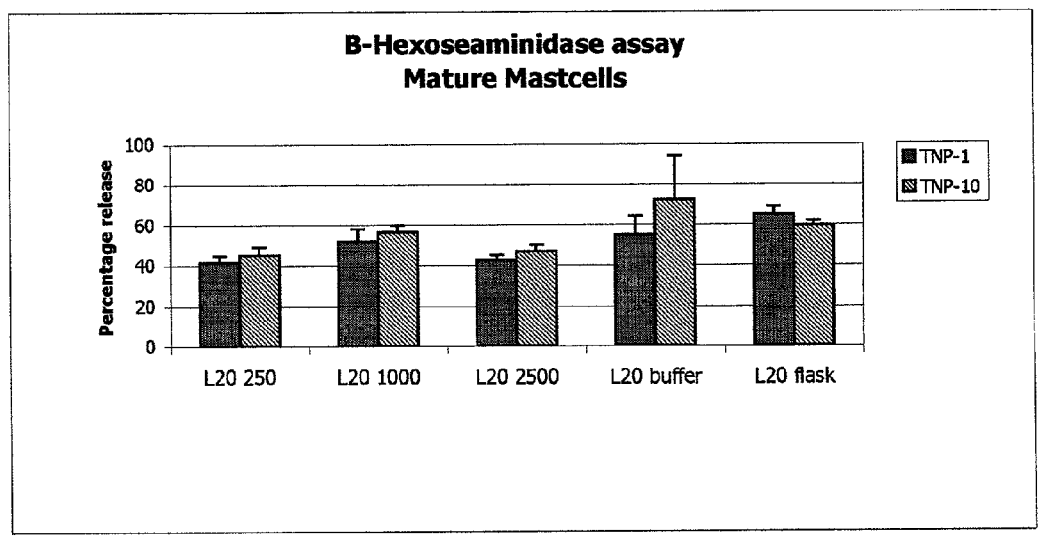
B
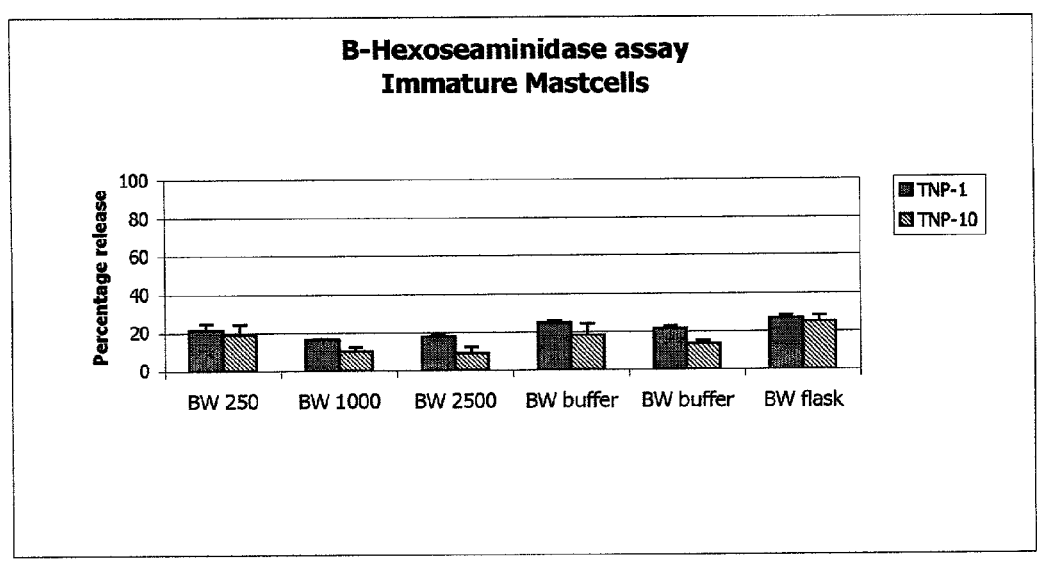

Figure 15
A
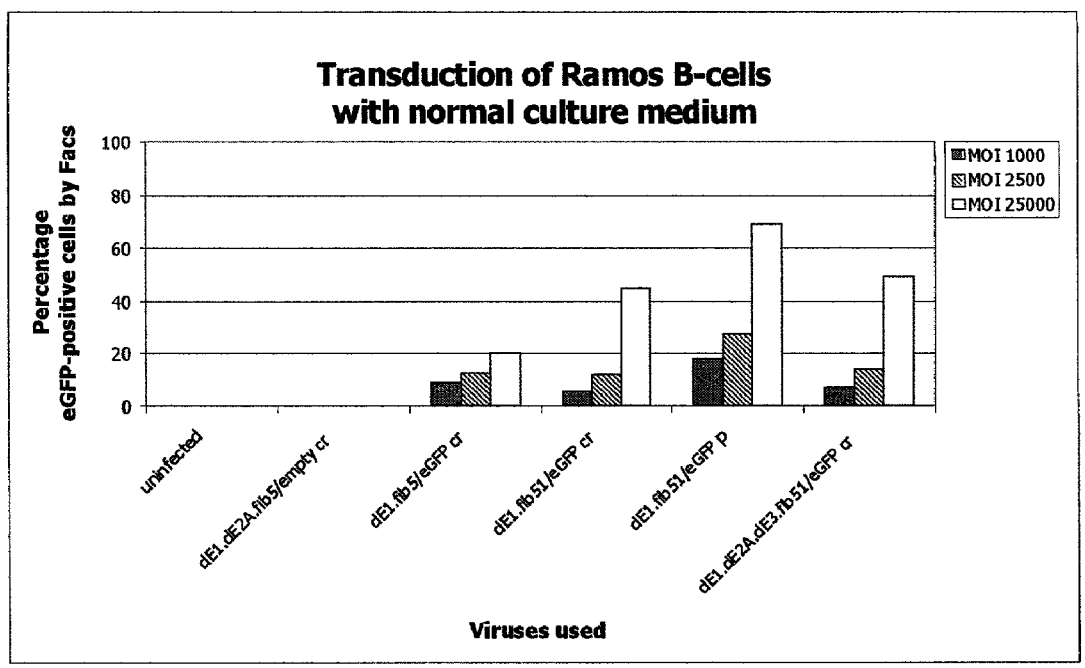
B
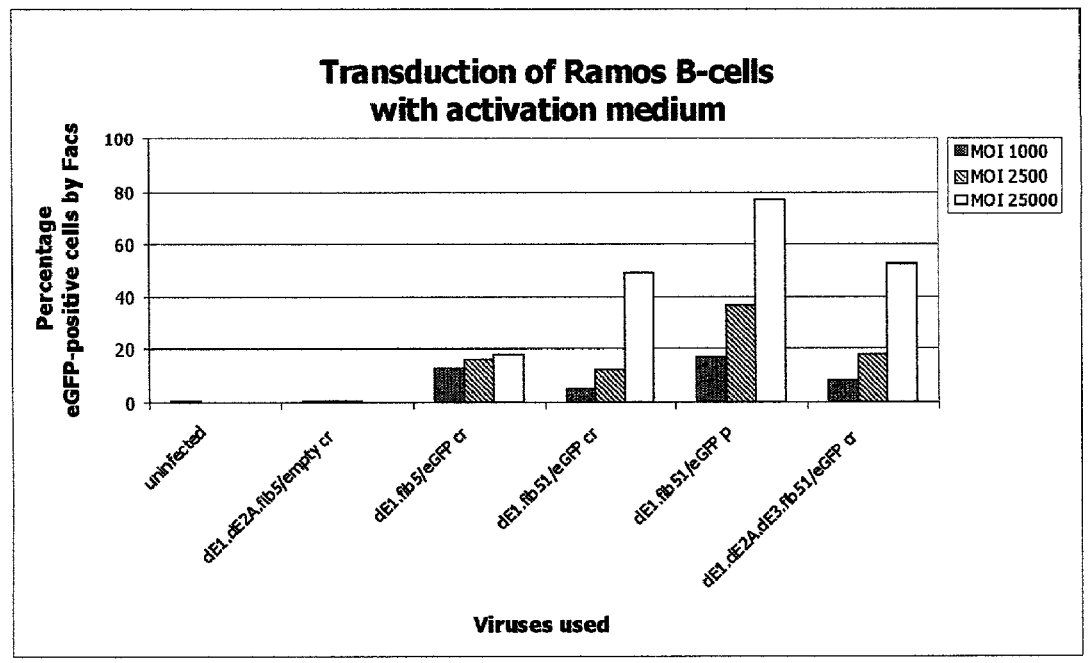

SEQUENCE LISTING

<160> NUMBER OF SEQ ID NOS: 15

<210> SEQ ID NO 1
<211> LENGTH: 342
<212> TYPE: PRT
<213> ORGANISM: Adenovirus Ad35

<400> SEQUENCE: 1

```
Met Ser Val Ser Ser Cys Ser Cys Pro Ser Ala Pro Thr Ile Phe Met
1               5                   10                  15

Leu Leu Gln Met Lys Arg Ala Arg Pro Ser Glu Asp Thr Phe Asn Pro
            20                  25                  30

Val Tyr Pro Tyr Glu Asp Glu Ser Thr Ser Gln His Pro Phe Ile Asn
        35                  40                  45

Pro Gly Phe Ile Ser Pro Asn Gly Phe Thr Gln Ser Pro Asp Gly Val
    50                  55                  60

Leu Thr Leu Lys Cys Leu Thr Pro Leu Thr Thr Thr Gly Gly Ser Leu
65                  70                  75                  80

Gln Leu Lys Val Gly Gly Gly Leu Thr Val Asp Asp Thr Asp Gly Thr
                85                  90                  95

Leu Gln Glu Asn Ile Arg Ala Thr Ala Pro Ile Thr Lys Asn Asn His
            100                 105                 110

Ser Val Glu Leu Ser Ile Gly Asn Gly Leu Glu Thr Gln Asn Asn Lys
        115                 120                 125

Leu Cys Ala Lys Leu Gly Asn Gly Leu Lys Phe Asn Asn Gly Asp Ile
    130                 135                 140

Cys Ile Lys Asp Ser Ile Asn Thr Leu Trp Thr Gly Ile Asn Pro Pro
145                 150                 155                 160

Pro Asn Cys Gln Ile Val Glu Asn Thr Asn Thr Asn Asp Gly Lys Leu
                165                 170                 175

Thr Leu Val Leu Val Lys Asn Gly Gly Leu Val Asn Gly Tyr Val Ser
            180                 185                 190

Leu Val Gly Val Ser Asp Thr Val Asn Gln Met Phe Thr Gln Lys Thr
        195                 200                 205

Ala Asn Ile Gln Leu Arg Leu Tyr Phe Asp Ser Ser Gly Asn Leu Leu
    210                 215                 220

Thr Glu Glu Ser Asp Leu Lys Ile Pro Leu Lys Asn Lys Ser Ser Thr
225                 230                 235                 240

Ala Thr Ser Glu Thr Val Ala Ser Ser Lys Ala Phe Met Pro Ser Thr
                245                 250                 255

Thr Ala Tyr Pro Phe Asn Thr Thr Thr Arg Asp Ser Glu Asn Tyr Ile
            260                 265                 270

His Gly Ile Cys Tyr Tyr Met Thr Ser Tyr Asp Arg Ser Leu Phe Pro
        275                 280                 285

Leu Asn Ile Ser Ile Met Leu Asn Ser Arg Met Ile Ser Ser Asn Val
    290                 295                 300

Ala Tyr Ala Ile Gln Phe Glu Trp Asn Leu Asn Ala Ser Glu Ser Pro
305                 310                 315                 320

Glu Ser Asn Ile Met Thr Leu Thr Thr Ser Pro Phe Phe Phe Ser Tyr
```

Ile Thr Glu Asp Asp Asn
                340

<210> SEQ ID NO 2
<211> LENGTH: 357
<212> TYPE: PRT
<213> ORGANISM: Adenovirus Ad51

<400> SEQUENCE: 2

Met Ser Val Ser Ser Cys Ser Cys Pro Ser Ala Pro Thr Ile Phe Met
1               5                   10                  15

Leu Leu Gln Met Lys Arg Ala Arg Pro Ser Glu Asp Thr Phe Asn Pro
            20                  25                  30

Val Tyr Pro Tyr Glu Asp Glu Ser Thr Ser Gln His Pro Phe Ile Asn
        35                  40                  45

Pro Gly Phe Ile Ser Pro Asn Gly Phe Thr Gln Ser Pro Asp Gly Val
    50                  55                  60

Leu Thr Leu Asn Cys Leu Thr Pro Leu Thr Thr Gly Gly Pro Leu
65                  70                  75                  80

Gln Leu Lys Val Gly Gly Leu Ile Val Asp Thr Asp Gly Thr
            85                  90                  95

Leu Gln Glu Asn Ile Arg Val Thr Ala Pro Ile Thr Lys Asn Asn His
            100                 105                 110

Ser Val Glu Leu Ser Ile Gly Asn Gly Leu Glu Thr Gln Asn Asn Lys
        115                 120                 125

Leu Cys Ala Lys Leu Gly Asn Gly Leu Lys Phe Asn Asn Gly Asp Ile
    130                 135                 140

Cys Ile Lys Asp Ser Ile Asn Thr Leu Trp Thr Gly Ile Lys Pro Pro
145                 150                 155                 160

Pro Asn Cys Gln Ile Val Glu Asn Thr Asp Thr Asn Asp Gly Lys Leu
                165                 170                 175

Thr Leu Val Leu Val Lys Asn Gly Gly Leu Val Asn Gly Tyr Val Ser
            180                 185                 190

Leu Val Gly Val Ser Asp Thr Val Asn Gln Met Phe Thr Gln Lys Ser
        195                 200                 205

Ala Thr Ile Gln Leu Arg Leu Tyr Phe Asp Ser Ser Gly Asn Leu Leu
    210                 215                 220

Thr Asp Glu Ser Asn Leu Lys Ile Pro Leu Lys Asn Lys Ser Ser Thr
225                 230                 235                 240

Ala Thr Ser Glu Ala Ala Thr Ser Ser Lys Ala Phe Met Pro Ser Thr
                245                 250                 255

Thr Ala Tyr Pro Phe Asn Thr Thr Arg Asp Ser Glu Asn Tyr Ile
            260                 265                 270

His Gly Ile Cys Tyr Tyr Met Thr Ser Tyr Asp Arg Ser Leu Val Pro
        275                 280                 285

Leu Asn Ile Ser Ile Met Leu Asn Ser Arg Thr Ile Ser Ser Asn Val
    290                 295                 300

Ala Tyr Ala Ile Gln Phe Glu Trp Asn Leu Asn Ala Lys Glu Ser Pro
305                 310                 315                 320

Glu Ser Asn Ile Ala Thr Leu Thr Ser Pro Phe Phe Ser Tyr
                325                 330                 335

Ile Ile Glu Asp Thr Thr Lys Cys Ile Ser Leu Cys Tyr Val Ser Thr
            340                 345                 350

-continued

Cys Leu Phe Phe Asn
            355

<210> SEQ ID NO 3
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 3
cccgtgtatc catatgatgc agacaacgac cgacc                              35

<210> SEQ ID NO 4
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 4
cccgtctacc catatggcta cgcgcgg                                       27

<210> SEQ ID NO 5
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 5
cckgtstacc catatgaaga tgaaagc                                       27

<210> SEQ ID NO 6
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 6
cccgtctacc catatgacac ctyctcaact c                                  31

<210> SEQ ID NO 7
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 7
cccgtttacc catatgaccc atttgacaca tcagac                             36

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 8
ccgatgcatt tattgttggg ctatatagga                                    30

<210> SEQ ID NO 9
<211> LENGTH: 30
<212> TYPE: DNA

<213> ORGANISM: Artificial Sequence
<220> FEATURE:
<223> OTHER INFORMATION: Synthetic oligonucleotide

<400> SEQUENCE: 9
ccgatgcatt yattcttggg cratatagga                                30

<210> SEQ ID NO 10
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 10
ccgatgcatt tattcttggg raatgtawga aaagga                         36

<210> SEQ ID NO 11
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 11
ccgatgcatt cagtcatctt ctctgatata                                30

<210> SEQ ID NO 12
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 12
ccgatgcatt tattgttcag ttatgtagca                                30

<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 13
gccatgcatt tattgttctg ttacataaga                                30

<210> SEQ ID NO 14
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 14
ccgttaatta agcccttatt gttctgttac ataagaa                        37

<210> SEQ ID NO 15
<211> LENGTH: 30
<212> TYPE: DNA
<213> ORGANISM: Artificial Sequence

```
<220> FEATURE:
<223> OTHER INFORMATION: Synthetic oligonucleotide

<400> SEQUENCE: 15
ccgatgcatt cagtcatcyt ctwtaatata                                          30
```

VIRAL VECTORS HAVING TISSUE TROPISM FOR T-LYMPHOCYTES, B- AND MAST CELLS

CROSS-REFERENCE TO RELATED APPLICATIONS

This application is a continuation in part of PCT/NL00/00325 (international filing date: May 16, 2000) which was published on Nov. 23, 2000 under PCT Article 21(2) in English, and claim the benefit of U.S. Provisional Application No. 60/290,403, filed May 11, 2001, and European Patent Office Application 00203375.1, filed Sep. 25, 2000.

FIELD OF THE INVENTION

The invention relates to the field of molecular genetics and medicine. In particular the present invention relates to the field of functional genomics and gene therapy, in particular, methods useful in ex vivo gene therapy and functional genomics using adenovirus vectors.

In functional genomics, genetic information with unknown function but somehow pre-selected for, is usually delivered to a host cell in order to either correct (supplement) a genetic deficiency in said cell, or to inhibit an undesired function in said cell or to otherwise induce a phenotype. Of course the genetic information can also be intended to provide the host cell with a desired function, e.g. to supply a secreted protein or express a transcription factor.

Many different methods have been developed to introduce new genetic information into cells. Although many different systems may work on cell-lines cultured in vitro, only the group of viral vector mediated gene delivery methods seems to be able to meet the required efficiency of gene transfer in vivo. Thus for gene therapy purposes most of the attention is directed towards the development of suitable viral vectors. Today, most of the attention for the development of suitable viral vectors is directed towards those vectors that are based on adenoviruses. Studies in clinical trials have provided valuable information on the use of these vectors in patients. Moreover adenoviral vectors are relatively easy to concentrate and purify. For functional genomics adenoviral vectors are also ideally suited. They can be used to build gene expression libraries that can be used with specific cell based assays to search for genes or antagonists of those genes that give a desired phenotype. They can also be used to validate genes further that have been isolated using other gene selection techniques such as comparative expression profiling and subtraction techniques. Validation using adenoviral vectors can be done in vitro as well as in vivo using either in situ or in vitro cell or tissue based assays or appropriate animal models.

Some characteristics of the current adenoviral vectors limit their use in specific applications. For instance endothelial cells, smooth muscle cells, T-lymphocytes and mast cells are not easily transduced by the current generation of adenoviral vectors. For many gene therapy or functional genomics applications, preferably these types of cells should be genetically modified. Disease areas for which efficient gene transfer into these cell types is desirable include but are not limited to autoimmune disorders, cancer, infectious diseases, cardiovascular diseases and bone disorders.

T-lymphocytes are formed in the bone marrow, migrate to and mature in the thymus and then enter the peripheral blood and lymphatic circulation. T-lymphocytes are subdivided into three distinct types of cells: helper T-lymphocytes, suppressor T-lymphocytes, and cytotoxic T-lymphocytes. T-lymphocytes, unlike B-lymphocytes, do not produce antibody molecules, but express a heterodimeric cell surface receptor that recognizes peptide fragments of antigenic proteins that are attached to proteins of the major histocompatibility complex (MHC) and expressed on the surfaces of target T-lymphocytes (e.g. Abbas et al, 1991).

Human cytotoxic T-lymphocytes (CTLs) are typically of the $CD3^+$, $CD8^+$, $CD4^-$ phenotype and lyse cells that display fragments of foreign antigens associated with MHC class I molecules on their cell surfaces. Target T-lymphocytes for CTL recognition include normal cells expressing antigens after infection by viruses or other pathogens; and tumor cells that have undergone transformation and are expressing mutated proteins or are over-expressing normal proteins.

Helper T-lymphocytes are also $CD3^+$ but can be distinguished from cytotoxic T-lymphocytes by expression of CD4 but absence of the CD8 membrane protein. $CD4^+$ helper T-lymphocytes recognize fragments of antigens presented in association with MHC class II molecules, and primarily function to produce cytokines that amplify antigen-specific T- and B-cell responses and activate accessory immune cells such as monocytes or macrophages (e.g. Abbas et al, 1991).

$CD4^+$ helper and $CD8^+$ cytotoxic T-lymphocytes are important components of the host immune response to viruses, bacterial pathogens and tumors. As a result, individuals with congenital, acquired or iatrogenic T-cell immunodeficiency diseases may develop life threatening infections or malignancies (for example, SCID, AIDS, etc.). Persons with diseases that are related to a deficiency of immunologically competent T-lymphocytes can potentially have specific immunity restored through adoptive immunotherapy, alternatively called adoptive transfer. In adoptive immunotherapy, one or more specific immunities can be conferred upon an individual by transferring T-lymphocytes having the desired antigenic specificities. The cells of interest are derived from the immunodeficient host or from a compatible specifically immunized host. The latter source is of course especially important in situations in which the immunodeficient host has an insufficient number of T-lymphocytes, or has T-lymphocytes that are insufficiently effective. Efficient and reproducible gene transfer into T-lymphocytes, in particular human T-lymphocytes, is of prime importance in the validation of new genes, and for the development of new immuno or gene therapies.

T-lymphocytes can be isolated or enriched for by using cell immuno affinity methods based for example on magnetic beads having anti CD3, CD4 or CD8 antibodies on their surface, thus cell isolation is based on T-cell specific cell surface markers. Common methodology used is the technology developed by Miltenyi et al. Preferred is to use the technology for depletion of cell types other than T-lymphocytes so that activation of the resting T-cells by for example CD3 antibodies is avoided. This is done by using antibodies against markers for other cell types of the hemopoietic system such as monocytes and B-lymphocytes.

Mast cells are a family of cells generally found around the blood vessels in the connective tissues, in the lining of the gut, and in the lungs. They are large mononuclear cells, heavily granulated and deeply stained by basic dyes. Mast cells have their origin in the bone marrow and are derived from CD34+ hematopoietic progenitor cells that migrate in the form of immature progenitors to the tissue, where they differentiate into mature mast cells. A key feature of mast cells is that they express receptors (FcεRI) on their cell membranes that bind with high affinity to the Fc portion of IgE. Once bound, the IgE molecules persist at the cell surface for weeks, and that cell will remain "sensitised" as long as enough antibodies remain attached, and will trigger the activation of the cells when it comes into contact with antigen. Activated mast cells secrete mediators that are either preformed and granule-associated (e.g. histamine, proteoglycans, and neutral proteases) or are synthesized de novo (e.g. leukotriene $C_4$, platelet activated factor and prostaglandin $D_2$). Furthermore, mast cells are potential sources of many cytokines. Being as effector cells in IgE-assiociated immune responses, mast cells play a prominent role in allergic diseases, including asthma, and in host resistance to parasites. Moreover, they are implicated in the genesis of other diseases such as pulmonary fibrosis.

As mentioned above, vectors used to transduce cells include the adenoviral vectors. Adenoviruses contain a linear double-stranded DNA molecule of approximately 36000 base pairs. It contains identical Inverted Terminal Repeats (ITR) of approximately 90–140 base pairs with the exact length depending on the serotype. The viral origins of replication are within the ITRs exactly at the genome ends. The transcription units are divided in early and late regions. Shortly after infection the E1A and E1B proteins are expressed and function in transactivation of cellular and adenoviral genes. The early regions E2A and E2B encode proteins (DNA binding protein, pre-terminal protein and polymerase) required for the replication of the adenoviral genome (reviewed in van der Vliet, 1995). The early region E4 encodes several proteins with pleiotropic functions e.g. transactivation of the E2 early promoter, facilitating transport and accumulation of viral mRNAs in the late phase of infection and increasing nuclear stability of major late pre-mRNAs (reviewed in Leppard, 1997). The early region 3 encodes proteins that are involved in modulation of the immune response of the host (Wold et al, 1995). The late region is transcribed from one single promoter (major late promoter) and is activated at the onset of DNA replication. Complex splicing and poly-adenylation mechanisms give rise to more than 12 RNA species coding for core proteins, capsid proteins (penton, hexon, fiber and associated proteins), viral protease and proteins necessary for the assembly of the capsid and shutdown of host protein translation (Imperiale et al, 1995).

The interaction of the virus with the host cell has mainly been investigated with the serotype C viruses Ad2 and Ad5. Binding occurs via interaction of the knob region of the protruding fiber with a cellular receptor. A receptor for Ad2, Ad5 and probably more adenoviruses, is known as the 'Coxsackievirus and Adenovirus Receptor' or CAR protein (Bergelson et al, 1997). Internalization is mediated through interaction of the RGD (Arg, Gly, Asp) sequence present in the penton base with cellular β1-integrins (Wickham et al, 1993). This may not be true for all serotypes, for example serotype 40 and 41 do not contain a RGD sequence in their penton base sequence (Kidd et al, 1993).

The initial step for successful infection is binding of adenovirus to its target cell, a process mediated through the fiber protein. The fiber protein has a trimeric structure (Stouten et al, 1992) with different lengths depending on the virus serotype (Signas et al, 1985; Kidd et al, 1993). Different serotypes have polypeptides with structurally similar N- and C-termini, but different middle stem regions. The first 30 amino acids at the N-terminus are involved in anchoring of the fiber to the penton base (Chroboczek et al, 1995), especially the conserved FNPVYP region in the tail (Arnberg et al, 1997). The C-terminus, or knob, is responsible for initial interaction with the cellular adenovirus receptor. After this initial binding, secondary binding between the capsid penton base and cell-surface integrins leads to internalization of viral particles in coated pits and endocytosis (Morgan et al, 1969; Svensson and Persson, 1984; Varga et al, 1991; Greber et al, 1993; Wickham et al, 1993). Integrins are αβ-heterodimers of which at least 19 α-subunits and 8 β-subunits have been identified (see http://nciarray.nci.nih.gov/cgi-bin/cards). The array of integrins expressed in cells is complex and will vary between cell types and cellular environment. Although the knob contains some conserved regions between serotypes, the knob proteins show a high degree of variability, indicating that different adenovirus receptors exist.

At present, six different subgroups of human adenoviruses have been proposed which in total encompass approximately 50 distinct adenovirus serotypes. Besides these human adenoviruses, many animal adenoviruses have been identified (e.g. Ishibashi and Yasue, 1984). A serotype is defined on the basis of its immunological distinctiveness as determined by quantitative neutralization with animal antiserum (horse, rabbit). If neutralization shows a certain degree of cross-reaction between two viruses, distinctiveness of serotype is assumed if A) the hemagglutinins are unrelated, as shown by lack of cross-reaction on hemagglutination-inhibition, or B) substantial biophysical/biochemical differences in DNA exist (Francki et al, 1991). The serotypes identified last (42–49) were isolated for the first time from HIV infected patients (Hierholzer et al, 1988; Schnurr et al, 1993). For reasons not well understood, most of such immuno-compromised patients shed adenoviruses that were never isolated from immuno-competent individuals (Hierholzer et al, 1988 and 1992; Khoo et al, 1995).

Besides differences towards the sensitivity against neutralizing antibodies of different adenovirus serotypes, adenoviruses in subgroup C such as Ad2 and Ad5 bind to different receptors as compared to adenoviruses from subgroup B such as Ad3 and Ad7 (Defer et al, 1990; Gall et al, 1996). Likewise, it was demonstrated that receptor specificity could be altered by exchanging the Ad3 knob protein with the Ad 5 knob protein, and vice versa (Krasnykh et al, 1996; Stevenson et al, 1995 and 1997). Serotypes 2, 4, 5 and 7 all have a natural affiliation towards lung epithelia and other respiratory tissues. In contrast, serotypes 40 and 41 have a natural affiliation towards the gastrointestinal tract. These serotypes differ in at least capsid proteins (penton-base, hexon), proteins responsible for cell binding (fiber protein), and proteins involved in adenovirus replication. It is unknown to what extent the capsid proteins determine the differences in tropism found between the serotypes. It may very well be that post-infection mechanisms determine cell-type specificity of adenoviruses. It has been shown that adenoviruses from subgroups A (Ad12 and Ad31), C (Ad2 and Ad5), D (Ad9 and Ad15), E (Ad4) and F (Ad4l) are all able to bind labeled soluble CAR (sCAR) protein when immobilized on nitrocellulose. Furthermore, binding of adenoviruses with these serotypes to Ramos cells, that express high levels of CAR but lack integrins (Roelvink et al, 1996), could be efficiently blocked by addition of sCAR to these viruses prior to infection (Roelvink et al, 1998). However, the fact that (at least some) members of these subgroups are able to bind CAR does not exclude that these viruses have different infection efficiencies in various cell types. For example subgroup D viruses have relatively short fiber shafts compared to subgroup A and C viruses. It has been postulated that the tropism of subgroup D viruses is to a large extent determined by the penton base binding to integrins (Roelvink et al, 1996 and 1998). Another example is provided by Zabner et al (1998) who have tested 14 different serotypes on infection of human ciliated airway epithelia (CAE) and found that serotype 17 (subgroup D) was bound and internalized more efficiently then all other viruses, including other members of subgroup D. Similar experiments using serotypes from subgroup A–F in primary fetal rat cells showed that adenoviruses from subgroup A and B were bound and internalized inefficiently whereas viruses from subgroup D were most efficiently bound and internalized (Law et al, 1998). Also in this case viruses within one subgroup displayed different infection efficiencies. The importance of fiber binding for the improved infection of Ad17 in CAE was shown by Armentano et al (WO 98/22609A1) who made a recombinant Ad2/LacZ virus with a fiber gene from Ad17 and showed that the chimaeric virus infected CAE more efficient then Ad2/LacZ viruses with Ad2 fibers.

Thus despite their shared ability to bind CAR, differences in the length of the fiber, knob sequence and other capsid proteins e.g. penton base, of the different serotypes may determine the efficiency by which an adenovirus infects a certain target cell. Of interest in this respect is the ability of Ad2 and Ad5 fibers but not of Ad3 fibers to bind to fibronectin III and MHC class I derived peptides. This suggests that adenoviruses are able to use cellular receptors other than CAR (Hong et al, 1997). Serotypes 40 and 41 (subgroup F) are known to carry two fiber proteins differing in the length of the shaft. The long shafted 41L fiber is shown to bind CAR whereas the short-shafted 41S is not capable of binding CAR (Roelvink et al, 1998). The receptor for the short fiber is not known.

Most adenoviral gene delivery vectors currently used in functional genomics, gene therapy or vaccination are derived from subgroup C adenoviruses Ad2 or Ad5. The vectors have at least a deletion in the E1 region that renders the recombinant virus replication defective. In this region, novel genetic information can then be introduced. It has been demonstrated extensively that recombinant adenoviruses, in particular serotype 5, are suitable for efficient transfer of genes in vivo to the liver, the airway epithelium and solid tumors in animal models and human xenografts in immuno-deficient mice (Bout 1996, 1997; Blaese et al, 1995).

The use of adenoviral vectors in functional genomics includes building gene expression libraries and in vitro and in vivo gene validation with appropriate meaningful cell based assays or animal models for a particular human disease. Transfer and subsequent expression of a cDNA into a desired cell-type may lead to relevant phenotypic changes that may or may not confirm the role a particular cDNA plays in a particular disease. Alternatively such an exercise may lead to better insight into the validity of using a particular cDNA as a target for therapeutic intervention. In addition to sense copies of a gene or genes under investigation, antisense copies is cloned into the adenoviral vector and used for validation studies.

Gene transfer vectors derived from adenoviruses (adenoviral vectors) have a number of features that make them particularly useful for gene transfer:
1) the biology of the adenoviruses is well characterized,
2) the adenovirus is not associated with severe human pathology,
3) the virus is extremely efficient in introducing its DNA into the host cell,
4) the virus can infect a wide variety of cells and has a broad host-range,
5) the virus can be produced at high titers in large quantities,
6) and the virus can be rendered replication defective by deletion of the early-region 1 (E1) of the viral genome (Brody and Crystal, 1994),
7) the vectors can be produced free of wildtype replicating adenovirus (WO 97/00326A1).

However, there are still a number of drawbacks associated with the use of adenoviral vectors:
1) adenoviruses, especially the well investigated serotypes Ad2 and Ad5, usually elicit an immune response by the host into which they are introduced,
2) the replication and other functions of the adenovirus, which are provided with the additional genetic material, are not always very well suited for the cells.
3) the serotypes Ad2 and Ad5 are not ideally suited for delivering additional genetic material to organs other than the liver. Delivery of vectors derived from Ad2 or Ad5 via the bloodstream leads to a significant delivery of these vectors to the cells of the liver. In therapies where other cell types then liver cells need to be transduced, some means of liver exclusion must be applied to prevent uptake of the vector by these cells. Current methods rely on the physical separation of the vector from the liver cells. This can be done by localizing the vector and/or the target organ via surgery, balloon angioplasty or direct injection into an organ via for instance needles. Liver exclusion is also being practiced by surgical targeting in which the vector is delivered to compartments in the body that are essentially isolated from the bloodstream. This prevents transport of the vector to the liver. Although these methods mostly succeed in avoiding gross delivery of the vector to the liver, most of the methods are crude and have still considerable leakage and/or have poor target tissue penetration characteristics. In some cases inadvertent delivery of the vector to liver cells can be toxic to the patient. For instance, delivery of a herpes simplex virus (HSV) thymidine kinase (TK) gene for the subsequent killing of dividing cancer cells through administration of ganciclovir, is quite dangerous when also a significant amount of liver cells are transduced by the vector. Significant delivery and subsequent expression of the HSV-TK gene to liver cells is associated with severe toxicity. Thus there is a discrete need for an inherently safe vector provided with the property of a reduced transduction efficiency of liver cells.
4) In vitro or ex vivo gene transfer for functional genomics using standard Ad2 or Ad5 adenoviral vectors can be very limited in particular cells of the hemopoietic system as well as cells of the vasculature, such as endothelial cells. In particular primary T-lymphocytes are difficult to transduce with adenoviral vectors, making vectors of this serotype difficult to use for in vitro, in vivo or ex vivo gene validation studies involving T-lymphocytes.

T-lymphocytes are primary targets in numerous gene therapy protocols. However, the use of subgroup C adenovirus serotypes 2 or 5 (Ad2 or Ad5) as a vector to transduce T-lymphocytes is hampered by its poor transduction efficiency for these cells.

Gene transfer to mast cells is also characterized by poor transduction efficiency using the adenoviral vectors currently available. Mast cells are derived from haemopoietic stem cells and are from bone marrow origin. The cells can be cultured from CD34+ progenitors. Mast cells play a distinct role in acute inflammation. During the sensibilisation-phase, the immune system becomes stimulated by an allergen. Antigens from microbes stimulate antigen-specific B-cells to produce antibodies. Some of these (IgE) bind to mast cells, which becomes sensitized. After a second contact with the same allergen, the sensitized mast cells are triggered to release inflammatory mediators (like histamine) from its granules. In association with complement (which also activates mast cells via C3a and C5a) the mediators induce local inflammation facilitating the arrival of phagocytes and more plasma enzyme system molecules (Roitt, Immunology 1985 page 1.8, 14.1, 19.6–11). Mast cells play an important role in asthma and other more benign allergies. Therefore controlling mast cell function in these disorders through therapeutic intervention is desirable. Many drugs have been developed including small compound drugs and antibody therapies. New candidate target genes require target validation using primary human mast cells. Efficient gene transfer into mast cells is crucial and limiting.

REPORTED DEVELOPMENTS

It has been shown by Wickham et al that poor T-cell transduction is due to lacking of both the primary Ad2–Ad5 receptor, used in attachment, and the secondary Ad receptor, which mediates entry of most adenovirus serotypes. Increasing adenoviral gene transfer into human T-lymphocytes has been achieved through the use of bispecific antibodies. Bispecific antibodies consisting of an antibody against adenoviral knob and an antibody against the pantropic marker CD3 have been used to transfer genes into resting T-lymphocytes (Wickham et al, 1997). The efficiencies that were achieved varied between 25 and 90%. The production of bispecific antibodies is done using chemical coupling methods such as succinimidyl-3-(2-pyridyldithiol)-propionate (SPDP) as a cross lining agent. Even though coupling of antibodies is technically feasible, these methods are prone to be difficult in terms of reproducibility. Furthermore, every time a transduction is done the adenoviral vector needs to be pre-incubated with the bi-specific antibodies to generate the targeted adenoviral vector, creating another variable in the procedure. Also important is the fact that anti-CD3 monoclonal antibodies activate the T-cell receptor activation signal (normally provided by antigen and antigen-presenting cells). The anti-CD3 monoclonal antibody most commonly used is OKT.sub.3, which is commercially available from Ortho Pharmaceuticals.

The present invention was made in the course of the manipulation of adenoviral vectors to obtain efficient gene transfer into T-lymphocytes, and in particular human T-lymphocytes.

SUMMARY OF THE INVENTION

The present invention provides functional genomics and gene therapy methods, using gene delivery vehicles provided with a tissue tropism for human T-lymphocytes, mast cells and B cells, useful in applications where primary T-lymphocytes, mast cells or B cells comprise the target cell type.

In one aspect, the present invention relates to a method of introducing an expressible non-viral nucleic acid sequence into a cell having a common non-universal binding receptor and selected from T lymphocytes, B-, and mast cells, comprising contacting said cell with a viral vector comprising a recombinant nucleic acid sequence containing sequence for said expressible non-viral nucleic acid and comprising a modified viral coat consisting of native viral coat proteins and modified coat protein containing adenoviral amino acid sequence from an adenoviral serotype 35 or 51 fibre protein, wherein said adenoviral sequence of said modified protein is a ligand for said binding receptor.

In another aspect, the present invention relates to a method of introducing an expressible non-viral nucleic acid sequence into a cell having a common non-universal binding receptor and selected from T lymphocytes, B-, and mast cells, comprising contacting said cell with a viral vector comprising a recombinant adenoviral nucleic acid sequence containing sequence for said expressible non-viral nucleic acid and for sequence coding for a viral capsid consisting of native adenoviral capsid proteins and modified capsid protein containing amino acid sequence from an adenoviral serotype other than the serotype of said native capsid proteins, wherein said modified protein is a ligand for said binding receptor.

In a further aspect, the present invention relates to a method for transducing a cell selected from the group consisting of T lymphocytes, B cells, and mast cells comprising contacting said cells with an adenovirus particle comprising a non-adenovirus nucleic acid sequence and a chimeric capsid protein comprising amino acid sequence derived from at least two adenovirus serotypes, wherein said particle has a greater tropism for said cells relative to at least one of the adenovirus serotypes comprising said chimeric capsid protein.

The present invention also relates to a transduced cell selected from the group consisting of T lymphocytes, B-, and mast cells and comprising a replication incompetent recombinant adenoviral nucleic acid sequence containing sequence for an expressible non-viral nucleic acid and coding for a viral capsid consisting of native adenoviral capsid proteins and modified capsid protein containing amino acid sequence from an adenoviral serotype other than said native capsid proteins, wherein said modified protein is a ligand for a binding receptor on said cell.

The present invention also relates to a method for ex vivo transduction of a population of cells comprising (a) obtaining from a mammal said population of cells selected from the group consisting of T lymphocytes, B cells and/or mast cells, and (b) transducing said cell population in vitro with a replication incompetent viral vector comprising a recombinant adenoviral nucleic acid sequence containing sequence for said expressible non-viral nucleic acid and for a viral capsid consisting of native adenoviral capsid proteins and modified capsid protein containing amino acid sequence from an adenoviral serotype other than said native capsid proteins, wherein said modified protein is a ligand for a binding receptor on said cells.

The present invention further relates to a method of administering to a human or other mammalian animal subject a population of cells genetically modified ex vivo with an expressible recombinant nucleic acid, comprising (a) obtaining from said subject said population of cells selected from the group consisting of T lymphocytes, B cells, mast cells and/or dendritic cells, (b) contacting said cell population with a replication incompetent viral vector comprising a recombinant adenoviral nucleic acid sequence containing sequence for said expressible non-viral nucleic acid and for a viral capsid consisting of native adenoviral capsid proteins and modified capsid protein containing amino acid sequence from an adenoviral serotype other than said native capsid proteins, wherein said modified protein is a ligand for a binding receptor on said cells, thereby obtaining a transduced population of cells; and (c) introducing said transduced cells into said subject.

The present invention also relates to a method for identifying the function of a subject nucleic acid in hematopoietic cells, comprising (a) contacting a first population of cells selected from the group consisting of T-lymphocytes, B-, and mast cells with a replication incompetent viral vector comprising a recombinant adenoviral nucleic acid sequence containing an expressible sequence for said subject nucleic acid and for a viral capsid consisting of native adenoviral capsid proteins and modified capsid protein containing amino acid sequence from an adenoviral serotype other than said native capsid proteins, wherein said modified protein is a ligand for binding receptor on said cell, thereby transducing said cell population; and (b)observing a change in the function of said transduced cell population.

Generally, it is an object of the invention to provide an improved means and method for providing a desired nucleotide sequence to a target cell, and in particular to a T-lymphocyte, mast cell or B cell. It is an object of the current invention to provide materials and methods to overcome the limitations of the prior art adenoviral vectors. In a broad sense, the invention provides methods using adenoviral viruses, derived in whole or in part from adenovirus serotypes different from Ad5, combining genes of adenovirus serotypes with preferred characteristics in a chimaeric vector to give rise to a vector better suited for specific applications. Preferred characteristics include, but are not limited to, improved infection of a specific target cell, reduced infection of non-target cells, improved stability of the virus, reduced toxicity to target cells, reduced neutralization in humans or animals, reduced or increased CTL response in humans or animals, better and/or prolonged transgene expression, increased penetration capacity in tissues, improved yields in packaging cell lines, etc.

Further aspects of the present invention are described in more detail below.

BRIEF DESCRIPTION OF THE DRAWINGS

FIGS. 4A (SEQ ID NO.: 1) and 4B (SEQ ID NO.: 2) shows amino acid-sequences of the fiber proteins of adenovirus serotypes 35 and 51. Bold letters represent part of the tail of adenovirus type 5. At the end of the sequence the stop codon of the fiber is presented by a dot.

FIG. 8 is an analysis of transduced T-lymphocytes. The T-cells were harvested and stained for CD3 (-PE) expression, 48 hours after transduction, followed by flow cytometry analysis to determine the percentage of $CD3^+eGFP^+$ T-lymphocytes. Percentages given, are average percentages of $eGFP^+$ cells in the $CD3^+$ cell-population (average of two wells). Uninfected (a), Ad5\dE1.fib51.pAdApt/eGFP crude MOI 703 (b), Ad5\dE1.fib51 .pAdApt/eGFP pure MOI 2500 (c).

FIG. 10 shows pictures taken with an inverted fluorescence microscope 72 hours after transduction of mature (L16) and immature (BW) mast cells as described in Example 4. Mature mast cells transduced with Ad5\dE1.fib51.pAdApt/eGFP crude MOI 250, 1000 and 2500 (A). Immature mast cells transduced with Ad5\dE1.fib51.pAdApt/eGFP crude MOI 250, 1000 and 2500 (B).

FIGS. 12A and B show flow cytometry results of transduced mature and immature mast cells. A flow cytometer was used to determine the percentage of $eGFP^+$ cells for mature mast cells (A) and immature mast cells (B). The mast cells were harvested 96 hours after transduction, followed by flow cytometry analysis to determine the percentage of $eGFP^+$ mast cells. Cr stands for crude lysate adenoviral vectors and p stands for purified adenoviral vectors. MOI is in VP/cell.

FIGS. 13A and B show the β-hexoseaminidase assay results of transduced mature and immature mast cells. The assay was performed 48 hours after transduction of the mature (L20) mast cells (A) and immature (BW) mast cells (B). Absorbance was read at 405 nm. Figures 250, 1000 and 2500 stand for the MOIs used in VP/cell, buffer stands for untreated cells, flask stand for cells that were taken freshly from a culture-flask before performing the assay and TNP-1 and-10 stand for the concentration 1 and 10 ng/ml antigen (TNP) added during the assay.

DETAILED DESCRIPTION

Figure 1:
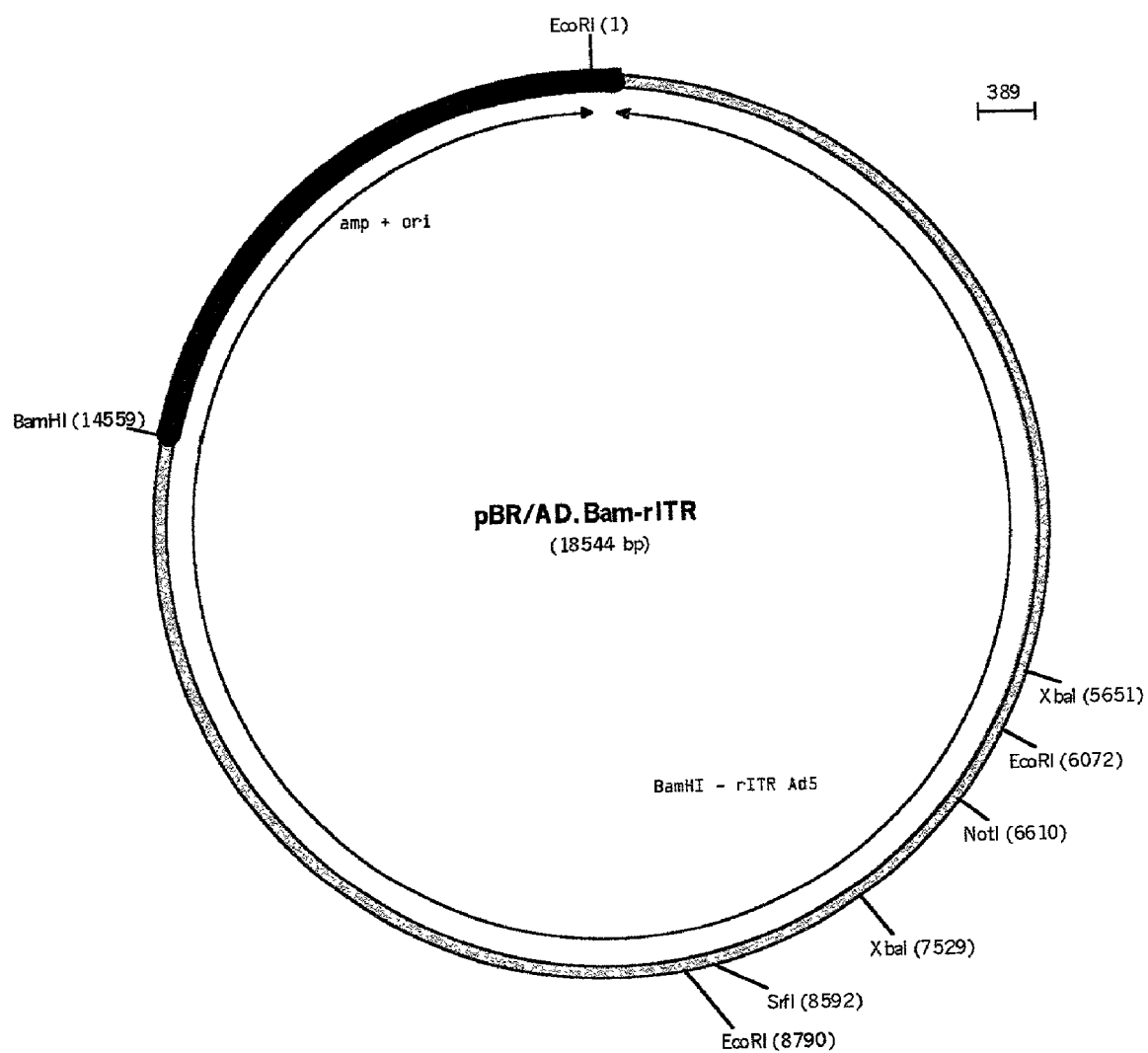
FIG. 1 is a schematic drawing of the pBr/Ad.Bam-rITR construct used in Example 1.

A "viral vector" as referred to herein is in the form of a viral particle comprising a viral coat (e.g. an envelope or a capsid) in which is contained/packaged a nucleic acid that encodes said desired nucleotide sequence, and usually also (at least part of) the viral genome.

"Tropism" as used herein is intended to mean the ability or affinity of a particular viral particle to bind to a particular cell type or types relative to other cell types. An increased tropism means a greater affinity or ability to bind to a cell type or types, while a decreased tropism means a lesser affinity or ability to bind to a cell type or types. A limited tropism means an ability to bind to a subset of cells as opposed to a broad or general tropism that means the ability to bind to a large number of different cell types or to all cell types. A particular tropism means the ability of a particular virus to bind to a particular subset of cell types. A preferred limited tropism is the tropism for nuclear hematopoietic cells, and most particularly a tropism for T-lymphocytes, B cells and mast cells.

The present invention uses viral vectors that have increased tropism for T-lymphocytes, mast cells or B cells, i.e. compared to the commonly used adenoviral vectors Ad2 and Ad5, and that still has all the advantages of (Ad2 or Ad5) adenoviral vectors. Generally, the invention uses a (chimaeric) virus or virus particle that is suitable for use as a viral vector, and that has been provided with an altered/modified viral coat that confers upon said virus particle increased tropism for T-lymphocytes, B cells or mast cells.

The term "(viral) coat" as used herein (also) encompasses viral capsid(s) and/or viral envelope(s). Accordingly, the term "coat protein(s)" as used herein comprises any and all proteins that (together) constitute the viral coat, capsid and/or envelope, including but not limited to any fiber(s), penton(s) or hexon(s). Usually, in the invention, the use of a viral particle that comprises a capsid—such as an adenovirus particle—will be preferred.

According to the invention, any one or more of the proteins which form the viral coat (e.g. capsid or envelope) is modified, altered and/or replaced (e.g. essentially fully or in part) by one or more corresponding coat proteins derived from another virus, to provide the chimaeric virus particle with increased tropism for a T-lymphocyte, B cell or a mast cell as described herein.

In the invention, the (native) viral particle which is provided with the increased tropism for T-lymphocytes, B cells or mast cells is (derived from) any virus particle known per se, including but not limited to retrovirus, lentivirus, alphavirus, adeno-associated virus, or influenza virus. Preferably, said viral particle will be derived from an adenovirus.

When in said native viral particle, one or more coat protein(s) and/or a fiber—or any part(s) of such coat proteins or fiber—is replaced by one or more coat proteins and/or a fiber from another virus, said one or more coat proteins and/or said fiber—or said part(s) thereof—may derived from any one or more suitable (viral) sources, including but not limited to adenovirus, retrovirus, adeno associated virus (AAV), lentivirus, alphavirus or influenza virus. Preferably, however, said coat protein(s) and/or fiber—or said part(s) thereof—will be derived from an adenovirus.

Accordingly, the coat protein(s) and/or fiber that are used to replace the coat protein(s) and/or fiber in the native viral particle is derived from a virus (particle) that belongs to a different type or species than said native virus particle, for instance when a fiber or another coat protein of an adenovirus is build into a retrovirus or a lentivirus.

Also, the coat protein(s) and/or fiber that are used to replace the coat protein(s) and/or fiber in the native viral particle is derived from virus (particle) that belongs to a different subgroup than the subgroup of the native virus particle, for instance when a fiber or another coat protein from an adenovirus of subgroup C is build into an adenovirus of subgroup B.

Also, the coat protein(s) and/or fiber that are used to replace the coat protein(s) and/or fiber in the native viral particle is derived from a virus (particle) from a different subtype or serotype than the native viral particle, for instance when a fiber or another coat protein from an adenovirus from subtype Ad35 or Ad51 is build into an adenovirus particle of subtype Ad2 or Ad5 (in which Ad35/Ad51 and Ad2/Ad5, respectively, in this case also belong to different subgroups of adenovirus).

Preferably, in the practice of the invention, one or more of the proteins which form the viral coat will be (essentially fully) replaced by one or more coat proteins derived from another (type, subtype or serotype of) virus to provide the chimaeric virus particle with increased tropism for a T-lymphocyte, B cell or a mast cell as described herein.

In particular, the at least one coat protein that is altered, modified and/or replaced (e.g. essentially fully and/or in part) so as to provide said chimaeric virus particle with increased tropism for a T-lymphocyte, B cell or mast cell will be at least one fiber. Even more in particular, said at least one fiber will be replaced by a fiber derived from another (type, subtype or serotype of) virus so as to provide the chimaeric virus particle with increased tropism for a T-lymphocyte, B cell or mast cell as described herein.

In particular, said virus particle is provided with a coat comprising one or more coat proteins, at least one of which is altered, is modified and/or is replaced by a coat protein from another (type, subtype and/or serotype of) virus, so as to confer upon said virus particle increased tropism for T-lymphocytes, B cells or mast cells, i.e. compared to the native virus particle.

In one particularly preferred embodiment of the invention, said at least one coat protein that is altered. modified and/or replaced (e.g. essentially fully or in part) will be a fiber (fibre). In this embodiment, the fiber may for instance be replaced by a fiber from another (type or subtype of) virus; or one or more parts of the amino acid sequence of the (native) fiber is replaced by one or more parts of the amino acid sequence of a fiber from another (type, subtype and/or serotype of) virus.

In particular, in the practice of invention, the chimaeric virus particle will have been derived from a "first" virus type or subtype (for example from adenovirus Ad2 or Ad5) whereas the coat protein(s)/fiber that confer(s) upon said virus particle increased tropism for T-lymphocytes will have been derived (e.g. essentially fully and/or in part) from a different, "second" virus type or subtype (such as adenovirus Ad35 or Ad51).

The chimaeric viral particles of the invention may generally be prepared starting from a genetic construct that encodes the at least one desired nucleotide sequence and that further may encode (at least part of) the chimeric coat that provides the final viral particle with increased tropism for T-lymphocytes, B cells or mast cells, as well as one or more further viral elements as further mentioned below. Generally, said preparation of the viral particles is carried out by "packaging" said genetic construct in a suitable (packaging) cell to provide said chimeric viral particle, as will be further described hereinbelow. Accordingly, it is a further object of the invention is to provide such genetic constructs that is packaged/used to provide a chimeric viral particle of the invention.

Thus, in a first aspect, the invention provides a chimaeric virus particle suitable for use as a vehicle for delivering at least one desired nucleotide sequence to a target cell, and in particular to a T-lymphocyte, B cell or mast cell; which chimaeric virus particle comprises a (viral) coat, in which said coat is different from the coat that occurs in the native virus (particle), i.e. the virus (particle) from which the chimaeric virus particle has been derived, and provides said virus particle with increased tropism for a T-lymphocyte, B cell or mast cell (e.g. compared to the native virus particle).

In particular, the invention provides a chimaeric virus particle suitable for use as a vehicle for delivering at least one desired nucleotide sequence to a target cell, and in particular to a T-lymphocyte, B cell or mast cell; which chimaeric virus particle comprises a coat, which coat comprises one or more coat proteins, at least one of which is different from the (corresponding) coat protein that occurs in the native virus (particle), and provides said chimaeric virus particle with increased tropism for a T-lymphocyte, B cell or mast cell (e.g. compared to the native virus particle).

According to this latter embodiment, the invention provides a chimaeric virus particle suitable for use as a vehicle for delivering at least one desired nucleotide sequence to a target cell, and in particular to a T-lymphocyte, B cell or mast cell; which chimaeric virus particle comprises a coat, which coat comprises at least one fiber, in which said fiber is different from the fiber that occurs in the native virus (particle), and provides said chimaeric virus particle with increased tropism for a T-lymphocyte, B cell or mast cell (e.g. compared to the native virus particle).

It is also possible to provide the native virus particle with increased tropism for T-lymphocytes, B cells or mast cells by altering and/or modifying the at least one coat protein, e.g. by replacing one or more of the native coat proteins, and in particular by replacing the native fiber, with one or more coat proteins and/or a fiber the amino acid sequence of which has been altered and/or modified, such that the resulting altered/modified coat protein(s) or fiber provides the virus particle with increased tropism for T lymphocytes, B cells or mast cells. Alterations/modifications may for instance comprise substitution, addition, deletion and/or insertion of one or more amino acid residues, compared to the native amino acid sequence of the coat protein(s) and/or fiber.

For example, an analog, variant, mutant, part and/or fragment of a naturally occurring coat protein and/or fiber is used, provided that such an analog, variant, mutant, part and/or fragment is different from the coat protein/fiber that occurs in the native virus (particle); and provided that such an analog, variant, mutant, part and/or fragment is capable of providing said chimaeric virus particle with increased tropism for a T-lymphocyte, B cell or mast cell, i.e. compared to the native virus particle.

For example, such an analog, etc., is derived from a virus (particle) of a different type/species, from a virus (particle) of a different subgroup, or from a virus (particle) of a different sub- or serotype. In addition, such an analog, etc., is derived from the coat protein and/or fiber that natively occur in the virus (particle) from which the chimaeric virus particle has been derived.

A (native) coat protein, such as a (native) fiber, is modified in that at least one part of the amino acid sequence of said coat protein has been replaced by at least one amino acid sequence derived from at least one other coat protein (and usually a corresponding coat protein) or fiber—i.e. from at least one other virus—so as to provide a chimaeric virus particle with increased tropism for T-lymphocytes, B cells or mast cells.

One specific non-limiting example thereof is the use of a fiber that is comprised of amino acid sequences derived from two or more different viruses—e.g. from two or more different adenovirus subtypes/serotypes, which may (also) include one or more sequences derived from the native adenovirus—which amino acid sequences together form the fiber that provides the viral vector with increased tropism for T-lymphocytes, B cells or mast cells, as described above.

The chimaeric virus particle of the invention preferably has increased tropism for at least one (type of) T-lymphocyte, B cell or mast cell, in particular for at least one (type of) T-lymphocyte derived from at least one species of animal, and more in particular for at least one (type of) T-lymphocyte or mast cell derived from at least one species of mammal, including but not limited to T-lymphocytes, B cells or mast cells derived from such mammals as human beings, rats, monkeys, horses and bovine.

In one particularly preferred embodiment, the chimaeric virus particle of the invention has increased tropism for at least one (type of) T-lymphocyte derived from a human being.

According to another embodiment, the chimaeric virus particle of the present invention is suitable for use as a vehicle for delivering at least one desired nucleotide to a mast cell.

It should however be noted that, although the chimaeric virus particles of the invention have improved tropism for T-lymphocytes, B cells or mast cells—and thus are most preferably used to provide the at least one desired nucleotide sequence to a T-lymphocyte, B cell or mast cell—the chimaeric virus particle of the invention may in its broadest sense be used to deliver the desired nucleotide sequence to any desired target cell. These may include, but are not limited to, cells that are kept in vitro (e.g. in culture, for instance for functional genomics applications as described herein) or is cells in vivo, e.g. a cell present in (a tissue or organ of) an animal, and in particular in a mammal including but not limited to a human being (e.g. for gene therapy applications).

These may include target cells such as, but not limited to T-lymphocytes (and/or subtypes thereof, including but not limited to $CD3^+$ cells, $CD3^+CD4^+CD8^+$, $CD3^+CD69^+$, $CD69^+$, $CD3^+CD4^+CD8^-CD69^+$, $CD3^+CD4^+CD8^{-CD}69^-$, $CD3^+CD4^-CD8^+CD69^+$ or $CD3^+CD4^{-CD}8^+CD69^-$ cells), B-lymphocytes, dendritic cells, and/or $CD34^+$-cells. It may in particular include those cells which carry receptors and/or other proteins on their cell surface that are functionally equivalent to the receptors that are present on the cell surface of the T-lymphocytes, B cells or mast cells and that are "recognized" by the coat protein/fiber used herein. The target cells may therefore also consist of mast cells, which can be cultured from CD34+ progenitors.

Preferably, however, the target cell is a T-lymphocyte, in particular a T-lymphocyte of a mammal, and more in particular a T-lymphocyte of a human being, which may again be present in vitro (e.g. in a culture of T-lymphocytes) or in vivo (e.g. in the body of such a animal, mammal and/or human being).

According to another preferred embodiment, the target cell in the present invention preferably consists of a mast cell.

Mast cells are bone marrow-derived resident tissue cells. They develop in situ from progenitor cells found in the peripheral blood that migrate into various tissues and differentiate into mature mast cells under the influence of microenvironmental factors. As a result, mast cells can be found in a wide variety of tissues including the skin, connective tissues of various organs, and mucosal epithelial tissue of the respiratory, genitourinary, and digestive tract. Mast cells have large numbers of cytoplasmic granules containing histamine and other pharmacologically active substances. Therefore, mast cells play a pivotal role in the pathophysiology of acute allergic reactions. Mast cells is obtained by any method known in the art, including, but not limited to the preparation methods described hereunder such as isolation from biological tissues or fluids, or in vitro growth from tissue cultures.

Mast cells are harvested from human lung or skin through a series of tissue digestions and a long isolation procedure. Alternatively, human mast cells may also be grown in vitro from hematopoietic progenitors found in bone marrow, peripheral blood, umbilical cord blood, and fetal liver, when maintained in liquid culture in the presence of recombinant human (rh) stem cell factor (SCF). Yet another alternative is to grow human mast cells in vitro from cord blood progenitors, such as CD34+ progenitor cells, cultured in the presence of rhSCF, rhIL-6 and prostaglandin (PG)-E2. Yet another method consists of growing mast cells from embryonic stem cells.

As mentioned above, the term "virus (particle)" as used herein indicates a particle that at least comprises a coat (meaning e.g. a capsid or an envelope) and at least one nucleic acid packaged within said coat, which nucleic acid encodes the nucleotide sequence to be provided to the target cell and preferably also (at least part of) the viral genome.

Preferably, the at least one nucleotide sequence to be provided to the target cell is present in the viral particle—i.e. in the nucleic acid packaged in said viral particle—in such a way that, upon infection of the target cell with the chimaeric virus particle, said at least one nucleotide sequence is transferred to the target cell, e.g. in a manner that allows for expression of said at least one nucleotide sequence in said target cell, and/or otherwise allows said at least one nucleotide sequence to provide and/or carry out its (intended) biological function in the target cell.

Optionally, a chimaeric virus particle of the invention may also include one or more further viral elements known per se, including but not limited to one or more core proteins; one or more viral protease(s),one or more proteins necessary for the assembly of the coat and shut-down of host protein translation, one or more DNA binding proteins, DNA- or RNA polymerases, and Reverse transcriptases.

In this respect, the chimaeric virus particle is preferably such that it is capable of providing the at least one desired nucleotide sequence to the target cell. Generally, this means that said chimaeric virus particle (and/or the nucleic acid packaged therein) should at least contain—i.e. besides the one or more proteins that form the coat—one or more, and preferably all, of the viral elements required for providing said at least one desired nucleotide sequence to the target cell.

Also, the chimaeric virus particle should preferably be such that it is incapable of independent replication. Such virus particles and their preparation will be known per se to the skilled person and/or will be as further described herein. For instance, for RCA-free adenovirus vectors and their production reference is generally made to International Application WO 97/00326.

The at least one desired nucleotide sequence is any nucleotide sequence, either of known biological function, or of unknown biological function (e.g. when said function is to be determined, for instance as part of a functional genomics program). As such, the desired nucleotide sequence may encode an amino acid sequence (e.g. a protein such as an enzyme, a transporter, a kinase, phosphatase, a transcription factor or polypeptide) or an RNA sequence (e.g. mRNA, rRNA or tRNA); and/or may for instance be a cDNA, genomic DNA, previously cloned DNA, gene, EST, synthetic oligonucleotide, random sequence, antisense nucleic acid or genetic suppressor element.

In a particularly preferred embodiment of the invention, the chimaeric virus particle is or has been derived from an adenovirus (particle), i.e. to provide an adenoviral vector.

According to this embodiment, the invention thus provides a chimaeric virus particle, derived from an adenovirus (particle) and suitable for use as a vehicle for delivering at least one desired nucleotide sequence to a target cell, and in particular to a T-lymphocyte, B cell or mast cell; which chimaeric virus particle comprises a capsid that is different from the capsid that occurs in the native adenovirus (particle), provides said virus particle with increased tropism for a T-lymphocyte, B cell or mast cell(e.g. compared to the native adenovirus particle).

In particular, the invention provides a chimaeric virus particle derived from an adenovirus (particle) and suitable for use as a vehicle for delivering at least one desired nucleotide sequence to a target cell, and in particular to a T-lymphocyte, B cell or mast cell; which chimaeric virus particle comprises a capsid comprising one or more capsid proteins, at least one of which is different from the (corresponding) capsid protein that occurs in the native adenovirus (particle); and provides said virus particle with increased tropism for a T-lymphocyte, B cell or mast cell (e.g. compared to the native adenovirus particle).

Preferably, the at least one capsid protein that provides said chimaeric adenovirus particle with increased tropism for a T-lymphocyte, B cell or mast cell is a fiber, a hexon, a penton, any combination thereof or a mutant derived thereof. Most preferably, the at least one capsid protein that is altered, modified and/or replaced to provide said chimaeric virus particle with increased tropism for a T-lymphocyte, B cell or mast cell, is a fiber. For instance, said fiber is replaced by a fiber derived from another adenovirus (e.g. from another subgroup and/or another subtype or serotype).

Thus, in another aspect, the invention thus provides a chimaeric virus particle derived from an adenovirus (particle) and suitable for use as a vehicle for delivering at least one desired nucleotide sequence to a target cell, and in particular to a T-lymphocyte, B cell or mast cell; which chimaeric virus particle comprises a capsid, which capsid comprises at least a fiber, in which said fiber is different from the fiber that occurs in the native adenovirus (particle), provides said virus particle with increased tropism for a T-lymphocyte, B cell or mast cell (e.g. compared to the native adenovirus particle).

Even more preferably, the at least one capsid protein or fiber that provides said chimaeric adenovirus particle with increased tropism for T-lymphocytes, B cells or mast cells is also derived from an adenovirus. For instance, the at least one capsid protein and/or fiber is derived from a "first" sub- or serotype of adenovirus, whereas the at least one capsid protein or fiber may have been derived from a different, "second" sub- or serotype of adenovirus; in which these "first" and "second" sub- or serotypes belong to the same or different subgroups.

A pertinent listing of human adenovirus subtypes is given hereinbelow. It should be noted that the invention in its broadest sense is not limited to the use of (adeno)virus particles and/or (adeno)viral coat proteins of human (adeno) viruses. For instance, also particles and/or coat proteins of non-human adenoviruses is used:

Human Adenoviruses
   Subgroup A: Ad12, Ad18, Ad31
   Subgroup B1: Ad3, Ad7, Ad16, Ad21, Ad51,
   Subgroup B2: Ad11, Ad14, Ad34, Ad35,
   Subgroup C: Ad1, Ad2, Ad5, Ad6,
   Subgroup D: Ad8, Ad9, Ad10, Ad13, Ad15, Ad17, Ad19, Ad20, Ad22–30, Ad32, Ad33, Ad36–39, Ad42–50
   Subgroup E: Ad4,
   Subgroup F: Ad40, Ad41.

Preferably, the first adenovirus (particle)—i.e. to which the capsid protein(s)/fiber is provided to afford a chimaeric adenovirus particle of the invention—is an adenovirus of subgroup C, and more preferably Ad2 or Ad5, with Ad5 being particularly preferred. Also, preferably, the adenovirus from which the capsid protein/fiber is derived from is an adenovirus of subgroup B, and more preferably Ad35 or Ad51. With respect to adenovirus serotype "Ad51" as referred to herein, it should be noted that said serotype has been described in the article by de Jong et al., Journal of Clinical Microbiology, December 1999, p. 3940–3945, as serotype "Ad 50" (which is also described in the de Jong reference as belonging to subgroup B1). In this respect, it should further be noted that the adenovirus serotype referred to as "Ad 51" in the "De Jong"-reference (which is described as belonging to subgroup D) is herein referred to as adenovirus serotype "Ad 50".

Thus, in one preferred embodiment, the chimaeric adenovirus particle of the invention is an adenovirus particle of the sub-or serotype Ad5 at least provided with at least one capsid protein, and in particular the fiber, from an adenovirus of sub -or serotype Ad35 or Ad51.

In another preferred embodiment, the chimaeric adenovirus particle of the invention is an adenovirus particle of the sub- or serotype Ad2 at least provided with at least one capsid protein, and in particular the fiber, from an adenovirus of sub- or serotype Ad35 or Ad51.

Alternatively, an analog, variant, mutant, part and/or fragment of a naturally occurring adenoviral capsid protein and/or fiber is used, which may again have been derived from an adenovirus of a different subgroup, subtype and/or serotype than the adenovirus (particle) from which the chimaeric adenovirus particle has been derived, provided that such an analog, variant, mutant, part and/or fragment is capable of providing said chimaeric adenovirus particle with increased tropism for a T-lymphocyte, B cell or mast cell, i.e. compared to the native adenovirus particle.

In addition, such analogs, variants, mutants, parts and/or fragments may also have been derived from the capsid protein and/or fiber that natively occurs in the adenovirus (particle) from which the chimaeric adenovirus particle has been derived, again provided that such an analog, variant, mutant, part or fragment is different from the capsid protein that occurs in the native adenovirus (particle); and provided that such an analog, variant, mutant, part or fragment is capable of providing said chimaeric adenovirus particle with increased tropism for a T-lymphocyte, B cell or mast cell compared to the native adenovirus particle.

Thus, according to one specific embodiment, the invention provides a chimaeric virus particle derived from a first sub- or serotype of adenovirus and suitable for use as a vehicle for delivering at least one desired nucleotide sequence to a target cell, and in particular to a T-lymphocyte, B cell or mast cell; which chimaeric virus particle comprises a capsid comprising one or more capsid proteins, in which at least one capsid protein is derived from a sub- or serotype of adenovirus different from said first sub- or serotype; and in which said at least one capsid protein provides said virus particle with increased tropism for a T-lymphocyte, B cell or mast cell (e.g. compared to a native adenovirus particle of said first sub- or serotype).

More in particular, the invention provides a chimaeric virus particle derived from a first sub- or serotype of adenovirus and suitable for use as a vehicle for delivering at least one desired nucleotide sequence to a target cell, and in particular to a T-lymphocyte, B cell or mast cell; which chimaeric virus particle comprises a capsid, which capsid comprises at least a fiber, in which said fiber is derived from a sub- or serotype of adenovirus different from said first sub-or serotype; and in which said fiber provides said chimaeric virus particle with increased tropism for a T-lymphocyte, B cell or mast cell (e.g. compared to a native adenovirus particle of said first subtype).

According to one particular embodiment, the invention provides a chimaeric virus particle derived from a first sub- or serotype of adenovirus and suitable for use as a vehicle for delivering at least one desired nucleotide sequence to a target cell, and in particular to a T-lymphocyte; which chimaeric virus particle comprises a capsid, which capsid comprises a fiber and one or more further capsid protein, in which at least said fiber is derived from a sub- or serotype of adenovirus different from said first sub- or serotype, said fiber provides said chimaeric virus particle with increased tropism for a T-lymphocyte (e.g. compared to a native adenovirus particle of said first sub- or serotype), and in which optionally, at least one of the further capsid proteins is derived from the first sub- or serotype of adenovirus.

In this embodiment of the invention, besides the fiber, also one or more further capsid proteins may also have been derived from the "second" adenovirus, provided that at least one of the capsid proteins is (still) derived from the "first" adenovirus.

Also, more generally, in all the above aspects and embodiments of the invention, it is not excluded that, besides the coat protein(s)/fiber, the chimaeric virus particle of the invention in addition contains one or more further viral elements (e.g. as listed above)—and/or nucleotide sequences encoding such viral elements—that have been derived from the "second" virus (particle).

Preferably, in the invention, the "first" adenovirus (particle)—i.e. to which the capsid protein(s)/fiber is provided to afford a chimaeric adenovirus particle of the invention—is an adenovirus of subgroup C, and more preferably Ad2 or Ad5, with Ad5 being particularly preferred.

Also, preferably, the "second" adenovirus—i.e. from which the capsid protein/fiber is derived—is an adenovirus of subgroup B, and more preferably Ad35 or Ad51.

Thus, in one particularly preferred embodiment, the chimaeric adenovirus particle of the invention is an adenovirus particle of the sub- or serotype Ad5 at least provided with at least one capsid protein, and in particular the fiber, from an adenovirus of sub- or serotype Ad35 or Ad51.

In another particularly preferred embodiment, the chimaeric adenovirus particle of the invention is an adenovirus particle of the sub- or serotype Ad2 at least provided with at least one capsid protein, and in particular the fiber, from an adenovirus of sub- or serotype Ad35 or Ad51.

For instance, in the invention, the fiber protein of adenovirus Ad35 (with the amino acid sequence shown in FIG. 4A and SEQ ID NO:1) and/or the fiber protein of adenovirus Ad51 (with the amino acid sequence shown in FIG. 4B and SEQ ID NO: 2) is used to provide the "first" adenovirus (particle), and in particular Ad2 and/or Ad5, with increased tropism for T-lymphocytes.

Alternatively, a mutant, analog, variant, part or fragment of the amino acid sequence of SEQ ID NO:1 and/or SEQ ID NO:2 is used, e.g. obtained by substitution, deletion, addition and/or insertion of one or more amino acid residues into or from the sequence of SEQ ID NO:1 and/or SEQ ID NO:2.

Preferably such a mutant, analog, variant, part or fragment still has a degree of amino acid homology with SEQ ID NO:1 and/or SEQ ID NO:2 of 50%, preferably at least 70%, more preferably at least 80%, even more preferably at least 90%, with the sequence of SEQ ID NO:1 and/or SEQ ID NO:2; in which the percentage amino acid homology is calculated by dividing the total number of amino acid residues that are identical to the amino acid residues on the corresponding amino acid position of SEQ ID NO:1 (or SEQ ID NO:2 by the total number of amino acid residues of SEQ ID NO:1 (or SEQ ID NO:2); and multiplying by 100%, each substitution, insertion, deletion or addition of an amino acid is considered an alteration at a single amino acid position; and "conservative" amino acid substitutions are taken into account. Alternatively, the amount of amino acid homology is determined using a suitable computer algorithm such as BLAST or PC-GENE at standard settings.

Also, instead of a such a synthetic mutant, analog, variant, part or fragment, also a naturally occurring analog or variant of the amino acid sequence of SEQ ID NO:1 and/or SEQ ID NO:2 is used, i.e. derived from a sub- or serotype of adenovirus different from Ad35 or Ad51. Again, such a natural analog or variant preferably has a degree of amino acid homology (calculated as set out above) with SEQ ID NO:1 and/or SEQ ID NO:2 of 50%, preferably at least 70%, more preferably at least 80%, even more preferably at least 90%.

Also, preferably, the capsid protein/fiber is such that it provides the chimaeric virus particle of the invention, and in particular the chimaeric adenovirus particle of the invention, with a tropism for (at least one type of) T-lymphocytes, B cells or mast cells (e.g. of at least one species of animal (mammal); and in particular from a human being), that is higher than the tropism of native Ad2 and/or Ad5 adenovirus.

More in particular, the capsid protein/fiber is such that it provides the chimaeric virus particle of the invention, and in particular the chimaeric adenovirus particle of the invention, with a tropism for (at least one type of) T-lymphocytes, as determined by the test described in Example 2 involving the introduction of eGFP into a T-lymphocyte, of at least 10%, preferably at least 30%, and in particular 40% or more. (By comparison, in said test, native Ad2 and Ad5 provide no more than 5%).

In yet another aspect, the invention relates to the use of a chimaeric virus particle/viral vector as described above in providing at least one desired nucleotide sequence to a target cell.

The invention also relates to a genetic construct that is used for providing a chimaeric virus particle/viral vector as described above. Usually, such a construct will be in the form of a nucleic acid (e.g. a DNA or RNA, and preferably a DNA) that encodes (at least part of) the genome of the chimaeric viral particle, and in particular (at least part of) the viral coat. Into said genetic construct may also be or have been inserted therein the one or more desired nucleotide sequences that are to be provided to the target cell.

The genetic construct is preferably such that it is packaged in a suitable cell—such as a cell or a packaging cell line—so as to form a chimeric viral particle as described above, said particle at least comprising a viral coat with packaged therein a nucleotide sequence (e.g. encoding the viral genome and the at least one nucleotide sequence to be provided to the target cell).

When such a genetic construct encodes a chimeric adenovirus particle as described above, it may in particular be essentially as described in the international applications WO 97/00326 and/or PCT/NL/00367, which applications describe a range of E1-deleted adenovirus vectors that can be packaged and amplified using a suitable E1-complementing cell line, and optionally a suitable helper plasmid.

Generally, such a construct will at least contain, in an operable configuration, an expression cassette containing the one or more nucleotide sequences to be provided to the target cell, at least a left hand inverted terminal repeat, a packaging signal, and will essentially contain no E1 region sequences.

The constructs is used to transfect/transduce a suitable cell or cell line, such as an E1-complementing cell line, so as to produce a chimeric viral particle of the invention. This viral particle may then be used to transfect the target cell, either in vitro or in vivo, e.g. so as to provide the intended nucleotide sequence to the target cell, e.g. for expression by/in the target cell.

All this is carried out essentially as described in the international applications WO 97/00326 and/or PCT/NL99/00367. In this respect, it should be noted that these applications generally describe a broad range of different (types or classes of) genetic constructs encoding E1-deleted adenoviral vectors, such as constructs which besides the E1-deletion also do not contain/encode E2A, E2B, E3 and/or E4 region sequences. It is envisaged that the genetic constructs of the present invention encoding the chimeric (adeno)viral vectors is in one or more of these forms.

Also, the international application PCT/NL99/00367 as well as the international application in the non-prepublished U.S. provisional application 60,191,491, filed on Mar. 21, 2000 and entitled "Method for the preservation of virus particles" describes (the use of) sets, collections and/or libraries of such constructs and/or libraries of adenoviral vectors obtained by packaging such constructs, as well as uses of such libraries, e.g. in high throughput screening.

Accordingly, it is envisaged that the chimeric viral particles/vectors—and/or the genetic constructs encoding such chimeric viral particles/vectors of the invention—may also be in the form of such a set, array, collection or library, i.e. containing at least 2, preferably at least 10 different viral particles—or constructs—in which the different viral vectors—or constructs—contained within said library may for instance differ in the nucleotide sequence to be provided to the target cell that they contain; and/or in their tropism for at least one T-lymphocytes, B cells or mast cells (e.g. because each contruct/vector encodes/contains (a) different coat protein(s), leading to differences in such tropism.). Usually, a library—by which is meant a set or collection which covers the majority of, and up to essentially the entire, genome present in, and/or the majority of, and up to essentially all, cDNA's produced by a cell or organism of interest, will comprises at least 2 different sequences, e.g. between 5 and 1000 different sequences.

Such a set, array, collection or library may further be, and is produced and/or used, essentially as described in PCT/NL99/00367 and/or in the non-published US provisional application 60,191,491, filed on Mar. 21, 2000 and entitled "*Method for the preservation of virus particles*", in that said set, collection or library may for instance be associated with a suitable carrier, such as a multi-well plate. Another system for setting up an array for high throughput screening, using planar surfaces, that may be porous, is disclosed in U.S. Pat. No. 5,976,813, issued Nov. 2, 1999, and assigned to Abbott Laboratories.

Usually, said genetic construct encoding the genome of the chimaeric virus particle will have been derived from the "first" virus as meant hereinabove (e.g. Ad2 or Ad5), in which the nucleotide sequences encoding the at least one capsid protein/fiber as meant hereinabove has been removed (or at least inactivated) and replaced with (at least) a nucleotide sequence encoding (at least) the capsid protein(s)/fiber derived from the "second" virus (particle), e.g. Ad35 or Ad51, and/or with a (usually synthetic) nucleotide sequence encoding an analog, mutant, variant, part or fragment as meant hereinabove.

The invention also relates to the use of the constructs described above in providing a chimaeric virus particle as described above, i.e. by packaging said construct in a suitable cell, and in particular a suitable packaging cell, so as to provide a chimaeric virus particle of the invention. Again, this is carried out essentially as described in WO 97/00326 and/or PCT/NL99/00367. Again, this may also be carried out in a multi-well format and/or be automated.

Thus, as is seen from the above and the further disclosure herein, the invention generally provides a gene delivery vehicle having been provided with at least a cell tropism for T-lymphocytes, B cells or mast cells.

Said cell tropism is preferably being provided by a virus capsid, in which said capsid more preferably comprises protein fragments from at least two different viruses, of which viruses even more preferably at least one is an adenovirus, and in particular an adenovirus of subgroup B. Even more in particular, said subgroup B adenovirus is adenovirus 35 or 51.

Also, in the above vehicles, at least one of said protein fragments comprises a tissue tropism determining fragment of a fiber protein derived from a subgroup B adenovirus, whereas the protein fragments not derived from an adenovirus of subgroup B are preferably derived from an adenovirus of subgroup C, preferably of adenovirus 5.

The vehicle of the invention also preferably comprises a nucleic acid derived from an adenovirus, which may in particular be derived from at least two different adenoviruses. Preferably, said nucleic acid comprises at least one sequence encoding a fiber protein comprising at least a tissue or cell tropism determining fragment of a subgroup B adenovirus fiber protein, preferably of adenovirus 35 or 51.

Also, preferably, said adenovirus nucleic acid is modified such that the capacity of said adenovirus nucleic acid to replicate in a target cell has been reduced or disabled.

According to yet another aspect, said adenovirus nucleic acid is modified such that the capacity of a host immune system to mount an immune response against adenovirus proteins encoded by said adenovirus nucleic acid has been reduced or disabled.

Also, preferably, the vehicle of the invention comprises a minimal adenoviral vector or an Ad/AAV chimaeric vector (http://patent.womplex.ibm.com/cgi-bin/viewpat.cmd/WO09932647A1).

The vehicle of the invention may further comprise at least one non-adenovirus nucleic acid, which is preferably a gene selected from the group of genes encoding RANLL/ODF, T-cell receptor genes and T-cell specific transcription factors. Also, said non-adenovirus nucleic acids are nucleic acid(s) is taken from a gene collection or library. Also, when the nucleic acid forms part of such a collection or library, said nucleic acid(s) and/or vehicle(s) is arrayed and/or pooled.

The invention also relates to a cell for the production of a vehicle/vector as described above, said cell comprising means for the assembly of said vectors wherein said means includes a means for the production of an adenovirus fiber protein, wherein said fiber protein comprises at least a tissue tropism determining fragment of a subgroup B adenovirus fiber protein. Preferably, said cell is, or is derived from, a PER.C6 cell (ECACC deposit number 96022940).

The vehicle of the invention is useful as a pharmaceutical, e.g. for the treatment of cardiovascular disease, bone disorders, and/or a disease, treatable by transfer of a therapeutic nucleic acid to T-lymphocytes, B cells or mast cells.

In yet another aspect, the invention relates to an adenovirus capsid with, or provided with, a tissue tropism for cells wherein said capsid preferably comprises proteins from at least two different adenoviruses and wherein at least a cell tropism determining fragment of a fiber protein is derived from a subgroup B adenovirus, preferably of adenovirus 35 or 51.

The above adenovirus may for instance be used for the delivery of nucleic acid to T-lymphocytes, B cells or mast cells, and/or in a medicament—e.g. a gene therapy agent—for the treatment of a disease.

The invention also relates to one or more of the following constructs (further described below):

pBr/Ad.BamRΔFib, at least comprising adenovirus 5 sequences 21562–31094 and 32794–35938;

pBr/AdBamRfib51, at least comprising adenovirus 5 sequences 21562–31094 and 32794–35938, further comprising an adenovirus 51 gene encoding fiber protein;

pBr/AdBamR.pac/fib51, at least comprising adenovirus 5 sequences 21562–31094 and 32794–35938, further comprising an adenovirus 51 gene encoding fiber protein, and further comprising a unique PacI-site in the proximity of the adenovirus 5 right terminal repeat, in the non-adenovirus sequence backbone of said construct;

pWE/Ad.AflIIrITRfib51, at least comprising adenovirus 5 sequences 3534–31094 and 32794–35938, further comprising an adenovirus 51 gene encoding fiber protein;

pWE/Ad.AflIIrITRDE2Afib51, at least comprising adenovirus 5 sequences 3534–22443, 24033–31094 and 32794–35938, further comprising an adenovirus 51 gene encoding fiber protein pBr/AdBamRfib35, at least comprising adenovirus 5 sequences 21562–31094 and 32794–35938, further comprising an adenovirus 35 gene encoding fiber protein;

pBr/AdBamR.pac/fib35, at least comprising adenovirus 5 sequences 21562–31094 and 32794–35938, further comprising an adenovirus 35 gene encoding fiber protein, and further comprising a unique PacI-site in the proximity of the adenovirus 5 right terminal repeat, in the non-adenovirus sequence backbone of said construct;

pWE/Ad.AflIIrITRfib35, at least comprising adenovirus 5 sequences 3534–31094 and 32794–35938, further comprising an adenovirus 35 gene encoding fiber protein;

pWE/Ad.AflIIrITRDE2Afib35, at least comprising adenovirus 5 sequences 3534–22443, 24033–31094 and 32794–35938, further comprising an adenovirus 35 gene encoding fiber protein.

These constructs may optionally comprise at least one non-adenoviral nucleotide sequence, e.g. for delivery to a target cell as described herein.

The invention also relates to the use of a construct as generally described above, and/or to the use of one of the specific constructs described above, in or for the generation of a vehicle as mentioned above and/or an adenovirus capsid as mentioned above.

The invention also relates to the production of a vehicle as described above and/or of an adenovirus capsid as described above, which preferably at least comprises packaging a construct as described above in a suitable (packaging) cell, optionally using at least one suitable helper plasmid.

The invention also relates to the use of a vehicle as described above in or for the generation of a gene library.

The invention also relates to the use of (a nucleotide sequence encoding) a fiber protein of adenovirus 35 and/or 51 for (providing a vehicle for) the delivery of nucleic acid to T-lymphocytes, B cells or mast cells, in which said vehicle is preferably as described above.

One aspect of the present invention facilitates the combination of the low immunogenicity of some adenoviruses with the characteristics of other adenoviruses that allow efficient gene delivery. Such characteristics is a high specificity for certain host cells, a high rate of infection in certain host cells, low infection efficiency in non-target cells, etc. The invention may thus provide chimaeric adenoviruses having the useful properties of at least two adenoviruses of different serotypes.

Typically, two or more requirements from the above non-exhaustive list are required to obtain an adenovirus capable of efficiently transferring genetic material to a host cell. Therefore the present invention provides adenovirus-derived vectors, which can be used as cassettes to insert different adenoviral genes from different adenovirus serotypes at the required sites. This way one can obtain a vector capable of producing a chimaeric adenovirus, whereby of course also a gene of interest can be inserted (for instance at the site of E1 of the original adenovirus). In this manner the chimaeric adenovirus to be produced can be adapted to the requirements and needs of certain hosts in need of gene therapy for certain disorders. To enable this virus production, a packaging cell will generally be needed in order to produce a sufficient amount of safe chimaeric adenoviruses.

In one of its aspects the present invention provides adenoviral vectors comprising at least a fragment of a fiber protein. Said fiber protein is the native fiber protein of the adenoviral vector or is derived from a serotype different from the serotype the adenoviral vector is based on. In the latter case the adenoviral vector according to the invention is a chimaeric adenovirus displaying at least a fragment of the fiber protein derived from subgroup B adenoviruses, which fragment comprising at least the receptor binding sequence. Typically such a virus will be produced using a vector (typically a plasmid, a cosmid or a baculoviral vector). Such vectors are also subject of the present invention. A preferred vector is a vector that can be used to make a chimaeric recombinant virus specifically adapted to the host to be treated and the disorder to be treated.

The present invention also provides a chimaeric adenovirus based on adenovirus type 5 but having at least a fragment of the fiber sequence from adenovirus type 35 or 51, whereby the fragment of the fiber of Ad35 or Ad51 comprises the fragment of the fiber protein that is involved in binding a host cell.

The present invention also provides chimaeric adenoviral vectors that show improved infection as compared to adenoviruses from other subgroups in specific host cells for example, but not limited to, CD3$^+$ primary T-lymphocytes and mast cells of human origin. An important feature of the present invention is the means to produce the chimaeric virus. Typically, one does not want an adenovirus batch to be administered to the host cell, which contains replication competent adenovirus. In general therefore it is desired to omit a number of genes (but at least one) from the adenoviral genome on the vector encoding the chimaeric virus and to supply these genes in the genome of the cell in which the vector is brought to produce chimaeric adenovirus. Such a cell is usually called a packaging cell.

The invention thus also provides a packaging cell for producing a chimaeric adenovirus according to the invention, comprising in trans all elements necessary for adenovirus production not present on the adenoviral vector according to the invention. Typically vector and packaging cell have to be adapted to one another in that they have all the necessary elements, but that they do not have overlapping elements which lead to replication competent virus by recombination. Thus the invention also provides a kit of parts comprising a packaging cell according to the invention and a recombinant vector according to the invention whereby there is essentially no sequence overlap leading to recombination, resulting in the production of replication competent adenovirus, between said cell and said vector.

It is within the scope of the invention to insert more genes, or a functional part of these genes from the same or from other serotypes into the adenoviral vector replacing the corresponding native sequences. Thus for example replacement of (or a functional part of the) fiber sequences with corresponding sequences of other serotypes is combined with, for example replacements of (or a functional part of) other capsid genes like penton base or hexon with corresponding sequences of said serotype or of other distinct serotypes. Persons skilled in the art understand that other combinations not limited to the said genes are possible and are within the scope of the invention.

In order to be able to precisely adapt the viral vector and provide the chimaeric virus with the desired properties at will, it is preferred that a library of adenoviral genes is provided whereby the genes to be exchanged are located on plasmid- or cosmid-based adenoviral constructs whereby the genes or the sequences to be exchanged are flanked by restriction sites. The preferred genes or sequences can be selected from the library and inserted in the adenoviral constructs that are used to generate the viruses. Typically, such a method comprises a number of restriction and ligation steps and transfection of a packaging cell. The adenoviral vector can be transfected in one piece, or as two or more overlapping fragments, whereby viruses are generated by homologous recombination. For example the adenoviral vector is built up from two or more overlapping sequences for insertion or replacements of a gene of interest in for example the E1 region, for insertion or replacements in penton and/or hexon sequences, and for insertions or replacements into fiber sequences.

A preferred aspect of the present chimaeric adenoviruses comprises the base (i.e. "tail") of one serotype and the shaft and the knob from another serotype. In this manner it becomes possible to have the parts of the protein responsible for assembly of viral particles originate from one serotype, thereby enhancing the production of intact viral particles. Thus the invention also provides a chimaeric adenovirus according to the invention, wherein the hexon, penton, fiber and/or other capsid proteins are chimaeric proteins originating from different adenovirus serotypes. Besides generating chimaeric adenoviruses by swapping entire wild type capsid (protein) genes etc. or parts thereof, it is also within the scope of the present invention to insert capsid (protein) genes etc. carrying non-adenoviral sequences or mutations such as point mutations, deletions, insertions, etc. which can be easily screened for preferred characteristics such as temperature stability, assembly, anchoring, redirected infection, altered immune response etc. Again other chimaeric combinations can also be produced and are within the scope of the present invention.

In one embodiment this invention describes adenoviral vectors that are, amongst others, especially suited for gene delivery to human primary T-lymphocytes and T-cell derived cell-lines important for functional genomics based gene validation as well as for therapeutic interventions involving T-lymphocytes. In a further embodiment, the adenoviral vectors of this invention are also especially suited for gene delivery to B and mast cells. The adenoviral vectors preferably are derived from subgroup B adenoviruses or contain at least a functional part of the fiber protein from an adenovirus from subgroup B comprising at least the cell-binding moiety of the fiber protein.

In a further preferred embodiment the adenoviral vectors are chimaeric vectors based on adenovirus type 5 and contain at least a functional part of the fiber protein from adenovirus type 51.

It is to be understood that in all embodiments the adenoviral vectors is derived from the serotype having the desired properties or that the adenoviral vector is based on an adenovirus from one serotype and contains the sequences comprising the desired functions of another serotype, these sequences replacing the native sequences in the said serotype.

In another aspect this invention describes chimaeric adenoviruses and methods to generate these viruses that have an altered tropism different from that of adenovirus serotype 5. For example, viruses based on adenovirus serotype 5 but displaying any adenovirus fiber existing in nature. This chimaeric adenovirus serotype 5 is able to infect certain cell types more efficiently, or less efficiently in vitro and in vivo than the adenovirus serotype 5. Such cells include but are not limited to T-lymphocytes (and subtypes thereof as mentioned above), mast cells, endothelial cells, smooth muscle cells, dendritic cells, hemopoietic stem cells, monocytic/macrophage cells, tumor cells, leukemic cells, skeletal muscle cells, synoviocytes, etc. As mentioned before in the introduction of this application, mast cells are obtained in different ways, including, but not limited to, harvesting them from biological isolated tissues or fluids, or growing them in vitro from tissue cultures. In another aspect the invention describes the construction and use of libraries consisting of distinct parts of adenovirus serotype 5 in which one or more genes or sequences have been replaced with DNA derived from alternative human or animal serotypes. This set of constructs, in total encompassing the complete adenovirus genome, allows for the construction of unique chimaeric adenoviruses customized for a certain disease, group of patients or even a single individual.

In all aspects of the invention the chimaeric adenoviruses may, or may not, contain deletions in the E1 region and insertions of heterologous genes linked to a promoter. Furthermore, chimaeric adenoviruses may, or may not, contain deletions in the E3 region and insertions of heterologous genes linked to a promoter. Furthermore, chimaeric adenoviruses may, or may not, contain deletions in the E2 and/or E4 region and insertions of heterologous genes linked to a promoter. In the latter case E2 and/or E4 complementing cell lines are required to generate recombinant adenoviruses. Alternatively these genes can be brought under transcriptional regulation such that these genes are only expressed when producing virus and not when using the vectors for functional genomics studies or therapeutic intervention. In fact any gene in the genome of the viral vector can be taken out and supplied in trans or be regulated. In the extreme situation, chimaeric viruses do not contain any adenoviral genes in their genome and are by definition minimal adenoviral vectors. In this case all adenoviral functions are supplied in trans using stable cell lines and/or transient expression of these genes. A method for producing minimal adenoviral vectors is described in WO97/00326 and is taken as reference herein.

In one embodiment the invention provides a gene delivery vehicle having been provided with at least a tissue tropism for T-lymphocytes, B cells or mast cells. In a preferred embodiment of the invention said gene delivery vehicle is provided with a tissue tropism for at least T-lymphocytes using a fiber protein derived from a subgroup B adenovirus, preferably of adenovirus 35 or 51. In a preferred aspect of the invention said gene delivery vehicle comprises a virus capsid. Preferably said virus capsid comprises a virus capsid derived in whole or in part from an adenovirus of subgroup B, preferably from adenovirus 35 or 51, or it comprises proteins, or parts thereof, from an adenovirus of subgroup B, preferably of adenovirus 35 or 51. In a preferred embodiment of the invention said virus capsid comprises proteins, or fragments thereof, from at least two different viruses, preferably adenoviruses. In a preferred embodiment of this aspect of the invention at least one of said virus is an adenovirus of subgroup B, preferably adenovirus 35 or 51.

In a preferred embodiment of the invention said gene delivery vehicle comprises an adenovirus fiber protein or fragments thereof. Said fiber protein is preferably derived from an adenovirus of subgroup B, preferably of adenovirus 35 or 51. Said gene delivery vehicle may further comprise other fiber proteins, or fragments thereof, from other adenoviruses. Said gene delivery vehicle may, or may not, comprise other adenovirus proteins. Nucleic acid is linked directly to fiber proteins, or fragments thereof, but may also be linked indirectly. Examples of indirect linkages include, but are not limited to, packaging of nucleic acid into adenovirus capsids or packaging of nucleic acid into liposomes, wherein a fiber protein, or a fragment thereof, is incorporated into an adenovirus capsid or linked to a liposome. Direct linkage of nucleic acid to a fiber protein, or a fragment thereof, is performed when said fiber protein, or a fragment thereof, is not part of a complex or when said fiber protein, or a fragment thereof, is part of complex such as an adenovirus capsid.

In one embodiment of the invention is provided a gene delivery vehicle comprising an adenovirus fiber protein wherein said fiber protein comprises a tissue-determining fragment of an adenovirus of subgroup B adenovirus preferably of adenovirus 35 or 51. Adenovirus fiber protein comprises three functional domains. One domain, the base, is responsible for anchoring the fiber to a penton base of the adenovirus capsid. Another domain, the knob, is responsible for receptor recognition whereas the shaft domain functions as a spacer separating the base from the knob. The different domains may also have other functions. For instance, the shaft is presumably also involved in target cell specificity. Each of the domains mentioned above is used to define a fragment of a fiber. However, fragments may also be identified in another way. For instance the knob domain comprises of a receptor binding fragment and a shaft-binding fragment. The base domain comprises of a penton base binding fragment and a shaft-binding fragment. Moreover, the shaft comprises of repeated stretches of amino acids. Each of these repeated stretches is a fragment. A tissue tropism determining fragment of a fiber protein is a single fragment of a fiber protein or a combination of fragments of at least one fiber protein, wherein said tissue tropism determining fragment, either alone or in combination with a virus capsid, determines the efficiency with which a gene delivery vehicle can transduce a given cell or cell type, preferably but not necessarily in a positive way. With a tissue or cell tropism for T-lymphocytes, B cells or mast cells is meant a tissue or cell tropism for cells having T-cell or mast cell functions.

Increasing the efficiency with which cells of said tissue are transduced provides a tropism for a certain tissue, alternatively, a tropism for a certain tissue is provided by decreasing the efficiency with which other cells than the cells of said tissue are transduced.

Fiber proteins possess tissue tropism determining properties. The most well described fragment of the fiber protein involved in tissue tropism is the knob domain. However, the shaft domain of the fiber protein also possesses tissue tropism determining properties. However, not all of the tissue tropism determining properties of an adenovirus capsid are incorporated into a fiber protein.

In a preferred embodiment of the invention, a fiber protein derived from a subgroup B adenovirus, preferably adenovirus 35 or 51, is combined with the non-fiber capsid proteins from an adenovirus of subgroup C, preferably of adenovirus 5.

In one aspect of the invention a gene delivery vehicle comprising a nucleic acid derived from an adenovirus is provided.

In a preferred embodiment of the invention, said adenovirus nucleic acid comprises at least one nucleic acid sequence encoding a fiber protein comprising at least a tissue tropism determining fragment of a subgroup B adenovirus fiber protein, preferably of adenovirus 35 or 51. In a preferred aspect said adenovirus comprises nucleic acid from at least two different adenoviruses. In a preferred aspect said adenovirus comprises nucleic acid from at least two different adenoviruses wherein at least one nucleic acid sequence encoding a fiber protein comprising at least a tissue tropism determining fragment of a subgroup B adenovirus fiber protein, preferably of adenovirus 35 or 51.

In one aspect the invention provides an adenovirus capsid with, or provided with, a tissue tropism for T-lymphocytes, B cells or mast cells wherein said capsid preferably comprises proteins from at least two different adenoviruses and wherein at least a tissue tropism determining fragment of a fiber protein is derived from a subgroup B adenovirus, preferably of adenovirus 35 or 51. In another aspect the invention provides an adenovirus capsid deprived of a tissue tropism for liver cells wherein said capsid preferably comprises proteins from at least two different adenoviruses and wherein at least a tissue tropism determining fragment of a fiber protein is derived from a subgroup B adenovirus, preferably of adenovirus 35 or 51.

In another aspect of the invention is provided construct pBr/Ad.BamRΔFib, comprising adenovirus 5 sequences 21562–31094 and 32794–35938.

In another aspect of the invention is provided construct pBr/AdBamRfib35, comprising adenovirus 5 sequences 21562–31094 and 32794–35938, further comprising an adenovirus 35 gene encoding fiber protein.

In another aspect of the invention is provided construct pBr/AdBamR.pac/fib35, comprising adenovirus 5 sequences 21562–31094 and 32794–35938, further comprising an adenovirus 35 gene encoding fiber protein, and further comprising a unique PacI-site in the proximity of the adenovirus 5 right terminal repeat, in the non-adenovirus sequence backbone of said construct.

In another aspect of the invention is provided construct pWE/Ad.AflIIrITRfib35 comprising Ad5 sequence 3534–31094 and 32794–35938, further comprising an adenovirus 35 gene encoding fiber protein.

In another aspect of the invention is provided construct pWE/Ad.AflIIrITRDE2Afib35 comprising Ad5 sequences 3534–22443 and 24033–31094 and 32794–35938, further comprising an adenovirus 35 gene encoding fiber protein.

In another aspect of the invention is provided construct pBr/AdBamRfib51, comprising adenovirus 5 sequences 21562–31094 and 32794–35938, further comprising an adenovirus 51 gene encoding fiber protein.

In another aspect of the invention is provided construct pBr/AdBamR.pac/fib51, comprising adenovirus 5 sequences 21562–31094 and 32794–35938, further comprising an adenovirus 51 gene encoding fiber protein, and further comprising a unique PacI-site in the proximity of the adenovirus 5 right terminal repeat, in the non-adenovirus sequence backbone of said construct.

In another aspect of the invention is provided construct pWE/Ad.AflIIrITRfib51 comprising Ad5 sequence 3534–31094 and 32794–35938, further comprising an adenovirus 51 gene encoding fiber protein.

In another aspect of the invention is provided construct pWE/Ad.AflIIrITRDE2Afib51 comprising Ad5 sequences 3534–22443 and 24033–31094 and 32794–35938, further comprising an adenovirus 51 gene encoding fiber protein.

In the numbering of the sequences mentioned above, the number is depicted until and not until plus.

In a preferred embodiment of the invention, said constructs are used for the generation of a gene delivery vehicle or an adenovirus capsid with a tissue tropism for T-lymphocytes.

In another aspect the invention provides a library of adenoviral vectors, or gene delivery vehicles which is one and the same or not, comprising a large selection of non-adenovirus nucleic acids. In another aspect of the invention, adenovirus genes encoding capsid proteins are used to generate a library of adenovirus capsids comprising of proteins derived from at least two different adenoviruses, said adenoviruses preferably being derived from two different serotypes, wherein preferably one serotype is an adenovirus of subgroup B. In a particularly preferred embodiment of the invention a library of adenovirus capsids is generated comprising proteins from at least two different adenoviruses and wherein at least a tissue tropism-determining fragment of fiber protein is derived from an adenovirus of subgroup B, preferably of adenovirus 35 or 51.

A fiber protein of adenovirus 35 or 51 preferably comprises of the sequence given in FIG. 4. However within the scope of the present invention analogous sequences is obtained through using codon degeneracy. Alternatively, amino-acid substitutions or insertions or deletions are performed as long as the tissue tropism determining property is not significantly altered. Such amino-acid substitutions are within the same polarity group or without.

In a preferred embodiment of the invention, said adenovirus nucleic acid is modified such that the capacity of said adenovirus nucleic acid to replicate in a target cell has been reduced or disabled. This is achieved through inactivating or deleting genes encoding early region 1 proteins.

An adenovirus nucleic acid is altered further or instead of one or more of the alterations mentioned above, by inactivating or deleting genes encoding adenovirus late proteins such as but not-limited to, hexon, penton, fiber and/or protein IX.

In a preferred embodiment of the invention all genes encoding adenovirus proteins are deleted from said adenovirus nucleic acid, turning said nucleic acid into a minimal adenoviral vector.

In another preferred embodiment of the invention, a vector or a nucleic acid, which is one and the same or not, according to the invention further comprises at least one non-adenovirus gene. Preferably, at least one of said non-adenovirus genes is selected from the group of genes encoding: T-cell relevant genes such as T-cell receptor genes, genes encoding T-cell specific secreted proteins and T-cell genes or anti T-cell genes involved in osteoclast differentiation such as RANKL/ODF. Or a cDNA from the library of genes such as described in WO 99/64582A2 can be the at least one non-adenovirus gene. Herefor arrayed or non-arrayed cDNA libraries can be build in adenoviral vectors, where the adenviral vector has tropism for at least T-lymphocytes. These libraries can be used in combination with T-lymphocyte specific assays such as T-lymphocyte proliferation and T-lymphocyte mediated cyto-toxicity.

In another aspect, the invention provides a cell for the production of a gene delivery vehicle provided with at least a tissue tropism for T-lymphocytes, B cells or mast cells preferably of human origin. In another aspect, the invention provides a cell for the production of a gene delivery vehicle deprived of at least a tissue tropism for liver cells. In a preferred embodiment of the invention said cell is an adenovirus packaging cell, wherein an adenovirus nucleic acid is packaged into an adenovirus capsid. In one aspect of an adenovirus packaging cell of the invention all proteins required for the replication and packaging of an adenovirus nucleic acid, except for the proteins encoded by early region 1, are provided by genes incorporated in said adenovirus nucleic acid. The early region 1 encoded proteins in this aspect of the invention is encoded by genes incorporated into the cells genomic DNA. In a preferred embodiment of the invention said cell is PER.C6 (ECACC deposit number 96022940). In general, when gene products required for the replication and packaging of adenovirus nucleic acid into adenovirus capsid are not provided by an adenovirus nucleic acid, the packaging cell provides them, either by transient transfection, or through stable transformation of said packaging cell. However, a gene product provided by the packaging cell may also be provided by a gene present on said adenovirus nucleic acid. For instance the packaging cell provides fiber protein, for instance through transient transfection, and is encoded by the adenovirus nucleic acid. This feature can among others be used to generate adenovirus capsids comprising of fiber proteins from two different viruses.

The gene delivery vehicles of the invention are useful for the treatment of diseases treatable by nucleic acid delivery to T-lymphocytes, B cells or mast cells. A non-limiting example of the latter is for instance genetic disorders in which T-cells or mast cells are involved such as SCID and AIDS.

The gene delivery vehicles of the invention are used as a pharmaceutical for the treatment of said diseases. Alternatively, gene delivery vehicles of the invention are used for the preparation of a medicament for the treatment of said diseases.

As previously indicated, the vectors of the present invention are useful for transducing T-lymphocytes, B cells and/or mast cells in vitro. This method can be used as a research tool in the study of adenoviral attachment and infection of cells and in a method of assaying nucleic acid function, the binding site-ligand interaction. Similarly, the recombinant coat protein comprising an adenoviral serotype 35 or 51 fiber ligand binding amino acid sequence can be used to produce heterologous virus chimera, by using such sequence to supplement or replace the native receptor binding sequence(s) in a coat protein of a carrier virus, such as a retrovirus, lentivirus, rotavirus, pox virus, etc. In cases where the tropism of an envelope virus is modified to infect T-lymphocytes, B-cells and mast cells, the sequence coding for the Ad35 or Ad 51 chimera protein described herein may be introduced into the viral packaging cell to modify the extracellular domains of one or more ubiquitous endogenous cell membrane proteins.

The present invention produces an efficient and practical method for administering a vector (particularly an adenoviral vector) to transduce T-lymphocytes, B-cells and/or mast cells in an animal for purposes of gene therapy. Gene therapy using the chimeric vectors disclosed herein can be used to treat diseases, disorders, or conditions associated with different tissues that ostensibly lack high levels of the receptor to which wild-type adenovirus type 2 or 5 fiber protein binds, and thus for which current adenoviral-mediated approaches to gene therapy are less than optimal (e.g., for delivery to T-lymphocytes, B-cells and/or mast cells). The chimeric vectors of the present invention can be used to treat any one of a number of diseases by delivering to T-lymphocytes, B cells and/or mast cells corrective DNA, i.e., DNA encoding a function that is either absent or impaired, or a discrete killing agent, e.g., DNA encoding a cytotoxin that, for example, is active only intracellularly. Diseases that are candidates for such treatment include, for example, cancer, e.g., melanoma, glioma or lung cancers; genetic disorders, e.g., cystic fibrosis, hemophilia or muscular dystrophy; pathogenic infections, e.g., human immunodeficiency virus, tuberculosis or hepatitis; heart disease, e.g., preventing restenosis following angioplasty or promoting angiogenesis to reperfuse necrotic tissue; and autoimmune disorders, e.g., Crohn's disease, colitis or rheumatoid arthritis.

These aforementioned illustrative uses are by no means comprehensive, and it is intended that the present invention encompasses such further uses, which flow from, but are not explicitly recited, in the disclosure herein. Similarly, there are numerous advantages associated with the use of the various aspects of the present invention.

The vectors useful in the present invention can be employed to contact cells either in vitro or in vivo. According to the invention "contacting" comprises any means by which a vector is introduced intracellularly; the method is not dependent on any particular means of introduction and is not to be so construed. Means of introduction are well known to those skilled in the art, and also are exemplified herein.

Accordingly, introduction into T-lymphocytes, B-cells and/or mast cells can be effected, for instance, either in vitro (e.g., in an ex vivo type method of gene therapy or in tissue culture studies) or in vivo by electroporation, transformation, transduction, conjugation or triparental mating, (co-) transfection, (co-) infection, membrane fusion with cationic lipids, high velocity bombardment with DNA-coated microprojectiles, incubation with calcium phosphate-DNA precipitate, direct microinjection into single cells, and the like. Similarly, the vectors can be introduced by means of cationic lipids, e.g., liposomes. Such liposomes are commercially available (e.g., Lipofectin®, Lipofectamine™, and the like, supplied by Life Technologies, Gibco BRL, Gaithersburg, Md.). Moreover, liposomes having increased transfer capacity and/or reduced toxicity in vivo (see, e.g., PCT patent application WO 95/21259) can be employed in the present invention. Other methods also are available and are known to those skilled in the art.

According to the invention, a "subject" (and thus a "cell" from a subject) encompasses any subject, into which a vector of the invention can be introduced, and thus encompasses an animal, including, but not limited to, an amphibian, bird, fish, insect, reptile, or mammal. Optimally a subject is a mammal, for instance, rodent, primate (such as chimpanzee, monkey, ape, gorilla, orangutan, or gibbon), feline, canine, ungulate (such as ruminant or swine), as well as, in particular, human.

The present method of ex vivo gene therapy can be used to transduce T-lymphocytes, B cells and/or mast cells, and particularly, tumor infiltrating lymphocytes (TIL) to correct genetic defects or provide new functions to cells. The first use of genetic therapy in humans involved tumor infiltrating lymphocytes (TILs) as target cells (see, Rosenberg, et al., New Engl. J. Med., 9:570–578 (1990)). TILs are a lymphocyte subpopulation that show promise as vehicles for delivery of anti-cancer therapeutics to tumor sites. These lymphocytes infiltrate into tumors, as part of an attempt by the host's immune system to mount an immunological response. TIL cells also show promise for use in methods of genetic therapy, particularly cancer therapy, (see, e.g., Culliton, "News and Comment" in Science, 244:1430–1433 (1989) and Kasid, et al., Proc. Natl. Acad. Sci., 87:473–477 (1990)) because they provide a source of autologous cells that target tumors and that can be modified by the insertions of DNA encoding a desired protein, cultured, and reintroduced into the patient.

In tumor infiltrating lymphocytes (TIL) therapy of this invention, the cell used is a lymphocyte subpopulation that targets tumors. Preferably, the cell used is a human TIL cell. These cells are particularly susceptible to ex vivo gene delivery (sometimes referred to as somatic cell therapy). Further, the genes to be delivered would be those that will enhance the ability of such cells to target and fight the tumor such as TNF, cytokines such as interleukin (IL) (e.g., IL-2, IL-4, IL-10, IL-12), interferons (IFN) (e.g., IFN-.gamma.), Granulocyte macrophage colony stimulating factor (GM-CSF) and co-stimulatory factor (e.g., B7). Preferably, one would use a multivalent vector to deliver, for example, both TNF and IL-2 simultaneously.

The genetic material that is delivered to the target cell using the method of the present invention may be a gene, for example, those that encode a variety of proteins including anticancer and antiviral agents. Such genes include those encoding various hormones, growth factors, enzymes, cytokines, receptors, MHC molecules and the like. The term "genes" includes nucleic acid sequences both exogenous and endogenous to cells into which the virus vector, for example, a chimeric adenoviral ad5/ad51 vector containing the human TNF gene may be introduced. Of particular interest for use as genes for delivery are those genes encoding polypeptides either absent, produced in diminished quantities, or produced in mutant form in individuals suffering from a genetic disease, such as adenosine deaminase (ADA) or immunoglobulin. Additionally, it is of interest to use genes encoding polypeptides for secretion from the target cell so as to provide for a systemic effect by the protein encoded by the gene. Specific genes of interest include those encoding TNF, TGF-.alpha., and TGF-beta. hemoglobin, interleukin-1, interleukin-2, interleukin-3, interleukin-4, interleukin-5, interleukin-6, interleukin-7, interleukin-8, interleukin-9, interleukin-10, interleukin-11, interleukin-12 etc., GM-CSF, G-CSF, M-CSF, human growth factor, co-stimulatory factor B7, insulin, factor VIII, factor IX, PDGF, EGF, NGF, IL-ira, EPO, beta.-globin and the like, as well as biologically active muteins of these proteins. Genes for insertion into the viral vectors may be from a variety of species; however, preferred species sources for genes of interest are those species into which the viral vector containing the gene of interest is to be inserted. The gene may further encode a product that regulates expression of another gene product or blocks one or more steps in a biological pathway, such as the sepsis pathway. In addition, the gene may encode a toxin fused to a polypeptide, e.g., a receptor ligand, or an antibody that directs the toxin to a target, such as a tumor cell or a virus. Similarly, the gene may encode a therapeutic protein fused to a targeting polypeptide, to deliver a therapeutic effect to a diseased tissue or organ.

The gene may also encode a marker, such as beta-galactosidase, CAT, neomycin or methotrexate resistance, whereby the target cells may be selected or detected. The use of such a marker allows the skilled artisan to screen various viral vectors for those that are non-lytic or non-cytopathic in a particular target cell. For example, the gene encoding beta-galactosidase (lacZ) can be inserted into a viral vector, the modified virus vector is then introduced into the target cell and the production of beta-galactosidase is measured. Expression of beta-gal provides an indication of viral infectivity and gene expression.

The method of the present invention as mentioned above is useful for delivery of multiple genes to the target cell, whether it is a T-lymphocyte, B cell or mast cell, and particularly TIL. The construction of multivalent vectors capable of delivering multiple genes is within the level of skill in the art and may be effected by known methodologies. The co-expression of a lymphokine such as GM-CSF and an antigenic polypeptide, such as a cancer antigen, by a chimeric vector ensures that they are produced together by the same target cells in a very localized area. The vector can also be used to deliver genes to T-lymphocytes, B cells and/or mast cells to enhance the ability of the immune system to fight a particular disease or tumor. For example, a vector delivering one or more cytokines (e.g., IL-2) to boost the immune system and/or one or more antigens.

TIL cells for use as target cells for gene delivery can be produced in vitro by incubating resected human tumors, such as kidney, colon or breast tumors, melanomas, and sarcomas in vitro in appropriate tissue culture medium that contains interleukin-2 (IL-2). The IL-2 in the medium results in the expansion and activation of T cells within the tumor, the TIL cells, and the destruction of tumor cells or tissue. After 2–8 weeks in culture, the tumor cells have been destroyed and the culture primarily contains lymphoid cells that have the phenotype of cytolytic T lymphocytes (CTL) (see, e.g., Rosenberg, et al., New Engl. J. Med., 319: 1676–1680 (1988); Muul, et al., J. Immunol., 138:989–995 (1987); and Topalian, et al., J. Immunol., 142:3714–3725 (1987)).

Generally, between $1\times10^5$ and a maximum of $2\times10^{11}$ cells per infusion are administered in, for example, one to three infusions of 200 to 250 ml each over a period of 30 to 60 minutes. After the completion of the infusions, the patient may be treated with recombinant interleukin-2 with a dose of 720,000 IU per kilogram of body weight intravenously every eight hours; some doses can be omitted depending on the patient's tolerance for the drug.

TILs can also be modified by introduction of a viral vector containing a DNA encoding TNF and reintroduced into a subject in an effort to enhance the anti-tumor activity of the TIL cells. Other cytokines can also be used.

The method of the present invention may be used to deliver genes encoding, for example, TNF and/or interleukin-2 (IL-2) to tumor cells. It is expected that secretion of these cytokines will stimulate a tumor-specific immune response that would either result in tumor destruction at other sites or allow the collection of more effective TIL from lymph nodes near the site of the injected tumor cells.

Pharmaceutically acceptable excipients also are well known to those who are skilled in the art, and are readily available. The choice of excipient will be determined in part by the particular method used to administer the recombinant vector. Accordingly, there are a wide variety of suitable formulations for use in the context of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

A vector of the present invention, alone or in combination with other suitable components can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Additionally, a vector of the present invention can be made into suppositories by mixing with a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the gene of interest, the composition employed, the method of administration, and the particular site and organism being treated. However, the dose should be sufficient to effect a therapeutic response.

EXAMPLES

Example 1

Generation of Adenovirus Serotype 5 Based Viruses with Chimaeric Fiber Proteins.

The method described infra to generate recombinant adenoviruses by co-transfection of two, or more separate cloned adenovirus sequences. These cloned adenoviral sequences were subsequently used to remove specific adenovirus serotype 5 sequences in order to generate "template clones" which allow for the easy introduction of DNA sequences derived from other adenovirus serotypes. As an example of these template clones, the construction of plasmids enabling swapping of DNA encoding for fiber protein is given.

I-1 Generation of Adenovirus Template Clones Lacking DNA Encoding for Fiber

Figure 2:
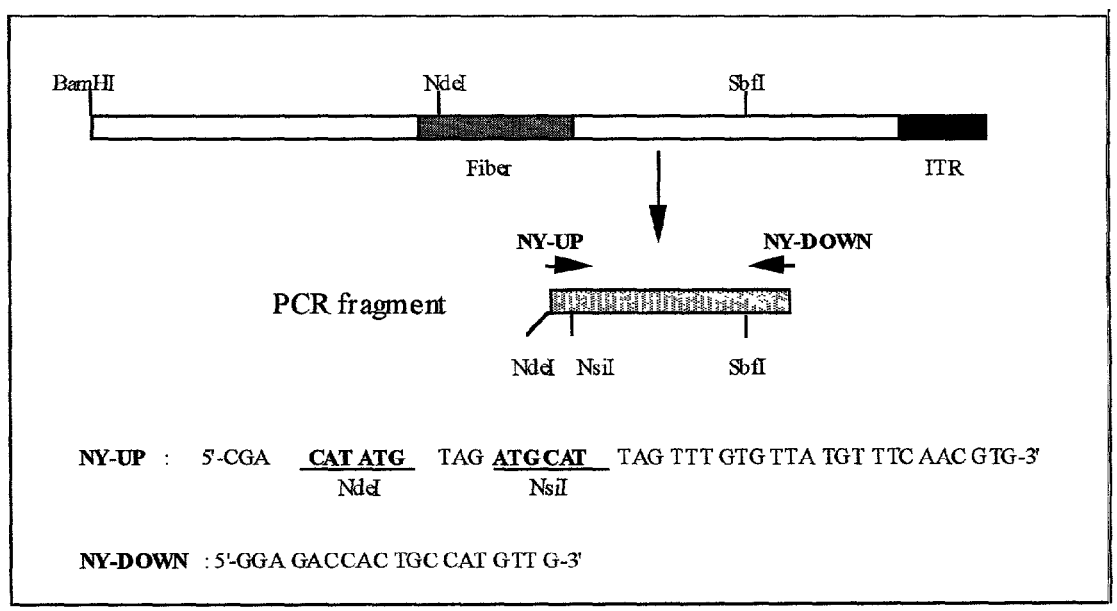
FIG. 2 is a schematic representation of the strategy used to generate plasmid pBr/Ad.Bam-rITR deltafib in which the adenovirus type 5 fiber DNA is replaced by a short stretch containing an unique NsiI site.

The fiber coding sequence of adenovirus serotype 5 is located between nucleotides 31042 and 32787. To remove the adenovirus serotype 5 DNA encoding fiber, we started with construct pBr/Ad.Bam-rITR (FIG. 1; ECACC deposit p97082122). First an NdeI site was removed from this construct. For this purpose, pBr322 plasmid DNA was digested with NdeI after which protruding ends were filled using Klenow-enzyme. This pBr322 plasmid was then re-ligated, digested with NdeI and transformed into E.coli DH5α. The obtained pBr/ΔNdeI plasmid was digested with ScaI and SalI and the resulting 3198 bp vector fragment was ligated to the 15349 bp ScaI-SalI fragment derived from pBr/Ad.BamrITR, resulting in plasmid pBr/Ad.Bam-rITRΔNdeI that hence contained a unique NdeI site. Next a PCR was performed with oligonucleotides "NY-up" (SEQ ID NO.: 16) and "NY-down"(SEQ ID NO.: 17). A schematic presentation of the strategy used to delete the fiber gene is shown in FIG. 2. During amplification, both an NdeI and an NsiI restriction site were introduced to facilitate cloning of the amplified fiber DNAs. Amplification consisted of 25 cycles of each 45 sec. at 94° C., 1 min. at 60° C. and 45 sec. at 72° C. The PCR reaction contained 25 pmol of oligonucleotides NY-up or NY-down, 2 mM dNTP, PCR buffer with 1.5 mM $MgCl_2$, and 1 unit of Elongase heat stable polymerase (Gibco, The Netherlands). One-tenth of the PCR product was run on an agarose gel, which demonstrated that the expected DNA fragment of ±2200 bp was amplified. This PCR fragment was subsequently purified using Geneclean kit system (Bio101 Inc.). Then, both the construct pBr/Ad.Bam-rITRΔNdeI as well as the PCR product were digested with restriction enzymes NdeI and SbfI. The PCR fragment was subsequently cloned using T4 ligase enzyme into the NdeI and SbfI digested pBr/Ad.Bam-rITRΔNdeI, generating pBr/Ad.BamRΔFib. This plasmid allows insertion of any PCR amplified fiber sequence through the unique NdeI and NsiI sites that are inserted in place of the removed fiber sequence. Viruses can be generated by a double homologous recombination in packaging cells described infra using an adapter plasmid, construct pBr/Ad.AflII-EcoRI digested with PacI and EcoRI and a pBr/Ad.BamRΔFib construct in which heterologous fiber sequences have been inserted.

Figure 3:
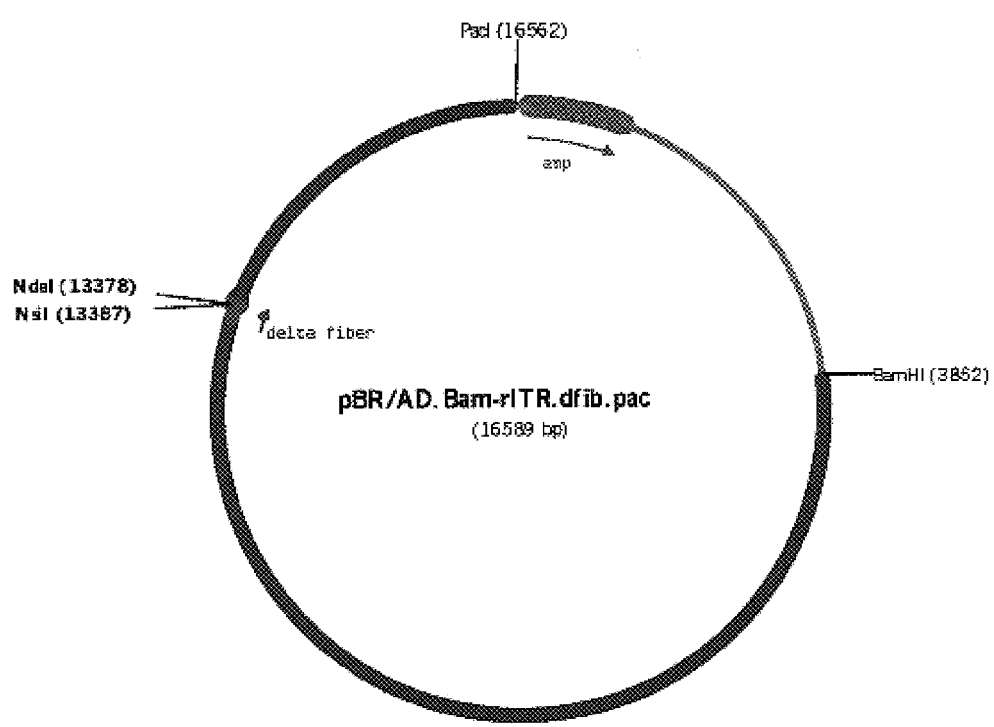
FIG. 3 is a schematic drawing of construct pBr/Ad.Bam-rITR deltafib.pac.

To increase the efficiency of virus generation, the construct pBr/Ad.BamRΔFib was modified to generate a PacI site flanking the right ITR. Hereto, pBr/Ad.BamRΔFib was digested with AvrII and the 5 kb adenofragment was isolated and introduced into vector pBr/Ad.Bam-rITR.pac#8 (ECACC deposit p97082121) replacing the corresponding AvrII fragment. The resulting construct was named pBr/Ad.BamRΔFib.pac (FIG. 3). Once a heterologous fiber sequence is introduced in pBr/Ad.BamRΔFib.pac, the fiber modified right hand adenovirus clone is introduced into a large cosmid clone pWE/Ad.AflII-rITR. Such a large cosmid clone allows generation of adenovirus by only one homologous recombination making the process extremely efficient.

I-2: Amplification of Fiber Sequences from Adenovirus Serotypes

To enable amplification of the DNAs encoding fiber protein derived from alternative serotypes degenerate oligonucleotides were synthesized. For this purpose, first known DNA sequences encoding for fiber proteins of alternative serotypes were aligned to identify conserved regions in both the tail-region as well as the knob-region of the fiber protein. From the alignment, (degenerate) oligonucleotides were synthesized (Table 1). Also shown in Table 1 is the combination of oligonucleotides used to amplify the DNA encoding fiber protein of a specific serotype. The amplification reaction (50 µl) contained 2 mM dNTPs, 25 pmol of each oligonucleotide, standard 1×PCR-buffer, 1.5 mM $MgCl_2$, and 1 Unit Pwo heat stable polymerase (Boehringer) per reaction. The cycler program contained 20 cycles, each consisting of 30 sec. 94° C., 60 sec. 60–64° C. and 120 sec. 72° C. One-tenth of the PCR product was run on an agarose gel which demonstrated that a DNA fragment was amplified. Of each different template, two independent PCR reactions were performed.

TABLE I

Oligonucleotides and degenerate oligonucleotides used for the amplification of DNA encoding fiber proteins derived from alternative human adenovirus serotypes. Bold letters represent an NdeI restriction site (A-E), an NsiI restriction site (1-6, 8), or a PacI restriction site (7).

| Adenovirus Serotype | Tail oligonucleotide | Knob oligonucleotide |
|---|---|---|
| 4 | A | 1 |
| 8 | B | 2 |
| 9 | B | 2 |
| 12 | E | 3 |
| 16 | C | 4 |
| 19p | B | 2 |
| 28 | B | 2 |
| 32 | B | 2 |
| 35 | C | 8 |
| 36 | B | 2 |
| 37 | B | 2 |
| 40-1 | D | 5 |
| 40-2 | D | 6 |
| 41-s | D | 5 |
| 41-1 | D | 7 |
| 49 | B | 2 |
| 50 | B | 2 |
| 51 | C | 8 |

A: 5'-CCC GTG TAT CCA TAT GAT GCA GAC AAC GAC CGA CC-3'

B: 5'-CCC GTG TAC CCA TAT GGC TAG GCG CGG-3'

C: 5'-CCK GTS TAC CCA TAT GAA GAT GAA AGC-3'

D: 5'-CCC GTG TAC CCA TAT GAC ACC TYG TCA ACT C-3'

E: 5'-CCC GTT TAC CCA TAT GAC CCA TTT GAC ACA TCA GAC-3'

1: 5'-CCG ATG CAT TTA TTG TTG GGC TAT ATA GGA-3'

2: 5'-CCG ATG CAT TYA TTC TTG GGC RAT ATA GGA-3'

3: 5'-CCG ATG CAT TTA TTC TTG GGR AAT GTA WGA AAA GGA-3'

4: 5'-CCG ATG CAT TCA GTC ATC TTC TCT GAT ATA-3'

5: 5'-CGG ATG CAT TTA TTG TTC AGT TAT GTA GCA-3'

TABLE I-continued

Oligonucleotides and degenerate oligonucleotides used for the amplification of DNA encoding fiber proteins derived from alternative human adenovirus serotypes. Bold letters represent an NdeI restriction site (A-E), an NsiI restriction site (1-6, 8), or a PacI restriction site (7).

6: 5'-GCC ATG CAT TTA TTG TTC TGT TAC ATA AGA-3'

7: 5'-CCG TTA ATT AAG CCC TTA TTG TTC TGT TAC ATA AGA A-3'

8: 5'-CCG ATG CAT TCA GTC ATC YTC TWT AAT ATA-3'

In the sequence listing, oligonucleotides A–E are given as SEQ ID's 3–7, and oligonucleotides 1–8 are given as SEQ ID's 8–15, respectively.

I-3: Generation of Fiber Chimaeric Adenoviral DNA Constructs

Both amplified fiber DNAs and the vector (pBr/Ad.BamRΔFib) were digested with NdeI and NsiI. The digested DNAs were subsequently run on an agarose gel after which the fragments were isolated from the gel and purified using the Geneclean kit (Bio101 Inc). The PCR fragments were then cloned into the NdeI and NsiI sites of pBr/AdBamRΔFib, thus generating pBr/AdBamRFib35 and pBr/AdBamRFib51. The inserts generated by PCR were sequenced to confirm correct amplification. The obtained sequences of the different fiber genes are shown in FIG. 4. From pBr/AdBamRFib35 and pBr/AdBamRFib51, PWE/Ad.AflII-rITRfib35 and PWE/Ad.AflII-rITRfib51 cosmids were generated as described above. Example 1: FIGS. 4A and 4B

The first 35 amino acids of Ad5 fiber are retained in the chimeric fibers of Ad5–Ad35 and Ad5–Ad51. This portion of 35 amino acids equals 7.07% of Ad5fiber (total 495 amino acids). Ad5 fiber amino acids 5–35 were confirmed by DNA sequencing. The sequence of the N-terminal 4 amino acids (i.e. MSVS or Met Ser Val Ser) is known in the prior art. See, e.g., Chroboczek, J. and Jacrot, B. The sequence of adenovirus fiber: similarities and differences between serotypes 2 and 5. Virology 161:549–554 (1987). The full sequences are listed in FIGS. 4A and 4B (SEQ ID NO 1 and SEQ ID NO 2).

I-4: Generation of Recombinant Adenovirus Chimaeric for Fiber Protein

Figure 5:
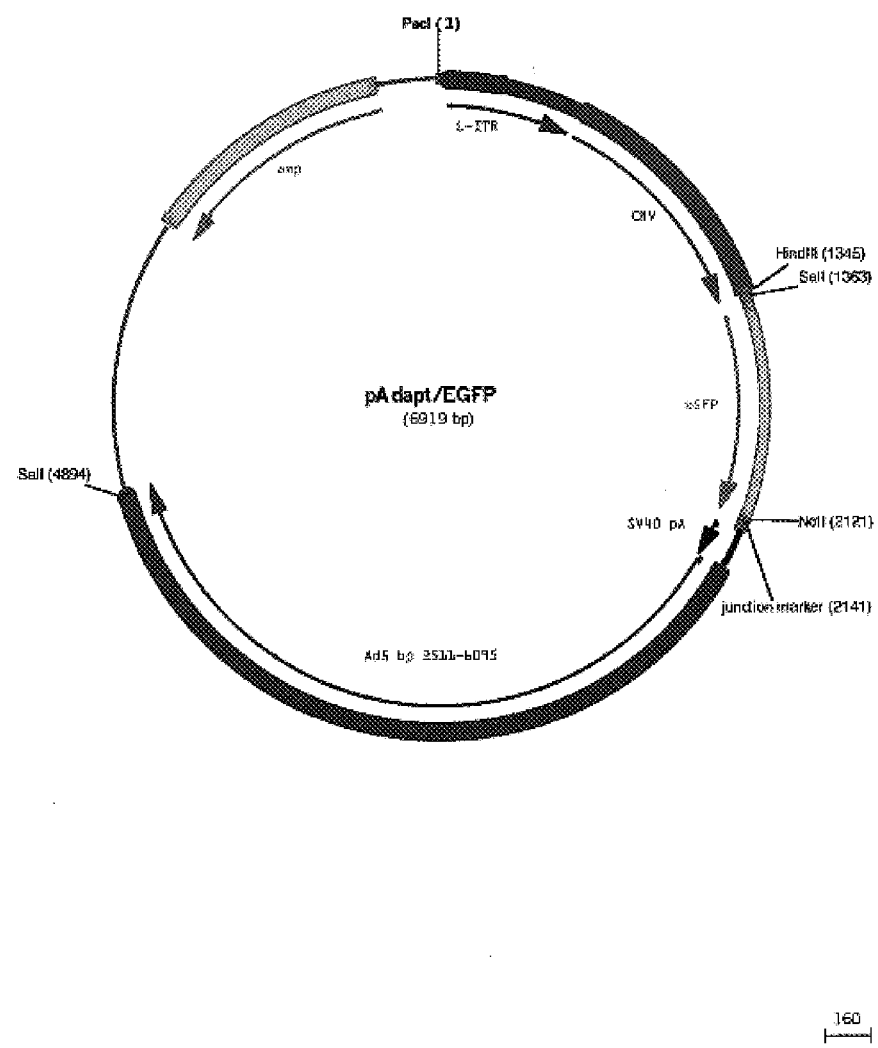
FIG. 5 is a schematic drawing of the adapter construct pAdApt/eGFP.
Figure 6:
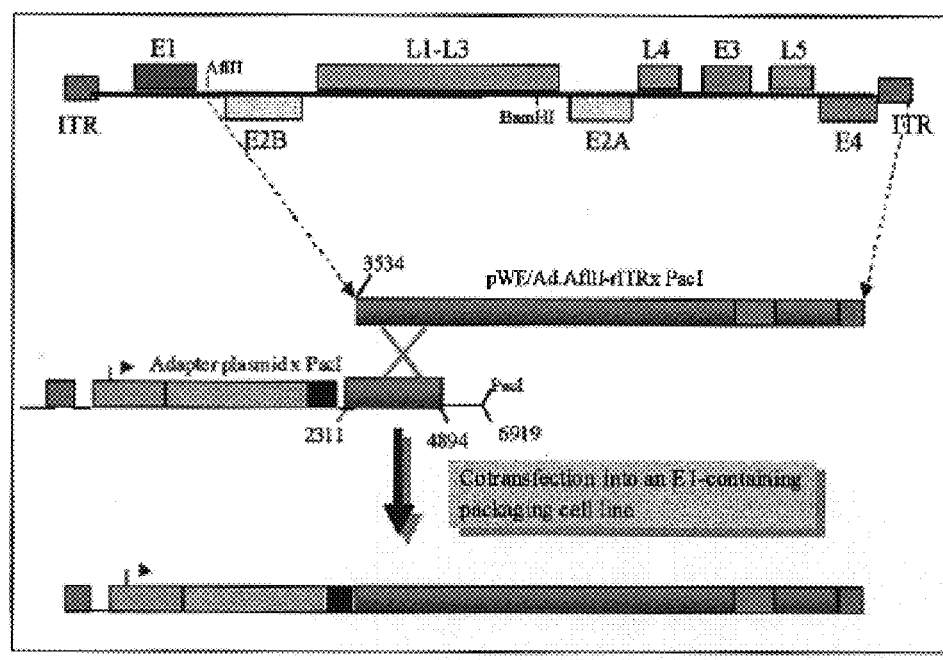
FIG. 6 is a schematic presentation of the method to generate recombinant adenoviruses using two overlapping fragments. This system requires only one recombination event. Early (E) and late regions (L) are indicated. L5 is the fiber coding sequence.

To generate recombinant Ad5 virus carrying the fiber of serotype 35 or 51, two constructs pAdApt/eGFP (FIG. 5) and pWE/Ad.AflII-rITR/Fib35 or pWE/Ad.AflII-rITR/Fib51 were transfected into adenovirus producing cells (FIG. 6).

For transfection, 4 μg of pAdApt/eGFP linearized with PacI plus 4 μg of pWE/Ad.AflII-rITR/Fib35 or pWE/Ad.AflII-rITR/Fib51, also linearized with PacI, were diluted in serum free DMEM to 100 μl total volume. To this DNA suspension 100 μl 1× diluted lipofectamine (Gibco) was added. After 30 minutes at room temperature the DNA-lipofectamine complex solution was added to 2.5 ml of serum-free DMEM, which was subsequently added to a T25 cm² tissue culture flask. This flask contained 2×10⁶ PER.C6 cells that were seeded 24-hours prior to transfection. Two hours later, the DNA-lipofectamine complex containing medium was diluted once by the addition of 2.5 ml DMEM supplemented with 9 mM MgCl₂ and 20% fetal calf serum. Again 24 hours later the medium was replaced by fresh DMEM supplemented with 9 mM MgCl₂ and 10% fetal calf serum. Cells were cultured for 6–8 days, subsequently harvested, and freeze/thawed 3 times. Cellular debri was removed by centrifugation for 5 minutes at 3000 rpm room temperature. Of the supernatant (12.5 ml) 3–5 ml was used to again infect PER.C6 cells in T80 m²tissue culture flasks. This re-infection results in full cytopathogenic effect (CPE) after 5–6 days, after which the adenovirus is harvested as described above. Again the virus is amplified. For this, 1 ml supernatant is used to infect PER.C6 cells (T175 cm² tissue culture flasks). This re-infection results in full cytopathogenic effect (CPE) after 4 days. Then the adenovirus is harvested, freeze/thawed 3 times and centrifuged for 5 minutes at 3000 rpm and room temperature. Supernatant is filtered through a 0.2/0.8 μm filter and aliquoted as crude lysates. The number of virus particles per ml is determined by running the virus in a Quantitative Real-Time PCR. The virus titers that were found are:

Ad5\dE1.fib35.pAdApt/eGFP $1.19×10^{10}$ vp/ml; Ad5\dE1.fib51.pAdApt/eGFP $2.81×10^9$ vp/ml.

I-5: Production of Fiber Chimaeric Adenoviruses

For amplifications a T175 cm² flasks with adherent perC6 cells with a confluency of ±70% are infected with 2.5 ml virus until this resulted in full cytopathogenic effect (CPE) within 3–5 days. The adenovirus was then harvested and freeze-thawed 3 times. Cellular debris was removed by centrifugation for 5 min at 3000 rpm and room temperature. Then 2.5 ml of the harvested virus was used to infect 4 T175 cm² 3-layer flasks that contained adherent PER.C6 cells with a confluency of ±70%. Three days after infection, the cells were harvested and pelleted by centrifugation for 5 min at 1500 rpm at room temperature. The chimaeric adenovirus present in the pelleted cells was subsequently extracted and purified using the following downstream processing protocol. The pellet was dissolved in 20 ml 10 mM NaPO₄ with 7% glycerol and frozen at −20° C. After thawing at 37° C., 2.25 ml deoxycholate (5% w/v) was added after which the solution was homogenized. The solution was subsequently incubated for 5 minutes at 37° C. to completely crack the cells. After homogenizing the solution again, 750 μl 1M MgCl₂ and 150 μl DNase (10 mg/ml; 10⁶ U/ml) was added. The solution is than homogenized and incubated for 15 minutes at 37° C. After 10 minutes the fluid was homogenized again. Cell debris was removed by centrifugation at 3000 rpm for 30 minutes at room temperature without the brake on. The supernatant was subsequently purified from proteins by loading on 20 ml of freon and centrifuged for 20 minutes at 2000 rpm without brake at room temperature. The upper fraction is then pipetted on a Tris/HCl (1M) buffered caesiumchloride blockgradient (range: 1.2 to 1.4 g/ml). Upon centrifugation at 21000 rpm for 2 hours at 10° C. the virus was purified from remaining protein and cell-debris since the virus band will be positioned on the border of the 1.2 g/ml and the 1.4 g/ml caesium chloride solution. The virus band is isolated after which a second purification using a Tris/HCl (1M) buffered continues gradient of 1.33 g/ml of caesiumchloride is performed. After virus loading on top of this gradient the virus is centrifuged for 17 hours at 55000 rpm at 10° C. Subsequently the virus band is isolated and 50 w/v % sucrose is added to the virus to a final concentration of 1 w/v %. Excess caesium chloride is removed by three rounds of dialysis, each round comprising at least 1 hour. For dialysis the virus is transferred to dialysis slides (Slide-a-lyzer, cut off 10000 kDa, Pierce, USA). The buffers used for dialysis are PBS, which are supplemented with an increasing concentration of sucrose (round 1 to 3: 30 ml, 60 ml, and 150 ml 50 w/v % sucrose/1.5 liter cold PBS, all supplemented with 7.5 ml 2 w/v % $CaMgCl_2$). After dialysis, the virus is removed from the slide-a-lyzer after which it is aliquoted in portions of 50 µl upon which the virus is stored at −85° C. To determine the number of virus particles per ml, 50 µl of the virus batch is run on a high-pressure liquid chromatograph (HPLC) as described by Shamram et al (1997). The virus titers that were found are: Ad5\dE1.fib35.pAdApt/eGFP $1.3 \times 10^{12}$ vp/ml;
Ad5\dE1.fib51.pAdApt/eGFP $1.7 \times 10^{12}$ vp/ml.

Example 1A

An Ad5/Fiber35 Chimeric Vector with Cell Type Specificity for Hemopoietic $CD34^+Lin^-$ Stem Cells Cells isolated from human bone marrow, umbilical cord blood, or mobilized peripheral blood carrying the flow cytometric phenotype of being positive for the CD34 antigen and negative for the early differentiation markers CD33, CD38, and CD71 ($lin^-$) are commonly referred to as hemopoietic stem cells (HSC). Genetic modification of these cells is of major interest since all hemopoietic lineages are derived from these cells and therefore the HSC is a target cell for the treatment of many acquired or congenital human hemopoietic disorders. Examples of diseases that are possibly amenable for genetic modification of HSC include, but are not limited to, Hurlers disease, Hunter's disease, Sanfilippos disease, Morquios disease, Gaucher disease, Farbers disease, Niemann-Pick disease, Krabbe disease, Metachromatic Leucodistrophy, I-cell disease, severe immunodeficiency syndrome, Jak-3 deficiency, Fucosidose deficiency, thallasemia, and erythropoietic porphyria. Besides these hemopoietic disorders, also strategies to prevent or treat acquired immunodeficiency syndrome ("AIDS") and hemopoietic cancers are based on the genetic modification of HSCs (or cells derived from HSCs such as CD4 positive T lymphocytes in case of AIDS). Efficient gene delivery to HSCs is a major interest for the field of gene therapy.

This example demonstrates the ability to introduce DNA into the HSC to complement on a genetic level for a gene and protein deficiency. In case of strategies for AIDS or cancer, the DNA to be introduced into the HSC can be anti-viral genes or suicide genes. Several other areas exist in which efficient transduction of HSCs using adenoviral vectors can play an important role, for instance, in the field of tissue engineering. In this area, it is important to drive differentiation of HSCs to specific lineages. Some, non-limiting, examples are ex vivo bone formation, cartilage formation, skin formation, as well as the generation of T-cell precursors or endothelial cell precursors. The generation of bone, cartilage or skin in bioreactors can be used for transplantation after bone fractures or spinal cord lesions or severe burn injuries. Naturally, transduced cells can also directly be re-infused into a patient. The formation of large numbers of endothelial cell precursor from HSCs is of interest since these endothelial precursor cells can home, after re-infusion, to sites of cardiovascular injury such as ischemia. Likewise, the formation of large numbers of T-cells from HSCs is of interest since these T-cell precursors can be primed, ex vivo, to eradicate certain targets in the human body after re-infusion of the primed T-cells. Preferred targets in the human body can be tumours or virus infected cells.

Alteration of the Ad5 host cell range to be able to target HSCs in vitro as well as in vivo is shown herein. The tropism of chimeric Ad5/fib35 and Ad5/fib51 for HSC are studied herein. Ad5 is included as a reference These vectors are tested on human TF-1 (erythroid leukemia, ATCC CRL-2003), human primary stroma cells and human HSCs. Human TF-1 cell were routinely maintained in DMEM supplemented with 10% FCS and 50 ng/ml IL-3 (Sandoz, Basel, Switzerland). Human primary fibroblast-like stroma, isolated from a bone marrow aspirate, is routinely maintained in DMEM/10% FCS. Stroma was seeded at a concentration of $1 \times 10^5$ cells per well of 24-well plates. 24 hours after seeding cells were exposed for 2 hours to 1000 virus particles per cell of Ad5, Ad5.Fib35, or Ad5.Fib51 all carrying GFP as a marker. After 2 hours, cells were washed with PBS and reseeded in medium without addition of virus. TF-1 cells were seeded at a concentration of $2 \times 10^5$ cells per well of 24-well plates and were also exposed for 2 hours to 1000 virus particles of the different chimeric adenoviruses. Virus was removed by washing the cells after the 2 hours exposure. Both cell types were harvested 48 hours after virus exposure and analysed for GFP expression using a flow cytometer. The results on TF-1 cells, demonstrate that chimeric adenoviruses carrying a fiber from serotypes 35 or 51 (all derived from adenovirus subgroup B) have preferred infection characteristics as compared to Ad5 (subgroup C). Primary human stroma was tested since these cells are commonly used as a "feeder" cell to allow proliferation and maintenance of HSCs under ex vivo culture conditions. In contrast to the transduction of TF-1 cells, none of the fiber chimeric adenoviruses were able to efficiently transduce human primary stroma. Reasonable infection of human fibroblast-like primary stroma was observed only with Ad5 despite the observation that none of the known receptor molecules are expressed on these cells. The absence of infection of human stroma using the chimeric viruses is advantageous since, in a co-culture setting, the chimeric adenovirus will not be absorbed primarily by the stroma "feeder" cells.

To test the transduction capacity of the fiber chimeric viruses, a pool of umbilical cord blood (3 individuals) was used for the isolation of stem cells. $CD34^+$ cells were isolated from mononuclear cell preparation using a MACS laboratory separation system (Miltenyi Biotec) using the protocol supplied by the manufacturer. Of the $CD34^+$ cells, $2 \times 10^5$ were seeded in a volume of 150 µl DMEM (no serum; Gibco, Gaithersburg, Md.) and 10 µl of chimeric adenovirus (to give a final virus particles/cell ratio of 1000) was added. The chimeric adenoviruses tested were Ad5, Ad5.Fib35, Ad5.Fib51 all containing GFP as a marker. Cells were incubated for 2 hours in a humidified atmosphere of 10% $CO_2$ at 37° C. Thereafter, cells were washed once with 500 µl DMEM and re-suspended in 500 µl of StemPro-34 SF medium (Life Technologies, Grand Island, N.Y.).

Cells were then cultured for 5 days in 24-well plates (Greiner, Frickenhausen, Germany) on irradiated (20 Gy) pre-established human bone marrow stroma, in a humidified atmosphere of 10% CO2 at 37° C. After 5 days, the entire cell population was collected by trypsinization with 100 μl 0.25% Trypsin-EDTA (Gibco). The number of cells before and after 5 days of culture was determined using a hematocytometer. The number of CD34$^+$ and CD34$^{++}$CD33,38, 71$^-$ cells in each sample was calculated from the total number of cells recovered and the frequency of the CD34$^{++}$ CD33,38,71$^-$ cells in the whole population as determined by FACS analysis. The transduction efficiency was determined by FACS analysis while monitoring in distinct sub populations the frequency of GFP expressing cells as well as the intensity of GFP per individual cell. The results of this experiment demonstrate that Ad5 does not infect CD34$^+$Lin$^-$ cells as witnessed by the absence of GFP expression. In contrast, with the chimeric viruses carrying the fiber molecule of serotypes 51 or 35 high percentages of GFP positive cells are scored in this cell population. Specificity for CD34$^+$Lin$^-$ is demonstrated since little GFP expression is observed in CD34$^+$ cells that are also expressing CD33, CD38, and CD71. Sub-fractioning of the CD34$^+$Lin$^-$ cells (FIG. 22) showed that the percentage of cells positive for GFP declines using Ad5.Fib35 or Ad5.Fib51 when the cells become more and more positive for the early differentiation markers CD33 (myeloid), CD71 (erythroid), and CD38 (common early differentiation marker). These results thus demonstrate the specificity of the chimeric adenoviruses Ad5.Fib35, and Ad5.Fib51 for HSCs.

Example 2

Adenoviral Transduction of Human CD3$^+$ T-lymphocytes with Crude and Purified Vector Preparations.

II-1: Isolation and Transduction of Primary T-Lymphocytes

To determine the transduction efficiency on human T-lymphocytes with chimaeric adenoviral vectors as described under Example 1, CD3$^+$ cells were isolated from peripheral human blood. First the mononuclear cells were isolated from the blood by spinning the blood through a Vacutainer Cell Preparation Tube with Sodium Heparine (Becton Dickinson) for 30 minutes at 3700 rpm, low acceleration and no brake. The cells were washed once with PBS. Then the mononuclear cells were subjected to cell affinity chromatography using the Pan T-cell isolation kit and the Macs system of Miltenyi Biotec for isolation of CD3$^+$ cells. The isolated cells were treated with an ammonium-chloride solution of 155 mM for a period of 2 minutes on ice to eliminate the remaining erythrocytes.

Figure 7:
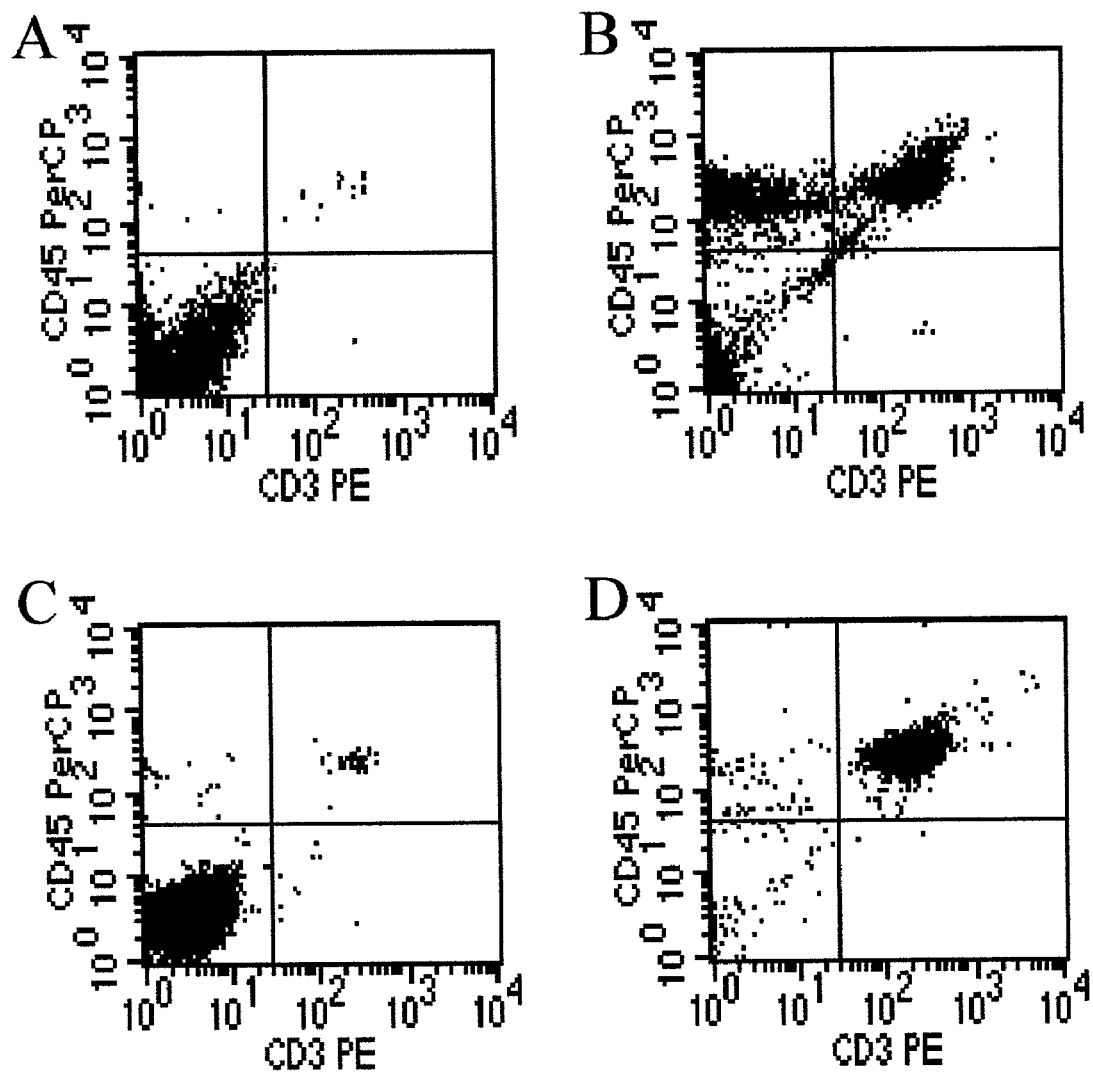
FIG. 7 is an analysis of T-cells isolated from peripheral human blood as described in Example 2. The total cell-population before isolation and the isolated T-cell population were unstained (resp. a and c) and stained for CD3 (-PE) and CD45 (-PerCP) expression (resp. b and d), followed by flow cytometry analysis to determine the percentage of $CD3^+$ $CD45^+$-lymphocytes.

The percentage of CD3$^+$ cells was determined by staining the isolated cells with CD3 antibodies labelled with PE (Becton and Dickinson) and CD45 antibodies labelled with PerCp (Becton and Dickinson) followed by flow cytometric analysis (FIG. 7).

The CD3$^+$ T-lymphocytes were then cultured in 24 well plates with 2×10$^5$ cells per well using RPMI 1640 medium containing 10% heat inactivated FBS and incubation in a humidified CO$_2$ incubator set at 37° C. and 10% CO$_2$. Transduction was performed in duplicate with 11 different adenoviral vectors carrying the eGFP transgene under the control of a CMV-promoter. The MOI that was used varied from 250 till 25000 VP/cell (Table II) in a total volume of 300 μls. Cells with virus were centrifuged for 5 min at 1500 rpm and incubated in a humidified CO$_2$ incubator set at 37° C. and 10% CO$_2$. Control transductions included a human T-cell-line SupT1 and the ovarian cancer cell-line A549.

TABLE II (Example 2): Compilation of viruses used in Example 2. MOIs are given in virusparticles (VP)/cell (* means assumed MOI). Crude stands for crude lysates from adenoviral vector producing PER.C6 or PER.C6/E2A cells. Pure stands for viral vector purified through CsCl-banding.

| Virus | MOI (Vp/cell) exp I | MOI (Vp/cell) exp II | MOI (Vp/cell) exp III |
|---|---|---|---|
| Uninfected | 0 | 0 | 0 |
| Ad5\dE1.pIPspAdApt6/eGFP crude | 250 | | |
| Ad5\dE1.dE2A.pAdApt/eGFP crude | | 250, 2500 | 250, 2500 |
| Ad5\dE1.fib35.pAdApt/eGFP crude | 2975 | 250, 2500 | 250, 2500 |
| Ad5\dE1.fib51.pAdApt/eGFP crude | 703 | 250, 2500 | 250, 2500 |
| Ad5\dE1.fib40L.pAdApt/eGFP crude | 2500* | | |
| Ad5\dE1.fib45.pAdApt/eGFP crude | 2500* | | |
| Ad5\dE1.dE2A.pIPspAdApt6/ empty crude | 1575 | 250, 2500 | 250, 2500 |
| Ad5\dE1.dE2A.pAdApt/eGFP pure | 2500 | 250, 2500 | 250, 2500 |
| Ad5\dE1.fib35.pAdApt/eGFP pure | 2500 | 2500, 25000 | 2500, 25000 |
| Ad5\dE1.fib51.pAdApt/eGFP pure | 2500 | 2500, 25000 | 2500, 25000 |
| Ad5\dE1.dE2A.pAdApt/empty pure | 2500 | 250, 2500 | 250, 2500 |

After 48, 72 or 96 hours (in experiment II and III after 48 hours) of incubation, the cells were transferred to tubes, washed once with PBS containing 0.5% BSA by centrifugation. Washing was followed by incubation with anti CD3-antibodies labelled with PE for 30 minutes on ice. The cells were then washed 2 times and resuspended in 200 μls of PBS with 0.5% BSA. The number of eGFP$^+$CD3$^+$ T-lymphocytes was then determined using a flow cytometer (FIGS. 8 and 9c).

II-2: Transduction of Human A549 Cells

Figure 9A:
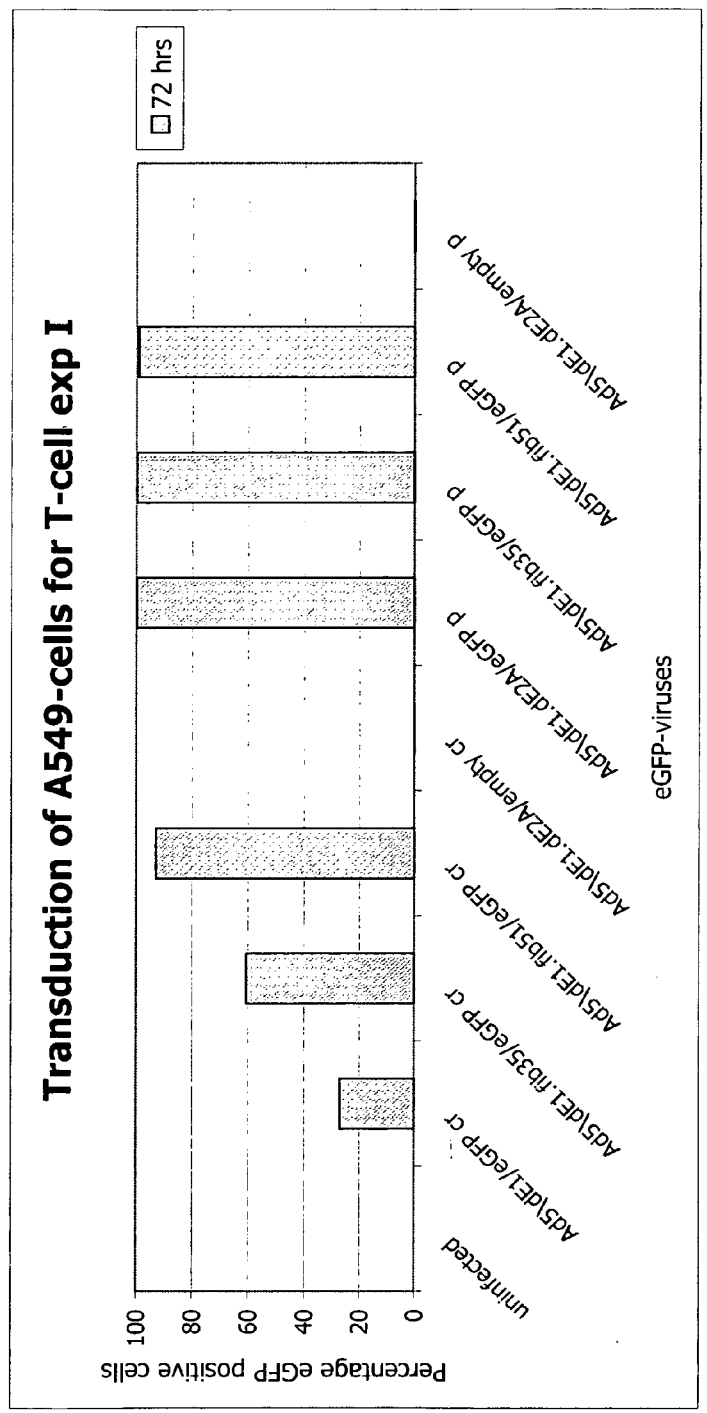
FIGS. 9A, B and C depict the flow cytometry results of transduced A549-, SupT1- and T-cells. A flow cytometer was used to determine the percentage of $eGFP^+$ cells for A549 (A) and SupT1 (B). The T-cells were first stained with CD3-PE, and then the percentage of $CD3^+eGFP^+$ T-cells was determined (C). (Percentages given are averages percentages of two wells.) Crude stands for crude lysate used as viruses, pure stands for purified viruses.

Infection of A549 cells (a human lung carcinoma cell-line) was taken along as an infection control. Herefore A549 cells were seeded in 24 well plates with a density of 2×10$^5$ cells/well and incubated in a humidified CO$_2$ incubator set at 37° C. and 10% CO$_2$. Medium used was DMEM containing 10% heat inactivated FBS. Next day, they were transduced in duplo with 11 different adenoviral vectors carrying the eGFP transgene. The MOI that was used varied from 250 till 2500 VP/cell (Table II) in a total volume of 300 μls. Cells with virus were centrifuged for 5 min at 1500 rpm and incubated in a humidified CO$_2$ incubator set at 37° C. and 10% CO$_2$. After 72 hours of incubation, the cells were transferred to tubes, washed with PBS containing 0.5% BSA by centrifugation, and resuspended in 200 μls of PBS with 0.5% BSA. The number of EGFP$^+$ cells was then determined using a flow cytometer (FIG. 9a).

II-3: Transduction of Human SupT1 Cells

Infection of SupT1 cells (a human T-cell-line) was taken along as a second infection control. Herefore SupT1 cells were seeded in 24 well plates with a density of 2×10$^5$ cells/well and incubated in a humidified CO$_2$ incubator set at 37° C. and 10% CO$_2$. Medium used was RPMI 1640 containing 10% heat inactivated FBS. Next they were transduced in duplo with 11 different adenoviral vectors carrying the eGFP transgene. The MOI that was used varied from 250 till 25000 VP/cell (Table II) in a total volume of 300 µls. Cells with virus were centrifuged for 5 min at 1500 rpm and incubated in a humidified $CO_2$ incubator set at 37° C. and 10% $CO_2$. After 72 or 96 hours (in experiment II and III after 48 hours) of incubation, the cells were transferred to tubes, washed with PBS containing 0.5% BSA by centrifugation, and resuspended in 200 µls of PBS with 0.5% BSA. The number of EGFP$^+$ cells was then determined using a flow cytometer (FIG. 9b).

II-4: Results

Clearly 2 out of 7 vectors tested as a PER.C6 or PER.C6.E2A adenoviral crude lysate show transduction levels varying from 3.78 to 16.43% eGFP positive CD3$^+$ T-lymphocytes (FIG. 9). Better transduction levels were obtained using 2 out of the 4 purified PER.C6 or PER.C6.E2A adenoviral vectors. Levels are varying from 14.86 to 66.34% eGFP positive CD3$^+$ T-lymphocytes. The adenoviral vectors with fibers of adenovirus serotype 35 and 51 are clearly positive for eGFP and thus, express the eGFP transgene. The adenoviral vector with the fiber of adenovirus serotype 5 (or fibers of serotype 40L and 45; data not shown) show undetectable levels of eGFP expression. A549-cells and SupT1-cells are well transduced with all used viruses.

Example 3

Transduction of Activated T-lymphocytes and Examining the Possible Effects of Transduction on the Activation Status of Naive T-lymphocytes.

III-1: Isolation and Transduction of Primary T-Lymphocytes

To determine the transduction efficiency of activated T-cells and the effects of transduction itself on the activation status of naive human T-lymphocytes, transductions were performed with chimaeric adenoviral vectors as described under Example 1. After transduction, the CD3$^+$ and or CD3$^+$CD69$^+$ cells were stained for expression of CD69, a marker for activated T-cells. First the CD3$^+$ T-lymphocytes were isolated from peripheral human blood, as described in Example 2. The percentage of CD3$^+$ cells was determined by staining the isolated cells with CD3 antibodies labelled with PE (Becton and Dickinson) and CD45 antibodies labelled with PerCp (Becton and Dickinson) followed by flow cytometric analysis, to see if the correct cells were isolated. The percentage of CD3$^+$ CD69$^+$ cells pretransduction, was determined by staining the isolated cells with CD3 antibodies labelled with PE (Becton and Dickinson) and CD69 antibodies labelled with APC (Becton and Dickinson) followed by flow cytometric analysis. This is done to determine the activation status of the cells before transduction and after treatment with T-lymphocyte mitogens that activate T-lymphocytes, such as concanavalin A. The CD3$^+$ T-lymphocytes activated or not were then cultured and transduced as described in Example 2. Control transductions included a human T-cell-line, SupT1. These transductions were performed in the same way as described in Example 2.

After 48, 72 or 96 hours of incubation, the cells were transferred to tubes, washed once with PBS containing 0.5% BSA by centrifugation. Washing was followed by incubation with anti CD3-antibodies labelled with PE (Becton and Dickinson) and CD69-antibodies labelled with APC (Becton and Dickinson) for 30 minutes on ice. The cells were then washed 2 times and resuspended in 200 µls of PBS with 0.5% BSA. The number of eGFP$^+$CD3$^+$ and the number of eGFP$^+$CD3$^+$CD69$^+$ T-lymphocytes was then determined using a flow cytometer.

Example 3

Adenoviral Transduction of Human Mature and Immature Mast Cells with Crude and Purified Vector Preparations.

IV-1: Isolation and Transduction of Mature and Immature Mast Cells

To determine the transduction efficiency on human mature and immature mast cells with chimaeric adenoviral vectors as described under Example 1, first CD34$^+$ progenitors were isolated from human peripheral blood using the Miltenyi Biotec magnetic beads. Mast cells were then cultured from these CD34$^+$ progenitors, according the method to culture cord blood derived mast cells, described by Saito et al (1996), but with some modifications. Mast cells were cultured for 3–5 weeks in medium containing Kit Ligand (KL, 100 ng/ml) and conditioned medium from the MCCM cell line (5–8% of a 20× serum free concentrate). The MCCM cell line is a haematopoietic cell line established from a mast cell culture from a healthy donor. The basal medium for mast cells is IMDM with supplements and 30% non heat inactivated FCS. Mast cells were cultured under conditions which allow the cells to remain immature or trigger them to become mature. For transduction of the mature (L16, 5 weeks old) and immature (BW, 3,5 weeks old) mast cells, the cells were plated in a 96-well plate at a density of $2.5 \times 10^4$ cells per well using mast cell medium and incubated in a humidified $CO_2$ incubator set at 37° C. and 5% $CO_2$ till transduction was performed.

Transduction was performed in triplicate with 8 different adenoviral vectors (Table III) carrying the eGFP transgene under the control of a CMV-promoter. The MOI that was used varied from 250 till 2500 VP/cell in a total volume of 200 µls for crude lysate and 120 µl for the purified adenoviral vector batches. Cells were incubated in a humidified $CO_2$ incubator set at 37° C. and 5% $CO_2$. Control transductions were performed with the human bronchial carcinoma cell-line A549.

TABLE III (Example 4): Compilation of viruses used in Example 4-IV-1. MOIs are given in virus particles (VP)/cell. Crude stands for crude lysates from adenoviral vector producing PER.C6 or PER.C6/E2A cells. Pure stands for viral vector purified through CsCl-banding.

| Virus | MOI (Vp/cell) |
|---|---|
| Uninfected | 0 |
| Ad5\dE1.dE2A.pIPspAdApt6/empty crude | 250, 1000, 2500 |
| Ad5\dE1.fib5.pIPspAdApt6/eGFP crude | 250, 1000, 2500 |
| Ad5\dE1.fib17.pAdApt/eGFP crude | 250, 1000, 2500 |
| Ad5\dE1.fib35.pAdApt/eGFP crude | 250, 1000, 2500 |
| Ad5\dE1.fib40L.pAdApt/eGFP crude | 250, 1000, 2500 |
| Ad5\dE1.fib45.pAdApt/eGFP crude | 250, 1000, 2500 |
| Ad5\dE1.fib51.pAdApt/eGFP crude | 250, 1000, 2500 |
| Ad5\dE1.dE2A.pIPspAdApt6/empty pure | 250, 1000, 2500 |
| Ad5\dE1.fib5.pIPspAdApt6/eGFP pure | 250, 1000, 2500 |
| Ad5\dE1.fib17.pAdApt/eGFP pure | 250, 1000, 2500 |
| Ad5\dE1.fib35.pAdApt/eGFP pure | 250, 1000, 2500 |
| Ad5\dE1.fib40L.pAdApt/eGFP pure | 250, 1000, 2500 |
| Ad5\dE1.fib45.pAdApt/eGFP pure | 250, 1000, 2500 |
| Ad5\dE1.fib51.pAdApt/eGFP pure | 250, 1000, 2500 |

Figure 11:
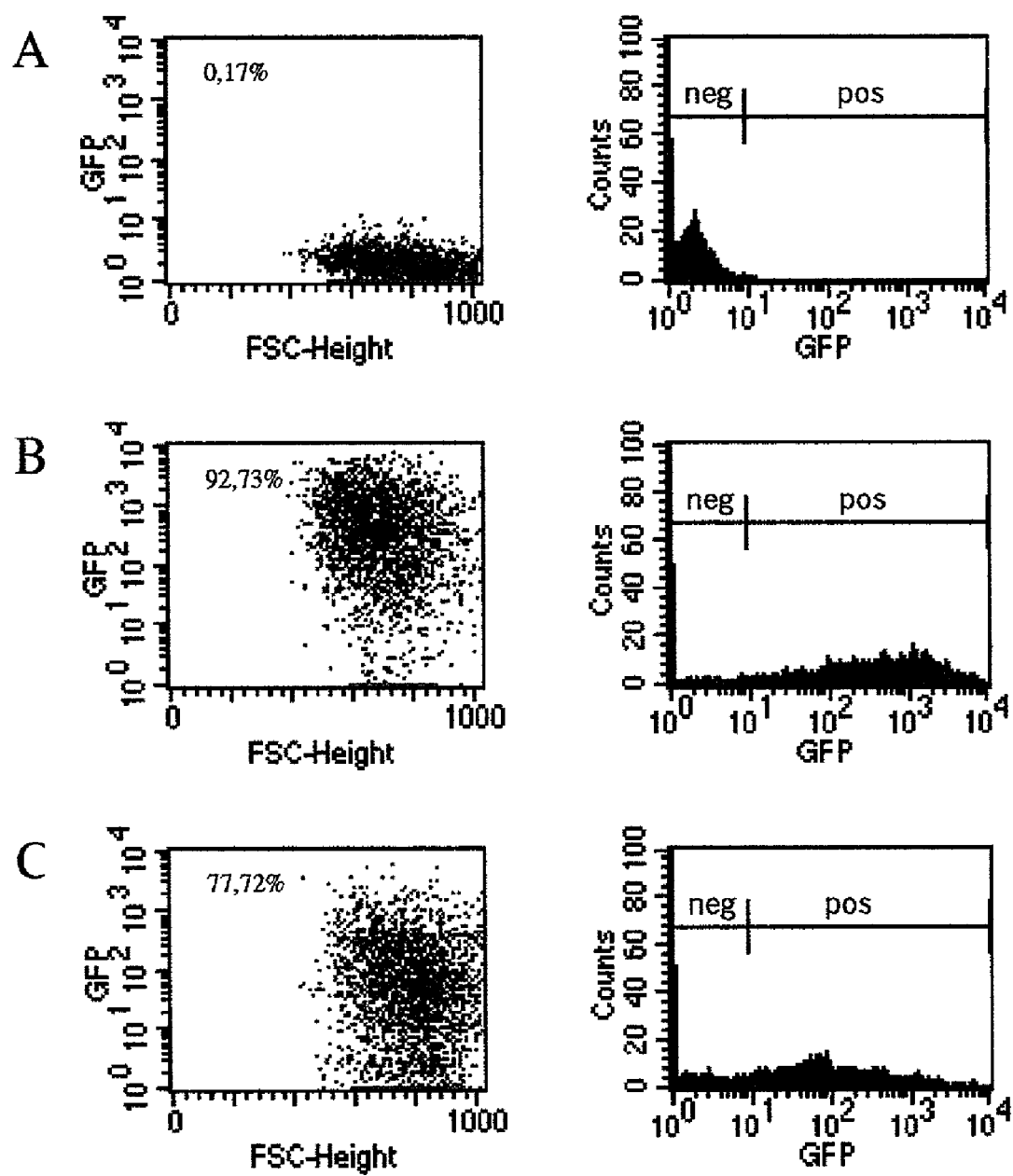
FIG. 11 shows an analysis of transduced mature (L16) and immature (BW) mast cells. The mast cells were harvested 96 hours after transduction, followed by flow cytometry analysis to determine the percentage of $eGFP^+$ mast cells. Percentages given are percentages of $eGFP^+$ cells. Mature mast cells transduced with
Ad5\dE1.dE2A.pIPspAdApt6/empty crude MOI 250 (A),
Ad5\dE1.fib51.pAdApt/eGFP crude MOI 250 (B) and
   Ad5\dE1.fib51.pAdApt/eGFP pure MOI 250 (C). Immature mast cells transduced with
Ad5\dE1.dE2A.pIPspAdApt6/empty crude MOI 250 (D),
Ad5\dE1.fib51.pAdApt/eGFP crude MOI 250 (E) and
   Ad5\dE1.fib51.pAdApt/eGFP pure MOI 250 (F).
Figure 11:
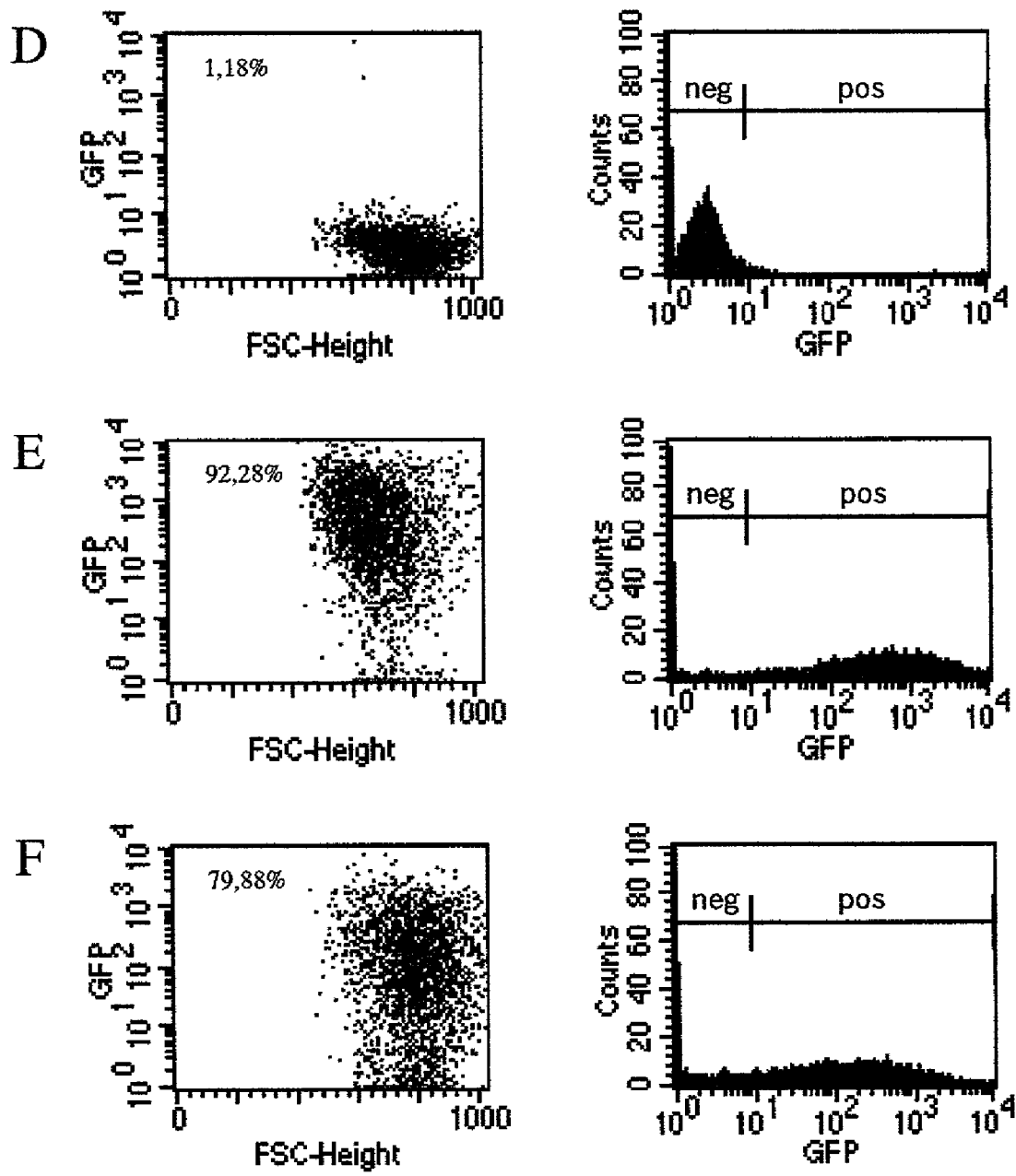

After 24, 48 and 72 hours of incubation, the cells were scored for eGFP expression using the fluorescent microscope (Table IVA and B). Pictures were taken from the two different cell-types transduced with different adenoviral vectors (FIG. 10). After 96 hours of incubation, the cells from only one well were transferred to tubes and washed once with PBS by centrifugation. The cells were then resuspended in 250 µls of PBS. The number of eGFP$^+$ mature and immature mast cells was then determined using a flow cytometer (FIGS. 11 and 12). Samples that were analysed were mature (L16) and immature (BW) mast cells transduced with crude lysate and purified batches of the following adenoviral vectors:
Ad5\dE1.dE2A.pIPspAdApt6/empty,
Ad5\dE1.fib5.pIPspAdApt6/eGFP,
Ad5\dE1.fib35.pAdApt/eGFP, and Ad5\dE1.fib51.pAdApt/eGFP.

IV-2: Transduction of Human A549 Cells

Infection of A549 cells (a human lung carcinoma cell-line) was taken along as a positive infection control. Here fore A549 cells were seeded in 96-well plates with a density of $1 \times 10^4$ cells/well and incubated in a humidified $CO_2$ incubator set at 37° C. and 10% $CO_2$ till transduction was performed. Medium used was DMEM containing 10% heat inactivated FBS. Transduction was performed in triplicate with 8 different adenoviral vectors (Table III) carrying the eGFP transgene under the control of a CMV-promoter. The MOI that was used was 1000 VP/cell in a total volume of 200 μls for crude lysate adenoviral vector batches and 120 μl for the purified adenoviral vector batches. Cells were incubated in a humidified $CO_2$ incubator set at 37° C. and 10% $CO_2$.

After 24, 48 and 72 hours of incubation, the cells were scored for eGFP expression using the fluorescent microscope (Table IVC).

IV-3: Results Transduction

Clearly 3 out of 8 vectors tested as a PER.C6 or PER.C6.E2A crude lysate adenoviral vectors show high transduction levels. For mature (L16) mast cells, transduction levels are varying from 49.72 to 95.15% and for immature (BW) mast cells from 65.85 to 92.28% eGFP positive cells. Same transduction levels were obtained using 2 out of the 7 purified PER.C6 or PER.C6.E2A adenoviral vectors. For mature mast cells transduction levels are varying from 76.70 to 95.99% and for immature mast cells from 79.09 to 90.87% eGFP positive cells. The adenoviral vectors with fibers of adenovirus serotype 35 and 51 are clearly positive for eGFP and thus, express the eGFP transgene. The adenoviral vectors with the fibers of adenovirus serotype 5, 17, 40L and 45 show very low levels of eGFP expression. A549-cells are well transduced with all used viruses.

IV-4: β-Hexoseaminidase Assay

To determine the effect of the chimaeric adenoviral vectors on the functionality of the mast cells, a β-hexoseaminidase assay was performed. This assay is used to determine whether the cells are still able to become activated and to release its inflammatory mediators from its granules.

For transduction of the mature (L20, 5 weeks old) and immature (BW, 12 weeks old) mast cells, the cells were plated in a 24-well plate at a density of $1 \times 10^5$ cells per well using mast cell medium and incubated in a humidified $CO_2$ incubator set at 37° C. and 5% $CO_2$ till transduction was performed. Transduction was performed in quadruplicate with crude lysate of Ad5\dE1.fib51.pAdApt/eGFP and Ad5\dE1.dE2A.dE3(Xba).TeTOE4.fib51.pIPspAdApt6/eGFP at MOI 250, 1000 and 2500 VP/cell and Ad5\dE1.dE2A.pIPspAdApt6/empty at an MOI of 2500 VP/cell in a total volume of 1 ml. Cells were incubated in a humidified $CO_2$ incubator set at 37° C. and 5% $CO_2$.

After 48 hours of incubation, the cells were scored for eGFP expression using the fluorescent microscope (Table V). After scoring for eGFP, the β-hexoseaminidase assay was performed. The transduced mature (L20) and immature (BW) mast cells in the 24-well plate were sensitised with IgE specific to tri-nitrophenol (TNP) from the murine hybridoma IgELA2 (ATCC cat# TIB142). Then the cells were washed twice in activation buffer consisting of IMDM+ 0.5% BSA+100 ng/ml KL, followed by plating in 96-well plates at a density of $5 \times 10^{3-1 \times 10^4}$ cells per well. The TNP-BSA antigen was added at two different concentrations, 1 and 10 ng/ml followed by incubation at 37° C. and 5% $CO_2$ for 30 minutes. The supernatant from the cells was transferred to a new 96 well plate and the release of β-hexoseaminidase will be measured. β-hexoseaminidase activity is measured using substrate 4-nitrophenyl-2-acetamido-2-deoxy-B-D-glucopyranoside. After 90 minutes incubation in citrate buffer, glycine is added and absorbance is measured at 405 nm (FIGS. 13A and B). As positive controls, both mature (L20) and immature (BW) mast cells that were taken freshly from a culture-flask before performing the assay were taken along.

TABLE IV (Example 4): Results of the eGFP scoring using the fluorescent microscope. Crude stands for crude lysates from adenoviral vector producing PER.C6 or PER.C6/E2A cells. Pure stands for viral vector purified through CsCl-banding.

| | A Mature Mast cells | | | | | | B Immature Mast cells | | | | | | C A549 cells | |
|---|---|---|---|---|---|---|---|---|---|---|---|---|---|---|
| | Crude | | | pure | | | Crude | | | pure | | | crude | pure |
| MOI (VP/ml) | 250 | 1000 | 2500 | 250 | 1000 | 2500 | 250 | 1000 | 2500 | 250 | 1000 | 2500 | 1000 | 1000 |
| Empty | − | − | − | − | − | − | − | − | − | − | − | − | − | − |
| Fib 5 | +/−− | +/−− | +/−− | +/−− | +/− | +/− | − | +/−− | +/−− | +/−− | +/− | +/−− | ++ | +++ |
| Fib 17 | − | − | − | − | − | +/− | − | − | − | − | − | +/−− | + | + |
| Fib 35 | ++ | +++ | +++ | ++ | +++ | +++ | + | +++ | +++ | + | ++ | ++ | +++ | +++ |
| Fib 40L | − | − | +/−− | NA | NA | NA | − | − | +/−− | NA | NA | NA | ++ | NA |
| Fib 45 | − | − | +/−− | − | − | +/−− | − | − | − | − | +/−− | +/− | +/− | |
| Fib 51 | +++ | +++ | +++ | ++ | +++ | +++ | ++ | +++ | +++ | ++ | ++ | ++ | +++ | +++ |

−: no eGFP positive cells,
+/−−: less than 1% eGFP positive cells,
+/−: about 10% eGFP positive cells,
++/−: about 25% eGFP positive cells,
+: about 50% eGFP positive cells,
++: about 75% eGFP positive cells,
+++: 90 to 100% eGFP positive cells
NA: not applicable IV-5: Results β-Hexoseaminidase Assay Clearly the Ad5\dE1.fib51.pAdApt/eGFP crude lysate as an adenoviral vector shows again good transduction levels. For mature (L20) mast cells, transduction levels are ranging from 20% eGFP positive cells for MOI 250, 36% for MOI 1000 and 70% for MOI2500. For immature (BW) mast cells, transduction levels are ranging from 33% eGFP positive cells for MOI 250, 50% for MOI 1000 and 80% for MOI2500.

The level of activation of infected cells and not infected cells at any of the MOIs is comparable. The overall level of activation in the immature (BW) mast cells is lower than the level of activation of the mature (L20) mast cells. This is explained by the fact that the immature mast cell culture is much older. For some reason, TNP at a concentration of 1 ng/ml gives a higher percentage release than TNP at a concentration of 10 ng/ml. This may also be explained by the fact that the immature mast cell culture is much older and is giving a lower level of activation overall. The virus is not toxic to the cells and it is not influencing the level of activation of both the mature and the immature mast cells.

TABLE V (Example 4): Results of the eGFP scoring using the fluorescent microscope.

|  | Mature Mast cells | Immature Mast cells |
| --- | --- | --- |
| Empty | − | − |
| Fib 51 MOI 250 | ++/− | ++/− |
| Fib 51 MOI 1000 | + | ++/− |
| Fib 51 MOI 2500 | ++ | ++ |

−: no eGFP positive cells,
+/−−: less than 1% eGFP positive cells,
+/−: about 10% eGFP positive cells,
++/−: about 25% eGFP positive cells,
+: about 50% eGFP positive cells,
++: about 75% eGFP positive cells,
+++: 90 to 100% eGFP positive cells Example 5

Adenoviral Transduction of the Human Ramos B-Cell-Line with Crude and Purified Vector Preparations.

V-1: Transduction of the Human Ramos B-Cell-Line

To determine the transduction efficiency, the human Ramos B-cell-line was transduced with chimaeric adenoviral vectors as described under Example 1. The normal medium for the Ramos B-cells is RPMI1640 supplemented with 10% heat inactivated FBS and 1×.Penicillin/Streptomycin/Glutamine (Gibco BRL). The cells were cultured in a humidified $CO_2$ incubator at 37° C. and 5% $CO_2$. For transduction of the Ramos B-cells, the cells were plated in a 96-well plate at a density of $2.0 \times 10^4$ cells per well using three different kinds of medium, the normal culture medium, the normal culture medium supplemented with 10 ng/ml hIL4 and 0.5 µg/ml α-CD40 (activation medium), or Optimem (Gibco BRL). The same day, transduction was performed in duplicate with 4 different adenoviral vectors (Table VI) carrying the eGFP transgene under the control of a CMV-promoter. The MOI that was used varied from 250 till 25000 VP/cell in a total volume of 130 µl. The next day the Optimem medium was replaced by 150 µl normal culture medium. Control transduction was performed with the human T-cell-line SupT1.

TABLE VI (Example 5): Compilation of viruses used in Example 5-V-1. MOIs are given in virus particles (VP)/cell. Crude stands for crude lysates from adenoviral vector producing PER.C6 or PER.C6/E2A cells. Pure stands for viral vector purified by CsCl-banding.

| Virus | MOI (Vp/cell) |
| --- | --- |
| Uninfected | 0 |
| Ad5\dE1.dE2A.pIPspAdApt6/empty crude | 250, 1000, 2500, 25000 |
| Ad5\dE1.fib5.pIPspAdApt6/eGFP crude | 250, 1000, 2500, 25000 |
| Ad5\dE1.fib51.pAdApt/eGFP crude | 250, 1000, 2500, 25000 |
| Ad5\dE1.fib51.pAdApt/eGFP pure | 250, 1000, 2500, 25000 |
| Ad5\dE1.dE2A.dE3(Xba)fib51.pIPspAdApt6/eGFP crude | 250, 1000, 2500, 25000 |

V-2: Transduction of Human SupT1 Cells

Infection of SupT1 cells was taken along as an infection control. SupT1 cells were seeded in 96-well plates with a density of $3.0 \times 10^4$ cells/well and incubated in a humidified $CO_2$ incubator at 37° C. and 10% $CO_2$. Medium used was RPMI1640 containing 10% heat inactivated FBS. The same day, transduction was performed in duplicate with 5 different adenoviral vectors (Table VI) carrying the eGFP transgene. The MOIs used were 250 and 2500 VP/cell in a total volume of 130 µl.

V-3: Determination of the Percentage eGFP$^+$ Cells

Figure 14:
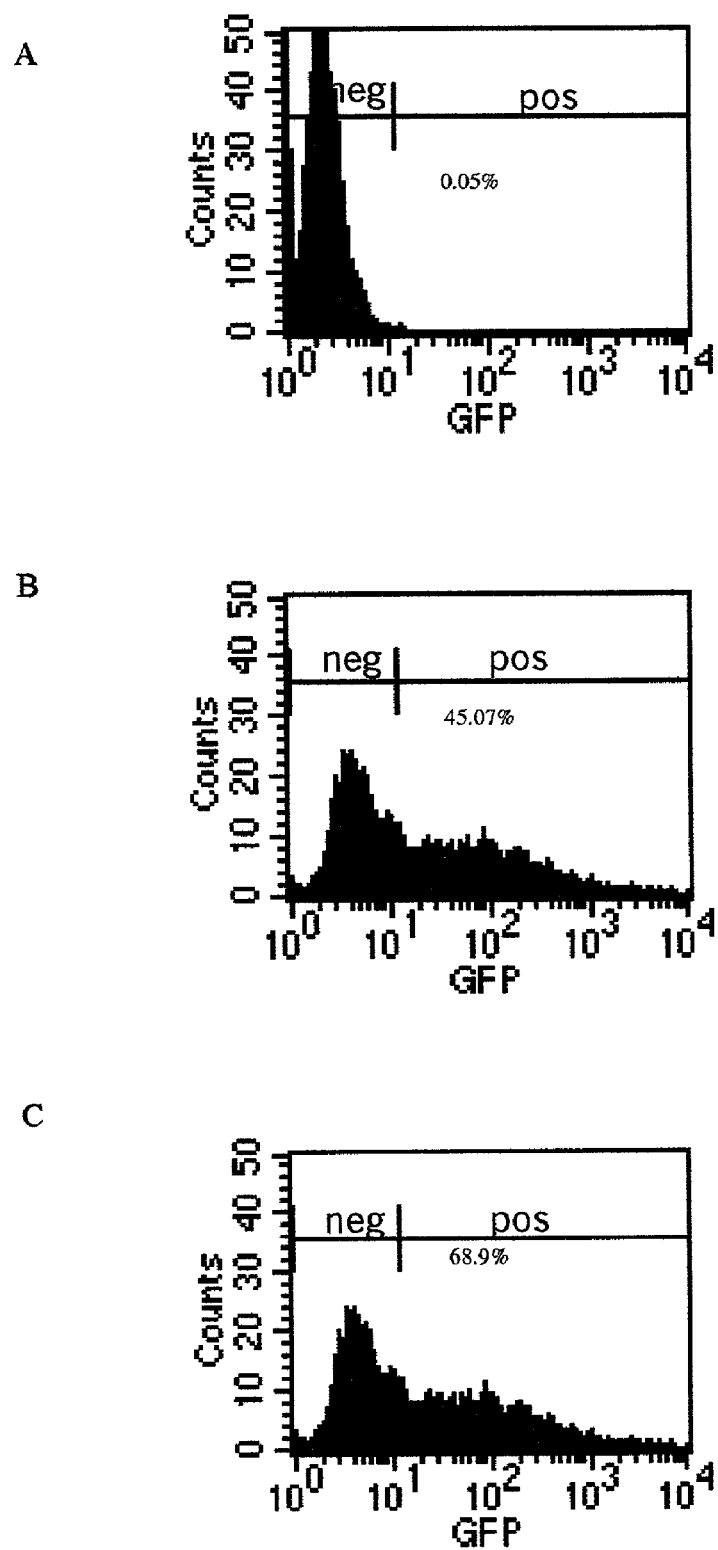
FIGS. 14A–C show the analysis of transduced Ramos B-cells described in Example 5. The B-cells were harvested one week after transduction, followed by flow cytometry analysis to determine the percentage of $eGFP^+$ cells. Ramos B-cells transduced with normal culture medium and Ad5\dE1.dE2A.pIPspAdApt6/empty crude MOI 25000 (A), Ad5\dE1.fib51.pAdApt/eGFP crude MOI 25000 (B) and Ad5\dE1.fib51.pAdApt/eGFP pure MOI 25000 (C).
Figure 15:
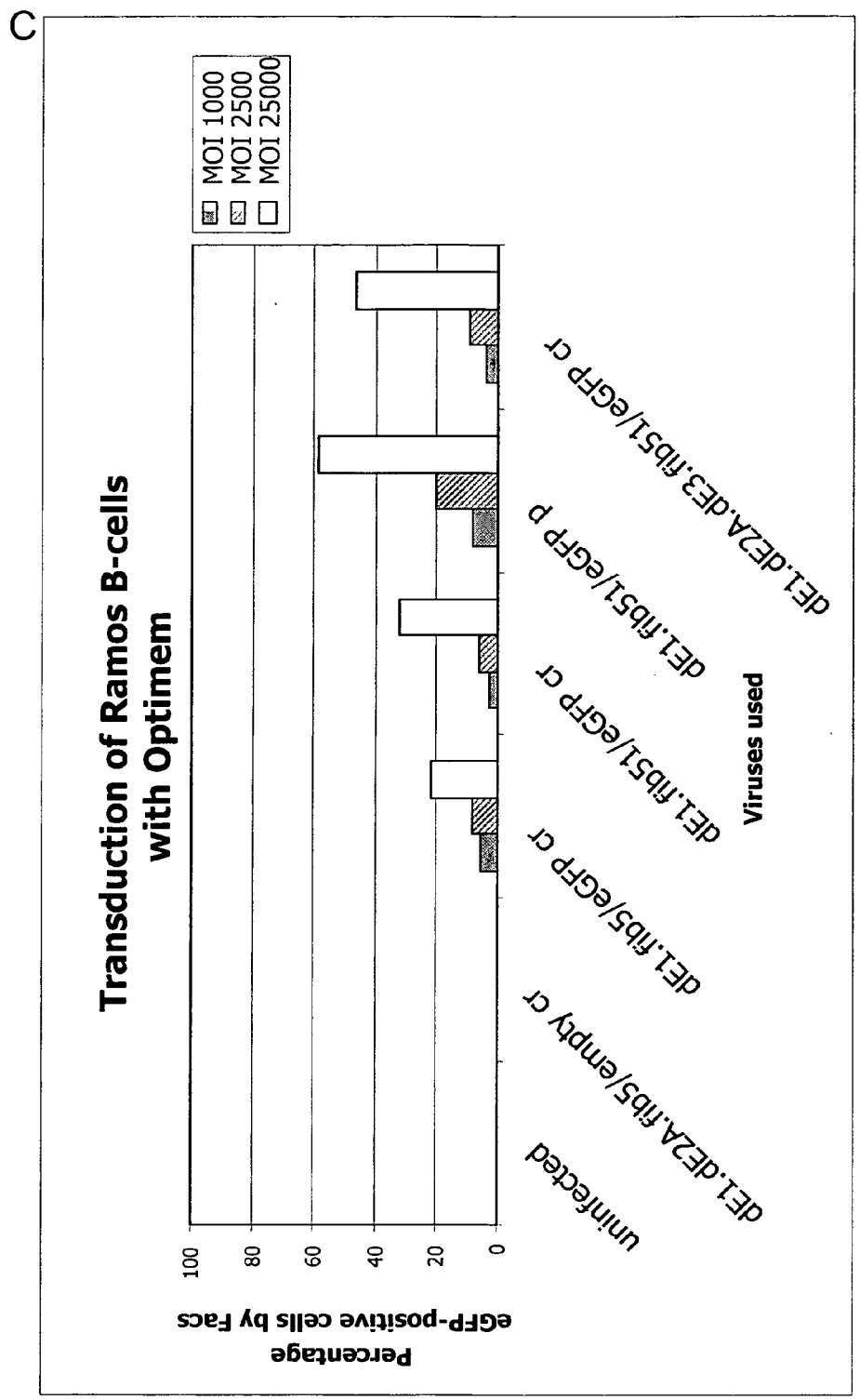
FIGS. 15A–D show the flow cytometry results of transduced Ramos B-cells and SupT1 cells described in Example 5. One week after transduction, the cells were harvested and a flow cytometer was used to determine the percentage of $eGFP^+$ cells for Ramos B-cells transduced with normal culture medium (A), with activation medium (B), Optimem (C) and SupT1 cells (D). Cr stands for crude lysate adenoviral vectors and P stands for purified adenoviral vectors. MOI is in VP/cell.
Figure 15:
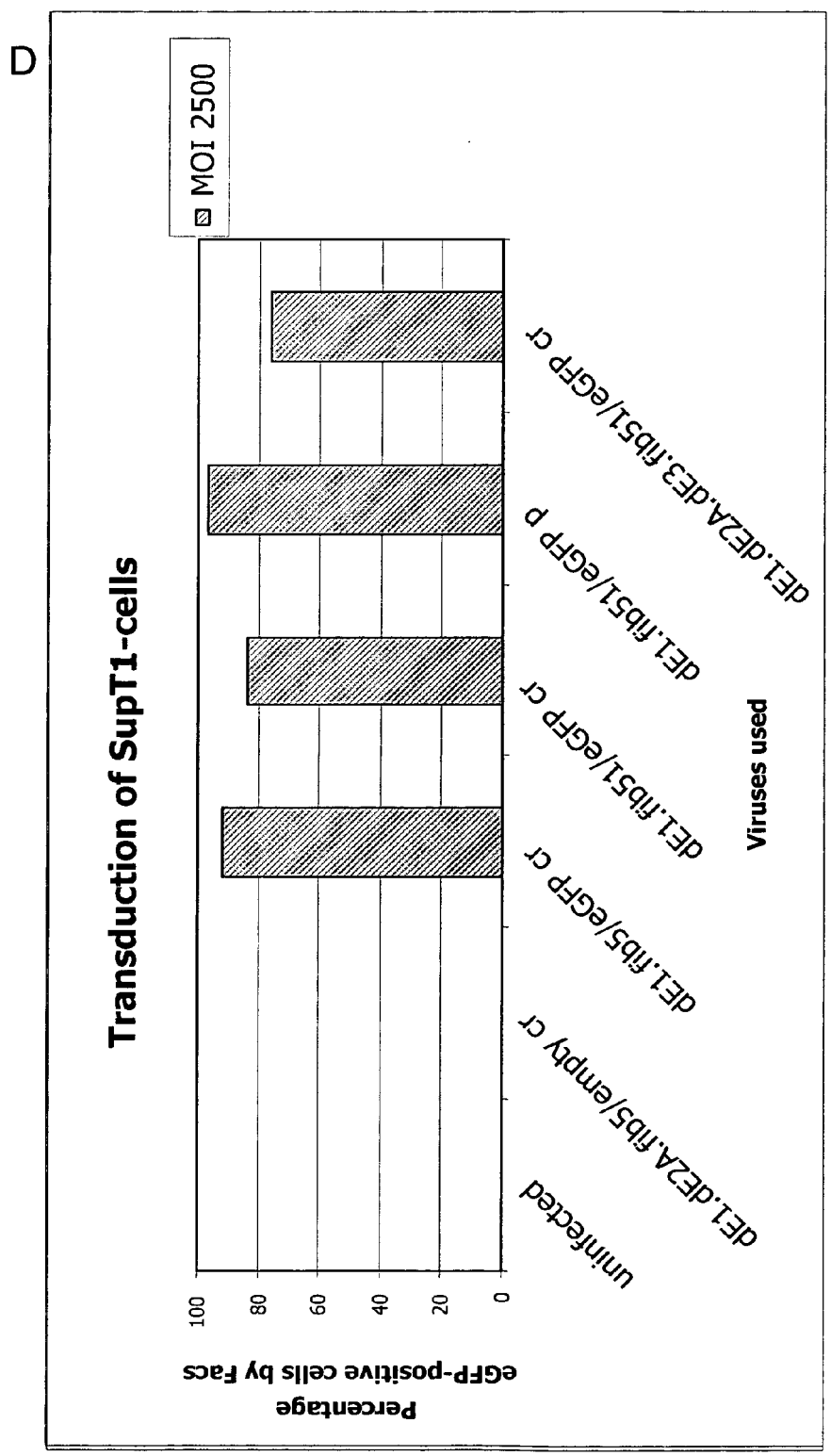

Transduced cells were scored for eGFP-expression after one-week incubation. The cells from two wells transduced with the same MOI were pooled, transferred to tubes and washed once with PBS. The cells were then resuspended in 250 µl of PBS. (For the SupT1 cells only MOI 2500 was used in the FACS-experiment.) The number of eGFP$^+$ Ramos B-cells and SupT1 cells were determined using a flow cytometer (FIGS. 14 and 15).

Clearly 2 out of 5 vectors tested, Ad5\dE1.fib51.pAdApt/eGFP crude and pure and Ad5\dE1.dE2A.dE3(Xba)fib51.pIPspAdApt6/eGFP crude, showed good transduction levels. Transduction levels of these three vectors on Ramos B-cells with normal culture medium are ranging from 45.07 to 68.9%, with activation medium from 49.44 to 76.47% and with Optimem from 32.08 to 58.57% eGFP-positive cells. The adenoviral vectors with the fiber of adenovirus serotype 51 are clearly positive for eGFP. The commonly used adenoviral vector Ad5 shows very low levels of eGFP expression. SupT1 cells Overall Tropism of Chimeric Ad5/35 and Ad5/51 Relative to Adenovirus Serotype 5

The chimeric vectors Ad5/Ad51 and Ad5/Ad35 described herein bind to and infect the T cells, B cells and/or mast cells more effectively than the native adenovirus serotype 5. The above examples show that the chimera tropism for such cells is much greater than adenovirus 5 is both crude and purified virus preparations. This relationship is evident for MOI ranging from 250 to 25000.

Purified Ad5/Ad35 at a MOI of from 2500 to 25000 transduces about 40% to 66% of T cells. Purified Ad5/Ad51 at a MOI of from 2500 to 25000 transduces about 35% to 53% of T cells. In contrast, Ad5 at a MOI of 2500 to 25000 transduces about 3% of T cells.

Purified Ad5/Ad35 at a MOI of from 250 to 2500 transduces about 75% to 100% of mature mast cells. Purified Ad5/Ad51 at a MOI of from 250 to 2500 transduces about 75% to 100% of mature mast cells. Ion contrast, purified Ad5 at these MOI transduces only about 5 to 25% of mature mast cells.

Purified Ad5/Ad35 at a MOI of from 250 to 2500 transduces about 50% to 75% of immature mast cells Purified Ad5/Ad51 at a MOI of from 250 to 2500 transduces about 75% of immature mast cells. In contrast, purified Ad5 at these MOI transduce only about 8 to 25% of immature mast cells.

Purified Ad5/Ad51 at a MOI of from 2500 to 25000 transduces about 27% to 77% of Ramos B cell line B cells. Crude Ad5/Ad51 at a MOI of from 2500 to 25000 transduces about 15% to 45% of Ramos B cell line B cells. In contrast, crude Ad5 at these MOI transduces only about 15 to 20% of Ramos B cell line B cells.

Summary of transduction efficiency of Ad5, Ad5/Ad35, and Ad5/Ad51 fibers on T cells, mast cells, and B cells

|  |  | T cells | Mast cells Mature | Mast cells Immature | (Ramos) cells |
|---|---|---|---|---|---|
| Purified adenovirus | | | | | |
| MOI 250 | Ad5 | | 6% | 9% | |
| | Ad5/Ad35 | | 75% | 50% | |
| | Ad5/Ad51 | | 75% | 75% | |
| MOI 2500 | Ad5 | 3% | 25% | 25% | |
| | Ad5/Ad35 | 40% | 95% | 90% | |
| | Ad5/Ad51 | 32% | 95% | 90% | 27% |
| MOI 25000 | Ad5 | — | | | |
| | Ad5/Ad35 | 66% | | | |
| | Ad5/Ad51 | 53% | | | 77% |
| Crude adenovirus | | | | | |
| MOI 250 | Ad5 | | 5 | 8% | |
| | Ad5/Ad35 | | 75 | 85% | |
| | Ad5/Ad51 | | 90 | 92% | |
| MOI 2500 | Ad5 | 1% | 28 | 25% | 15% |
| | Ad5/Ad35 | 9% | 95 | 90% | |
| | Ad5/Ad51 | 17% | 90 | 90% | 15% |
| MOI 25000 | Ad5 | | | | 20% |
| | Ad5/Ad35 | | | | |
| | Ad5/Ad51 | | | | 45% |

REFERENCES

Abbas, A. K., Lichtman, A. H. and Pober, J. S. (1991) Cellular and Molecular Immunology. esp pag. 15–16

Amberg, N., Mei, Y. and Wadell, G. (1997) Fiber genes of adenoviruses with tropism for the eye and the genital tract. Virology 227: 239–244.

Bergelson, J. M., Cunningham, J. A., Droguett, G., Kurt-Jones, E. A., Krithivas, A., Hong, J. S., Horwitz, M. S., Crowell, R. L. and Finberg, R. W. (1997) Isolation of a common receptor for coxsackie B virus and adenoviruses 2 and 5. Science 275: 1320–1323.

Bout, A. (1997) Gene therapy, p. 167–182. In: D. J. A. Crommelin and R. D. Sindelar (ed.), Pharmaceutical Biotechnology, Harwood Academic Publishers.

Bout, A. (1996) Prospects for human gene therapy. Eur. J. Drug Met. and Pharma. 2, 175–179.

Blaese, M., Blankenstein, T., Brenner, M., Cohen-Hagenauer, O., Gansbacher, B., Russel, S., Sorrentino, B. and Velu, T. (1995) Cancer Gene Ther. 2: 291–297.

Brody, S. L. and Crystal, R. G. (1994) Adenovirus mediated in vivo gene transfer. Ann. N. Y. Acad. Sci. 716: 90–101.

Carter, A. J., Laird, J. R., Farb, A., Kufs, W., Wortham, D. C. and Virmani, R. (1994) Morphologic characteristics of lesion formation and time course of smooth muscle cell proliferation in a porcine proliferative restenosis model. J. Am. Coll. Cardiol. 24: 1398–1405.

Castell, J. V., Hernandez, D., Gomez-Foix, A. M., Guillen, I, Donato, T. and Gomez-Lechon, M. J. (1997) Adenovirus-mediated gene transfer into human hepatocytes: analysis of the biochemical functionality of transduced cells. Gene Ther. 4(5): 455–464

Chroboczek, J., Ruigrok, R. W. H., and Cusack, S. (1995) Adenovirus fiber, p. 163–200. In: W. Doerfler and P. Böhm (eds.), The molecular repertoire of adenoviruses I. Springer-Verlag, Berlin.

Defer, C., Belin, M., Caillet-Boudin, M. and Boulanger, P. (1990) Human adenovirus-host cell interactions; comparative study with members of subgroup B and C. Journal of Virology 64(8): 3661–3673.

Fallaux, F. J., Bout, A., van der Velde, I. et al. (1998) New helper cells and matched E1-deleted adenovirus vectors prevent generation of replication competent adenoviruses. Human Gene Therapy 9: 1909–1917.

Francki, R. I. B., Fauquet, C. M., Knudson, D. L. and Brown, F. (1991) Classification and nomenclature of viruses. Fifth report of the international Committee on taxonomy of viruses. Arch. Virol. Suppl. 2: 140–144.

Gall, J., Kass-Eisler, A., Leinwand, L. and Falck-Pedersen, E. (1996) Adenovirus type 5 and 7 capsid chimera: fiber replacement alters receptor tropism without affecting primary immune neutralization epitopes. Journal of Virology 70(4): 2116–2123.

Greber, U. F., Willets, M., Webster, P., and Helenius, A. (1993) Stepwise dismanteling of adenovirus 2 during entry into cells. Cell 75: 477–486.

Herz, J. and Gerard, R. D. (1993) Adenovirus-mediated transfer of low density lipoprotein receptor gene acutely accelerates cholesterol clearence in normal mice. Proc. Natl. Acad. Sci. U.S.A. 96: 2812–2816.

Hierholzer, J. C. (1992) Adenovirus in the immunocompromised host. Clin. Microbiol Rev. 5: 262–274.

Hierholzer, J. C., Wigand, R., Anderson, L. J., Adrian, T., and Gold, J. W. M. (1988) Adenoviruses from patients with AIDS: a plethora of serotypes and a description of five new serotypes of subgenus D (types 43–47). J. Infect. Dis. 158: 804–813.

Hong, S. S., Karayan, L., Tournier, J., Curiel, D. T. and Boulanger, P. A. (1997) Adenovirus type 5 fiber knob binds to MHC class I (2 domain at the surface of human epithelial and B lymphoblastoid cells. EMBO J. 16: 2294–2306.

Hsu, K. H., Lonberg-Holm, K., Alstein, B. and Crowell, R. L. (1988) A monoclonal antibody specific for the cellular receptor for the group B coxsackieviruses. J. Virol 62(5): 1647–1652.

Huard, J., Lochmuller, H., Acsadi, G., Jani, A., Massie, B. and Karpati, G. (1995) The route of administration is a major determinant of the transduction efficiency of rat tissues by adenoviral recombinants. Gene Ther. 2: 107–115.

Imperiale, M. J., Akusjnarvi, G. and Leppard, K. N. (1995) Post-transcriptional control of adenovirus gene expression, P139–171. In: W. Doerfler and P. Böhm (eds.), The molecular repertoire of adenoviruses I. Springer-Verlag Berlin.

Ishibashi, M. and Yasue, H. (1984) The adenoviruses, H. S. Ginsberg, ed., Plenum Press, Londen, N.Y. Chapter 12: 497–561.

Jaffe, E. A., Nachman, R. L., Becker, C. G., Minick, C. R. (1973) Culture of endothelial cells derived from umbilical veins. Identification by morphologic and immunologic criteria. J. Clin. Invest. 52: 2745–2756.

Kass-Eisler, A., Falck-Pederson, E., Elfenbein, D. H., Alvira, M., Buttrick, P. M. and Leinwand, L. A. (1994) The impact of developmental stage, route of administration and the immune system on adenovirus-mediated gene transfer. Gene Ther. 1: 395–402.

Khoo, S. H., Bailey, A. S., De Jong, J. C., and Mandal, B. K. (1995) Adenovirus infections in human immunodeficiency virus-positive patients: Clinical features and molecular epidemiology. J. Infect. Dis 172: 629–637.

Kidd, A. H., Chroboczek, J., Cusack, S., and Ruigrok, R. W. (1993) Adenovirus type 40 virions contain two distinct fibers. Virology 192: 73–84.

Krasnykh, V. N., Mikheeva, G. V., Douglas, J. T. and Curiel, D. T. (1996) Generation of recombinant adenovirus vectors with modified fibers for altering viral tropism. J. Virol. 70(10): 6839–6846.

Krasnykh, V. N., Dmitriev, I., Mikheeva, G., Miller, C. R., Belousova, N. and Curiel, D. T. (1998) Characterization of an adenovirus vector containing a heterologous peptide epitope in the HI loop of the fiber knob. J. Virol. 72(3): 1844–1852.

Law, L., Chillon, M., Bosch, A., Armentano, D., Welsh, M. J. and Davidson, B. L. (1998) Infection of primary CNS cells by different adenoviral serotypes: Searching for a more efficient vector. Abstract 1$^{st}$ Annual Meeting American Society of Gene Therapy, Seattle, Wash.

Leppard, K. N. (1997) E4 gene function in adenovirus, adenovirus vector and adeno-associated virus infections. J. Gen. Virol. 78: 2131–2138.

Lloyd Jones, D. M. and Bloch, K. D. (1996) The vascular biology of nitric oxide and its role in atherogenesis. Annu. Rev. Med. 47: 365–375.

Miltenyi, S., Muller, W., Weichel, W. and Radbruch, A. (1990) High gradient magnetic cell separation with MACS. Cytometry 11(2): 231–8.

Morgan, C., Rozenkrantz, H. S., and Mednis, B. (1969) Structure and development of viruses as observed in the electron microscope.X. Entry and uncoating of adenovirus. J. Virol 4: 777–796.

Roelvink, P. W., Kovesdi, I. and Wickham, T. J. (1996) Comparative analysis of adenovirus fiber-cell interaction: Adenovirus type 2 (Ad2) and Ad9 utilize the same cellular fiber receptor but use different binding strategies for attachment. J. Virol. 70: 7614–7621.

Roelvink, P. W., Lizonova, A., Lee, J. G. M., Li, Y., Bergelson, J. M., Finberg, R. W., Brough, D. E., Kovesdi, I. and Wickham, T. J. (1998) The coxsackieadenovirus receptor protein can function as a cellular attachment protein for adenovirus serotypes from subgroups A, C, D, E, and F. J. Virol. 72: 7909–7915.

Rogers, B. E., Douglas J. T., Ahlem, C., Buchsbaum, D. J., Frincke, J. and Curiel, D. T. (1997) Use of a novel cross-linking method to modify adenovirus tropism. Gene Ther. 4: 1387–1392.

Saito, H., Ebisawa, M., Tachimoto, H., Shichijo, M., Fukagawa, K., Matsumoto, K., Iikura, Y., Awaji, T., Tsujimoto, G., Yanagida, M., Uzumaki, H., Takahashi, G., Tsuji, K. and Nakahata, T. (1996) Selective growth of human mast cells induced by Steel factor, IL2, and prostaglandin E2 from cord blood mononuclear cells. Journal of Immunology 157: 343–350

Schulick, A. H., Vassalli, G., Dunn, P. F., Dong, G., Rade, J. J., Zamarron, C. and Dichek, D. A. (1997) Established immunity precludes adenovirus-mediated gene transfer in rat carotid arteries.

Schnurr, D and Dondero, M. E. (1993) Two new candidate adenovirus serotypes. Intervirol. 36: 79–83.

Schwartz, R. S., Edwards, W. D., Huber, K. C., Antoniudes, L. C. Bailey, K. R., Camrud, A. R., Jorgenson, M. A. and Holmes, D. R. Jr. (1993) Coronary restenosis: Prospects for solution and new perspectives from a porcine model. Mayo Clin. Proc. 68: 54–62.

Shi, Y., Pieniek, M., Fard, A., O'Brien, J., Mannion, J. D. and Zalewski, A. (1996) Adventitial remodelling after coronary arterial injury. Circulation 93: 340–348.

Shabram, P. W., Giroux, D. D., Goudreau, A. M., Gregory, R. J., Horn, M. T., Huyghe, B. G., Liu, X., Nunnally, M. H., Sugarman, B. J. and Sutjipto, S. (1997) Analytical anion-exchange HPLC of recombinant type-5 adenoviral particles. Hum. Gene Ther. 8(4): 453–465.

Signas, G., Akusjarvi, G., and Petterson, U. (1985) Adenovirus 3 fiberpolypeptide gene: Complications for the structure of the fiber protein. J. Virol. 53: 672–678.

Stevenson, S. C., Rollence, M., White, B., Weaver, L. and McClelland, A., (1995) Human adenovirus serotypes 3 and 5 bind to two different cellular receptors via the fiber head domain. J. Virol 69(5): 2850–2857.

Stevenson, S. C., Rollence, M., Marshall-Neff, J. and McClelland, A. (1997) Selective targeting of human cells by a chimaeric adenovirus vector containing a modified fiber protein. J. Virology 71(6): 4782–4790.

Stouten, P. W. F., Sander, C., Ruigrok, R. W. H., and Cusack, S. (1992) New triple helical model for the shaft of the adenovirus fiber. J. Mol. Biol. 226: 1073–1084.

Svensson, V. and Persson, R. (1984) Entry of adenovirus 2 into Hela cells. J. Virol. 51: 687–694.

Van der Vliet, P. C. (1995) Adenovirus DNA replication. In: W. Doerfler and P. Böhm (eds.), The molecular repertoire of adenoviruses II. Springer-Verlag, Berlin.

Varga, M. J., Weibull, C., and Everitt, E. (1991) Infectious entry pathway of adenovirus type 2. J. Virol 65: 6061–6070.

Varenne, O., Pislaru, S., Gillijns, H., Van Pelt, N., Gerard, R. D., Zoldhelyi, P., Van de Werf, F., Collen, D. and Janssens, S. P. (1998) Local adenovirus-mediated transfer of human endothelial nitric oxide synthetase reduces luminal narrowing after coronary angioplasty in pigs. Circulation 98: 919–926.

Wadell, G. (1984) Molecular Epidemiology of human adenoviruses Curr. Top. Microbiol.Immunol. 110: 191–220.

Wickham, T. J., Mathias, P., Cherish, D. A., and Nemerow, G. R. (1993) Integrins avb3 and avb5 promote adenovirus internalization but not virus attachment. Cell 73: 309–319.

Wickham, T. J., Carrion, M. E. and Kovesdi, I. (1995) Targeting of adenovirus penton base to new receptors through replacement of its RGD motif with other receptor-specific peptide motifs. Gene Therapy 2: 750–756.

Wickham, T. J., Segal, D. M., Roelvink, P. W., Carrion M. E., Lizonova, A., Lee, G-M., and Kovesdi, I. (1996) Targeted adenovirus gene transfer to endothelial and smooth muscle cells by using bispecific antibodies. J. Virol. 70(10): 6831–6838.

Wickham, T. J., Lee, G-M., Titus, J. A., Sconocchia, G., Bakacs, T., Kovesdi, I. and Segal, D. M. (1997) Targeted Adenovirus-mediated gene delivery to Tcells via CD3. J. Virol. 71: 7663–7669.

Wijnberg, M. J., Quax, P. H. A., Nieuwenbroek, N. M. E., Verheijen, J. H. (1997) The migration of human smooth muscle cells in vitro is mediated by plasminogen activation and can be inhibited by al-pha(2)-macro globulin receptor associated protein. Thromb. and Haemostas. 78: 880–886.

Wold, W. S., Tollefson, A. E. and Hermiston, T. W. (1995) E3 transcription unit of adenovirus. In: W. Doerfler and P. Böhm (eds.), The molecular repertoire of adenoviruses I. Springer-Verlag, Berlin.

Zabner, J., Armentano, D., Chillon, M., Wadsworth, S. C. and Welsh, M. J. (1998) Type 17 fiber enhances gene transfer Abstract 1$^{st}$ Annual Meeting American Society of Gene Therapy, Seattle, Wash.

We claim:

1. A method of delivering a heterologous gene sequence linked to a promoter sequence into a T lymphocyte cell, a B-cell, a mast cell, or a combination thereof, each of said cells having a common binding receptor, comprising
   (a) contacting in vitro said cell with said chimeric adenoviral particle having increased tropism for said T lymphocyte cell, a B-cell, a mast cell, or a combination thereof, relative to an adenoviral particle comprising only native adenoviral sequences, said chimeric adenoviral particle comprising a viral protein coat and containing said heterologous gene sequence linked to a promoter sequence,
      wherein said viral protein coat consists of
         native viral coat proteins from an adenovirus of a serotype other than the serotype Ad51, and wherein said native viral coat proteins are penton base proteins and hexon proteins; and
         a modified fiber protein comprising a first adenoviral amino acid sequence from an adenoviral serotype Ad51 fiber protein comprising the contiguous sequence of said Ad51 fiber protein beginning at the carboxy terminus thereof and extending to but not including the N-terminus anchoring domain of said Ad51 fiber protein, and a second amino acid sequence from the fiber protein of the adenovirus of a serotype other than the serotype Ad51 comprising the N-terminus anchoring domain of the amino acid sequence of the fiber protein of the adenovirus of a serotype other than the serotype Ad35 or Ad51, wherein said first adenoviral amino acid sequence of said modified fiber protein is a ligand for said binding receptor and is not in contact with said penton base protein, and wherein said second amino acid sequence of said modified fiber protein is associated with said penton base proteins; and
   (b) allowing said chimeric adenoviral particle to transduce in vitro said T lymphocyte cell, a B-cell, a mast cell, or a combination thereof.

2. The method of claim 1 wherein said second amino acid sequence is from the adenovirus serotype Ad2 or Ad5.

3. The method of claim 2 wherein said N-terminus anchoring domain of the modified fiber protein consists essentially of about the first 35 amino acids from the N terminus of the amino acid sequence of the fiber protein of adenovirus serotype Ad2 or Ad5.

4. A method of delivering in vitro an expressible non-viral nucleic acid sequence into a T lymphocyte cell, a B-cell, a mast cell, or a combination thereof, each of said cells having a common binding receptor, said method comprising
   (a) contacting in vitro said cell with a chimeric viral particle having increased tropism for said T lymphocyte cell, a B-cell, a mast cell, or a combination thereof, relative to a native serotype Ad2 or Ad5 adenoviral particle, and comprising a viral capsid and containing said expressible non-viral nucleic acid,
      wherein said viral capsid comprises a penton base protein, a hexon protein and a chimeric fiber protein, said chimeric fiber protein comprising
         an amino acid sequence from an adenoviral serotype Ad2 or Ad5 comprising the N-terminus anchoring domain of an Ad2 or Ad5 fiber protein; and
         an amino acid sequence from an adenoviral serotype Ad51 comprising the contiguous sequence of an Ad51 fiber protein beginning at the carboxy terminus thereof and extending to but not including the N-terminus anchoring domain of said Ad51 fiber protein, wherein said amino acid sequence from an adenoviral serotype Ad51 is a ligand for said binding receptor; and
   (b) allowing said chimeric viral particle to transduce in vitro said T lymphocyte cell, a B-cell, a mast cell, or a combination thereof.

5. A method for the ex vivo delivery of an expressible non-viral nucleic acid sequence into a T lymphocyte cell, a B-cell, a mast cell, or a combination thereof, of a subject, said method comprising
   (a) obtaining from a subject a population of cells consisting essentially of T lymphocyte cells, B-cells, mast cells, or a combination thereof;
   (b) contacting in vitro to said population of cells a pharmaceutical composition comprising an effective transducing amount of a chimeric adenovirus particle comprising (i) a non-viral nucleic acid sequence, (ii) a capsid comprising (a) native capsid proteins including hexon proteins and penton base proteins, and (b) a chimeric fiber protein,
      wherein said chimeric fiber protein comprises a first amino acid sequence comprising the contiguous sequence of a Ad51 fiber protein beginning at the carboxy terminus thereof and extending to but not including the N-terminus anchoring domain of said Ad51 fiber protein,
      wherein said chimeric fiber protein comprises a second amino acid sequence comprising the N-terminus anchoring domain of the amino acid sequence of a fiber protein of an adenovirus of a serotype other than the serotype Ad51, which is a native amino acid sequence, and
      wherein said chimeric adenovirus particle has a greater tropism for said T lymphocyte cell, said B cell said mast cell, or a combination thereof relative to an adenovirus particle comprising only capsid proteins from an adenovirus other than adenovirus serotype Ad35 or Ad51;
   (b) allowing said chimeric adenovirus particle to transduce in vitro said population of cells forming a transduced cell population; and
   (c) administering said transduced cell population to said subject.

6. The method of claim 5 wherein said second amino acid sequence consists essentially of about the first 35 amino acids from the N terminus of the second fiber amino acid sequence.

7. The method of claim 6 wherein said second amino acid sequence is from Ad5.

8. The method of claim 5 wherein said non-viral nucleic acid is a cDNA.

9. A method of claim 1 wherein said cell is arranged in an array of cell subpopulations.

10. A method according to claim 9 wherein said array is comprised of multiple compartments.

11. A method according to claim 9 wherein said array is comprised of a planar surface.

12. A method according to claim 11 wherein said planar surface comprises a porous matrix.

13. A method according to claim 12 wherein said chimeric adenoviral particle is replication incompetent in said cell.

14. A method for ex vivo transduction of a population of cells from a mammal, said method comprising
   (a) obtaining from a mammal said population of cells having a common binding receptor, said cells selected from the group consisting of T lymphocytes, B cells, mast cells, or a combination thereof, and
   (b) transducing said population of cells in vitro with a replication incompetent adenoviral vector,
said replication incompetent adenoviral vector comprising a recombinant
   adenoviral nucleic acid sequence comprising
      (i) a nucleic acid sequence comprising an expressible non-viral nucleic acid, and
      (ii) a nucleic acid sequence coding for a viral capsid consisting of
         (1) native adenoviral capsid proteins, including penton base and hexon proteins, and
         (2) a modified capsid protein, wherein said modified capsid protein is a ligand for said common binding receptor and
         wherein said modified capsid protein is a chimeric fiber protein and comprises
            (a) a first amino acid sequence from a first fiber protein amino acid sequence of adenovirus serotype Ad2 or Ad5,
            wherein said first amino acid sequence comprises the N-terminus anchoring domain of and Ad2 or Ad5 fiber protein, and
            (b) a second amino acid sequence from a second fiber protein amino acid sequence of adenovirus serotype Ad51,
            wherein said second amino acid sequence comprises the contiguous sequence of said second fiber protein amino acid sequence beginning at the carboxy terminus thereof and extending to but not including the portion of said chimeric fiber protein associated with said penton base protein in said capsid.

15. The method of claim 14 wherein said first fiber protein amino acid sequence is of adenovirus Ad5.

16. The method of claim 14 wherein said non-viral nucleic acid is a cDNA.

* * * * *